(12) United States Patent
Deng et al.

(10) Patent No.: US 7,312,335 B2
(45) Date of Patent: Dec. 25, 2007

(54) ASYMMETRIC MICHAEL AND ALDOL ADDITIONS USING BIFUNCTIONAL CINCHONA-ALKALOID-BASED CATALYSTS

(75) Inventors: Li Deng, Newton, MA (US); Hongming Li, Waltham, MA (US)

(73) Assignee: Brandeis University, Waltham, MA (US)

( * ) Notice: Subject to any disclaimer, the term of this patent is extended or adjusted under 35 U.S.C. 154(b) by 51 days.

(21) Appl. No.: 11/140,574

(22) Filed: May 27, 2005

(65) Prior Publication Data

US 2006/0014956 A1 Jan. 19, 2006

Related U.S. Application Data

(60) Provisional application No. 60/592,500, filed on Jul. 30, 2004, provisional application No. 60/576,754, filed on Jun. 3, 2004.

(51) Int. Cl.
C07D 453/02 (2006.01)
C07D 453/04 (2006.01)

(52) U.S. Cl. ............... 546/135; 546/134; 546/136
(58) Field of Classification Search ......... 546/134, 546/135, 136
See application file for complete search history.

(56) References Cited

FOREIGN PATENT DOCUMENTS

WO  WO 02/05953 A2  1/2002
WO  WO 03/011799 A1  2/2003

OTHER PUBLICATIONS

Suzko et al., Roczniki Chemii, 1925, "B-Isoquinine and niquine", vol. 5, pp. 358-385.*
Barnes, D. M. et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram", *J. Am. Chem. Soc.*, 124:13097-13105 (2002).
Berner, O. M. et al., "Asymmetric Michael Additions to Nitroalkenes", *Eur. J. Org. Chem.*, 1877-1894 (2002).
Brunner, H. et al., "Asymmetric Catalysis, CIII[1]: Enantioselective *Michael* Addition of 1,3-Dicarbonyl Compounds to Conjugated Nitroalkenes", *Monatshefte für Chemie*, 127:1063-1072 (1996).
Calter, M. A., "Catalytic, Asymmetric Dimerization of Methylketene", *J. Org. Chem.*, 61:8006-8007 (1996).
Chen, Y, et al., "Asymmetric Alcoholysis of Cyclic Anhydrides", *Chem. Rev.*, 103:2965-2983 (2003).
Cortez. G. S. et al., "Bicyclic β-Lactones via Intramolecular NCAL Reactions with Cinchona Alkaloids: Effect of the C9-Substituent on Enantioselectivity and Catalyst Conformation", *Synthesis*, 11:1731-1736 (2001).
Cortez. G. S. et al., "Intramolecular, Nucleophile-Catalyzed Aldol-Lactonization (NCAL) Reactions: Catalytic, Asymmetric Synthesis of Bicyclic β-Lactones", *J. Am. Chem. Soc.*, 123:7945-7946 (2001).

France, S. et al., "Nucleophilic Chiral Amines as Catalysts in Asymmetric Synthesis", *Chem. Rev.*, 103:2985-3012 (2003).
Gröger, H., "The Development of New Monometallic Bifunctional Catalysts with Lewis acid *and* Lewis Base Properties, and their Application in Asymmetric Cyanation Reactions", *Chem. Eur. J.*, 7(24):5247-5251 (2001).
Hiemstra, H. et al., "Addition of Aromatic Thiols to Conjugated Cycloalkenones, Catalyzed by Chiral β-Hydroxy Amines. A Mechanistic Study on Homogeneous Catalytic Asymmetric Synthesis", *J. Am. Chem. Soc.*, 103:417-430 (1981).
Iwabuchi, Y. et al., "Chiral Amine-Catalyzed Asymmetric Baylis-Hillman Reaction: A Reliable Route to Highly Enantiomerically Enriched (α-Methylene-β-hydroxy)esters", *J. Am. Chem. Soc.*, 121:10219-10220 (1999).
Ji, J. et al., "Catalytic Enantioselective Conjugate Additin of 1,3-Dicarbonyl Compounds to Nitroalkenes", *J. Am. Chem. Soc.*, 121:10215-10216 (1999).
Kawahara, S. et al., "β-Isocupreidine-Catalyzed Asymmetric Baylis-Hillman Reaction of Imines", *Organic Letters*, 5(17):3103-3105 (2003).
List, B., "Asymmetric Aminocatalysis", *Synlett*, 11:1675-1686 (2001).
List, B., "Proline-catalyzed asymmetric reactions", *Tetrahedron*, 58:5573-5590 (2002).
Marcelli, T. et al., "Cinchona Derivatives as Bifunctional Organocatalysts for the Direct Asymmetric Nitroaldol (Henry) Reaction", *Synlett.*, 18:2817-2819 (2005).
Okino, T. et al., "Enantioselective *Michael* Reaction of Malonates to Nitroolefins Catalyzed by Bifunctional Organocatalysts", *J. Am. Chem. Soc.*, 125:12672-12673 (2003).
Rogers. L. M.-A. et al., "Enantioselective decarboxylation-reprotonation of an α-amino malonate derivative as a route to optically enriched cyclic α-amino acid", *Tetrahedron Letters*, 44:3047-3050 (2003).

(Continued)

*Primary Examiner*—Margaret D. Seaman
*Assistant Examiner*—Niloofar Rahmani
(74) *Attorney, Agent, or Firm*—Foley Hoag LLP; Dana M. Gordon

(57) ABSTRACT

One aspect of the present invention relates to quinine-based and quinidine-based catalysts. Another aspect of the invention relates to a method of preparing a derivatized quinine-based or quinidine-based catalyst comprising 1) reacting quinine or quinidine with base and a compound that has a suitable leaving group, and 2) converting the ring methoxy group to a hydroxy group. Another aspect of the present invention relates to a method of preparing a chiral, non-racemic compound from a prochiral electron-deficient alkene or azo compound or prochiral aldehyde or prochiral ketone, comprising the step of: reacting a prochiral electron-deficient alkene or azo compound or prochiral aldehyde or prochiral ketone with a nucleophile in the presence of a catalyst; thereby producing a chiral, non-racemic compound; wherein said catalyst is a derivatized quinine or quinidine. Another aspect of the present invention relates to a method of kinetic resolution, comprising the step of: reacting racemic chiral alkene with a nucleophile in the presence of a derivatized quinine or quinidine.

74 Claims, 25 Drawing Sheets

OTHER PUBLICATIONS

Shibasaki, M. et al., "Asymmetric Catalysis with Heterobimetallic Compounds", *Angew. Chem. Int. Ed. Engl.*, 36:1236-1256 (1997).

Shibasaki, M. et al., "Lanthanide Complexes in Multifunctional Asymmetric Catalysis", *Chem. Rev.*, 102:2187-2209 (2002).

Sibi, M. P. et al., "Enantioselective Conjugate Additions", *Tetrahedron*, 56:8033-8061 (2000).

Taggi, A. E. et al., "Catalytic, Asymmetric Synthesis of β-Lactams", *J. Am. Chem. Soc.*, 122:7831-7832 (2000).

Tian, S-K, et al., "Asymmetric Organic Catalysis with Modified Cinchona Alkaloids", *Acc. Chem. Res.* (abstract), Dec. 10, 2003.

Wack, H. et al., "Catalytic, Asymmetric α-Halogenation", *J. Am. Chem. Soc.*, 123:1531-1532 (2001).

Wynberg, H., *Asymmetric Catalysis by Alkaloids*, Department of Chemistry, University of Groningen, The Netherlands, 88-127.

Heimstra, H. et al., "Addition of Aromatic Thiols to Conjugated Cycloalkenones, Catalyzed by Chiral β-Hydroxy Amines. A Mechanistic Study on Homogeneous Catalytic Asymmetric Syntehesis", *J. Am. Chem. Soc.*, 103:417-430 (1981).

Li, H. et al., "Catalytic Enantioselective C-C Bond Forming Conjugate Additional with Vinyl Sulfones", *J. Am. Chem. Soc.*, 127:8948-8949 (2005).

Li, H. et al., "Highly Enantioselective Conjugate Addition of Malonate and β-Ketoester to Nitroalkenes: Asymmetric C-C Bond Formation with New Bifunctional Organic Catalysts Based on Cinchona Alkaloids", *J. Am. Chem. Soc.*, 126:9906-9907 (2004).

Li, H. et al., "Stereocontrolled Creation of Adjacent Quaternary and Tertiary Stereocenters by a Catalytic Conjugate Addition", *Angew. Chem. Int. Ed.*, 44:105-108 (2005).

Liu, X. et al., "Highly Enantioselective Amination of α-Substituted α-Cyanoacetates with Chiral Catalysts Accessible from Both Quinine and Quinidine", *Organic Letters*, 7(2):167-169 (2005).

Rogers, L. M. A. et al., "Enantioselective decarboxylation-reprotonation of an α-amino malonate derivative as a route to optically enriched cyclic α-amino acid", *Tetrahedron Letters*, 44:3047-3050 (2003).

Wynberg, H., "Asymmetric Catalysts by Alkaloids", *Top. Stereochem.*, 16:87-129 (1986).

\* cited by examiner

| Cat | temp | time | Conv. | dr | major (ee) | minor (ee) |
|---|---|---|---|---|---|---|
| Q-OH, | rt, | 24hr, | 95%; | 4; | 61%; | n.d. |
| Q-OH, | -25 °C, | 24hr, | 95%; | 11; | 91% | n.d. |

| Cat | temp | time | Conv. | dr | major (ee) | minor (ee) |
|---|---|---|---|---|---|---|
| Q-OH, | -25 °C, | 72 hr, | 66% (yield); | 11; | 98%; | 33% |
| Qd-OH, | -25 °C, | 24hr, | 88%; | 9.1; | -98% | -7% |

| Cat | temp | time | Conv. | dr | major (ee) | minor (ee) |
|---|---|---|---|---|---|---|
| Q-OH, | -25 °C, | 144 hr, | N.A.; | 14.8; | 96%; | n.d. |

| Cat | temp | time | Conv. | dr | major (ee) | minor (ee) |
|---|---|---|---|---|---|---|
| Q-OH, | -25 °C, | 14hr, | 95%; | 8.5; | 94%; | 16% |
| Qd-OH, | -25 °C, | 14hr, | 95%; | 5.9; | -91%; | 1.1% |
| Q-OH, | -50 °C, | 48hr, | 86%; | 15.4; | 98%; | 50% |
| Qd-OH, | -50 °C, | 48hr, | 84%; | 11.8; | -96%; | 10% |

| Cat | temp | time | Conv. | dr | major (ee) | minor (ee) |
|---|---|---|---|---|---|---|
| Q-OH, | -25 °C, | 14hr, | 95%; | 5.9; | 95%; | 20% |
| Qd-OH, | -25 °C, | 14hr, | 95%; | 4.2; | -92%; | 3% |
| Q-OH, | -50 °C, | 48hr, | 78%; | 13.3; | 97%; | 39% |
| Qd-OH, | -50 °C, | 48hr, | 70%; | 10.0; | -96%; | -17% |

| Cat | temp | time | Conv. | dr | major (ee) | minor (ee) |
|---|---|---|---|---|---|---|
| Q-OH, | -25 °C, | 65hr, | 88%; | 48; | 94%; | n.d. |

| Cat | temp | time | Conv. | dr | major (ee) | minor (ee) |
|---|---|---|---|---|---|---|
| Q-OH, | rt, | 24hr, | ; | 4; | 61%; | n.d. |

| cat | ee (%) |
|---|---|
| Q-4a | 7 |
| QD-4a | 3 |
| QD-4c | 30 |

Low conversion, 5.3 % ee    low conv. ee% --    1 day, 100% conv. ee% -- low conv. ee%19    fast clan reaction 0% ee 1h 100conv. 53 %ee    slow reaction. 40 %ee

| A-H | B | T | time | cat. | dr | yield | ee% |
|---|---|---|---|---|---|---|---|
| cyclohexanone-COOEt | phenyl | -20 | 72h | HO-Q | >40:1 | 93% | 99% |
| | 2-thienyl | -20 | 74h | HO-Q | >40:1 | 91% | 99% |
| | 4-bromophenyl | -20 | 74h | HO-Q | >40:1 | 95% | 99% |
| | isobutyl | rt | 96h | HO-Q | >40:1 | | |
| cyclopentanone-COOMe | phenyl | -60 | 48h | HO-Q-Bn | 17:1 | 94% | 99% |
| | iso-butyl | -60 | | HO-Q-Bn | >40:1 | | |
| lactone-acetyl | 4-chlorophenyl | -60 | 44h | HO-Q-Bn | 38:1 | 87% | 99% |
| | iso-butyl | -60 | 48h | HO-Q-PHN | 30:1 | 82% | 99% |

| Cat | temp | time | Conv. | dr | yield | major (ee) | minor (ee) | dr of pure product |
|---|---|---|---|---|---|---|---|---|
| Q-OH | rt | 5hr | >95% | 3.6 | ------ | 82% | 4% | ------ |
| PHN-DHQ-OH | rt | 5hr | >95% | 3.9 | ------ | 78% | 6% | ------ |
| Bn-Q-OH | rt | 5hr | >95% | 4.5 | ------ | 90% | 1% | ------ |
| Bn-Q-OH | -20 °C | 2.5 d | >95% | 13 | 76% | 98% | 2% | 11 |
| 20% Bn-Q-OH | -50 °C | 6 d | >95% | 66 | 76% | 99% | 37% | 100:1 |

| Cat | temp | time | Conv. | dr | yield | major (ee) | minor (ee) | dr of pure product |
|---|---|---|---|---|---|---|---|---|
| Q-OH | -20 °C | 3.5 d | >95% | 13 | 76% | 98% | 28% | 13 |
| Bn-Q-OH | -20 °C | 3 d | 58% | 13 | ------ | 99% | 26% | ------ |

| Cat | temp | time | Conv. | dr | yield | major (ee) | minor (ee) | dr of pure product |
|---|---|---|---|---|---|---|---|---|
| Q-OH | -20 °C | 2.5 d | >95% | 12 | 78% | 92% | n.d. | pure isomer |
| Bn-Q-OH | -20 °C | 2.5 d | >95% | 11 | ------ | 91% | n.d. | ------ |

| Cat | temp | time | Conv. | dr | yield | major (ee) | minor (ee) | dr of pure product |
|---|---|---|---|---|---|---|---|---|
| Q-OH | -20 °C | 3.5 d | >95% | 14 | 78% | 92% | 28% | pure isomer |
| Bn-Q-OH | -20 °C | 3 d | 94% | 14 | ------ | 90% | 25% | ------- |

| Cat | temp | time | Conv. | dr | yield | major (ee) | minor (ee) | dr of pure product |
|---|---|---|---|---|---|---|---|---|
| Q-OH | -20 °C | 1 d | >95% | 11 | ------ | 91% | n.d. | ----- |
| Bn-Q-OH | -20 °C | 2.5 d | >95% | 8 | ------ | 91% | n.d. | ------- |
| 20% Q-OH | -50 °C | 6 d | 87% | 20 | 77% | 96% | n.d. | 20:1 |

| Cat | temp | time | Conv. | dr | yield | major (ee) | minor (ee) | dr of pure product |
|---|---|---|---|---|---|---|---|---|
| Q-OH | -20 °C | 3.5 d | >95% | 13 | 92% | 94% | 32%. | 14 |
| Bn-Q-OH | -20 °C | 3d | 60% | 14 | ------ | 89% | 32% | ----- |

ASYMMETRIC MICHAEL AND ALDOL ADDITIONS USING BIFUNCTIONAL CINCHONA-ALKALOID-BASED CATALYSTS

RELATED APPLICATIONS

This application claims the benefit of priority to U.S. Provisional Patent Application Ser. No. 60/576,754, filed Jun. 3, 2004; and U.S. Provisional Patent Application Ser. No. 60/592,500, filed Jul. 30, 2004.

GOVERNMENT SUPPORT

The invention was made with support provided by the National Institutes of Health (GM-61591); therefore, the government has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming.

Enantiomerically pure materials may be obtained by asymmetric conjugate addition of a nucleophile to an electron-poor alkene. The asymmetric conjugate addition is one of the most powerful bond-forming reactions to construct enantioenriched, highly functional carbon skeletons for the total synthesis of natural and biologically active compounds. For reviews see: (a) B. E. Rossiter, N. M. Swingle, *Chem. Rev.* 1992, 771-806; (b) J. Leonard, E. Diez-Barra, S. Merino, *Eur. J. Org. Chem.* 1998, 2051-2061; (c) K. Tornioka, Y Nagaoka, *Comprehensive Asymmetric Catalysis* (Eds.: E. N. Jacobsen, A Pfaltz, H. Yamamoto), Springer, Berlin, 1999, vol. 3, p. 1105-1120; (d) M. Yamaguci, *Comprehensive Asymmetric Catalysis* (Eds.: E. N. Jacobsen, A Pfaltz, H. Yamamoto), Springer, Berlin, 1999, vol. 3, p. 1121-1139; (e) M. P. Sibi, S. Manyem, *Tetrahedron* 2000, 56, 8033-8061; (f) N. Krause, A. Hoffmann-Roder *Synthesis* 2001, 171-196. For general reviews on conjugate additions see: (g) P Perlmutter, *Conjugate Addition Reactions in Organic Synthesis* (Eds.: J. E. Baldwin, P D. Magnus), Pergamon Press, Oxford, 1992; (h) M. E. Jung, *Comprehensive Organic Synthesis* (Ed.: B. M. Trost), Pergamon Press, Oxford, 1991, vol. 4, pp. 1-67. Its strategic importance is evident by considering that a Michael addition can represent the initiating step of more complex inter- and intramolecular tandem processes. For reviews see: (a) L. F Tietze, *Chem. Rev.* 1996, 96,115-136; (b) R. A. Brunce, *Tetrahedron* 1995, 48, 13103-13159; (c) L. Tietze, U. Beifuss, *Angew. Chem.* 1993, 105, 137-170; *Angew Chem. Int. Ed Engl.* 1993, 32, 131-163; (d) G. H. Posner, *Chem. Rev.* 1986, 86, 831-844.

Among the Michael acceptors, nitroalkenes are very attractive, because the nitro group is the most electron-withdrawing group known. N. Ono, *The Nitro Group in Organic Synthesis*, Wiley-VCH, New York, 2001; D. Seebach, E. W. Colvin, F Lehr, T Weller, *Chimia* 1979, 33, 1-18. Often described as a "synthetic chameleon," the nitro group can serve as masked functionality to be further transformed after the addition has taken place. G. Calderari, D. Seebach, *Helv. Chim. Acta* 1995, 68, 1592-1604. The Nef reaction, the nucleophilic displacement, the reduction to amino group, the Myer reaction, and the conversion into a nitrile oxide are only examples of the transformations that nitro groups can undergo. H. W. Pinnick, Org. React. 1990, 38, 655-792; J. U. Nef, *Justus Liebigs Ann. Chem.* 1894, 280, 263-291; R. Tamura, A. Kamimura, N. Ono, *Synthesis* 1991, 423-434; R. C. Larock, *Comprehensive Organic Transformations*, VCH, New York, 1989, pp. 411-415; A. K. Beck, D. Seebach, *Chem. Ber.* 1991, 124, 2897-2911; R. E. Maeri, J. Heinzer, D. Seebach, *Liebigs Ann.* 1995, 1193-1215; M. A. Poupart, G. Fazal, S. Goulet, L. T Mar, *J. Org. Chem.* 1999, 64, 1356-1361; A. G. M. Barrett, C. D. Spilling, *Tetrahedron Lett.* 1988, 29, 5733-5734; D. H. Loyd, D. E. Nichols, *J. Org. Chem.* 1986, 51, 4294-4298; V. Meyer, C. Wurster, *Ber. Dtsch. Chem. Ges.* 1873, 6, 1168-1172; M. J. Kamlet, L. A. Kaplan, J. C. Dacons, *J. Org. Chem.* 1961, 26, 4371-4375; T. Mukayama, T Hoshino, *J. Am. Chem. Soc.* 1960, 82, 5339-5342. A number of catalytic synthetic methods have been developed in recent years, making use of nitroalkenes even more attractive. A. G. M. Barret, G. G. Graboski, *Chem. Rev.* 1986, 86, 751-762; R. Ballini, R. Castagnani, M. Petrini, *J. Org. Chem.* 1992, 57, 2160-2162; G. Rosini, R. Ballini, M. Petrini, P Sorrenti, *Synthesis* 1985, 515-517.

Conjugate additions of carbon nucleophiles to alkenyl sulfones in parallel to those to nitroalkenes constitute a class of synthetically valuable C—C bond forming reactions. Accordingly, considerable efforts have been devoted to the development of asymmetric conjugate additions to alkenyl sulfones. Although significant advancements have been made in the use of chiral auxiliary strategy, the realization of a highly enantioselective catalytic conjugate additions with alkenyl sulfones remains elusive. For reviews of enantioselective conjugate additions, see (a) Sibi, M. P.; Manyem, S. *Tetrahedron* 2000, 56, 8033-8061; (b) Krause, N.; Hoffmann-Roder, A. *Synthesis* 2001, 171-196; (c) M. Yamaguchi in Comprehensive Asymmetric Catalysis (Eds.: E. N. Jacobsen, A. Pfaltz, H. Yamamoto), Springer, Heidelberg, 2003, Suppl. 1, Supplement to chap. 31.2, p. 151. (a) Pinheiro, S.; Guingant, A.; Desmaële, D.; d'Angelo, J. *Tetrahedron: Asymmetry* 1992, 3, 1003; (b) d'Angelo, J.; Revial, G. *Tetrahedron: Asymmetry* 1991, 2, 199. Lin, Y.; Ali, B. E.; Alper, H. *J. Am. Chem. Soc.* 2001, 123, 7719. For a conjugate addition of chiral 1-aminopyrrolidine to alkenyl sulfones see: Enders, D.; Müller, S. F.; Raabe, G.; Runsink, J. *Eur. J. Org. Chem.* 2000, 879. (a) Reddick, J. J.; Cheng, J.; Roush, W. R. *Org. Lett.* 2003, 5, 1967; (b) Sanki, A. K.; Suresh, C. G.; Falgune, U. D.; Pathak, T. *Org. Lett.* 2003, 5, 1285; (c) Ravindran, B.; Sakthivel, K.; Suresh, C. G.; Pathak, T. *J. Org. Chem.* 2000, 65, 2637; (d) Farthing, C.; Marsden, S. P. *Tetrahedron Lett.* 2000, 41, 4235-4238; (e) Hirama, M.; Hioki, H.; Itô, S.; Kabuto, C. *Tetrahedron Lett.* 1988, 29, 3121. For intramolecular Michael addition to alkenyl sulfones see: Carretero, J. C.; Arrayás, R. G. *J. Org. Chem.* 1998, 63, 2993; for a Rh-catalyzed enantioselective conjugate addition of organoboronic acids to trans-β-substituted vinyl sulfones see: Mauleón, P.; Carretero, J. C. *Org. Lett.* 2004, 6, 3195.

Additionally, the conjugate addition of carbon nucleophiles to alkenyl ketones provides a powerful strategy for the creation of all-carbon quaternary stereocenters, due to the accessibility of a wide range of both the Michael donors and acceptors and the proven wide utility of the 1,4-adducts. Remarkably, in spite of numerous great strides made since then in catalytic asymmetric synthesis, this task remains a daunting challenge of undiminished synthetic significance. Wynberg, H.; Helder, R. *Tetrahedron Letters* 1975, 46, 4057-4060. Sawamura, M.; Hamashima, H.; Ito, Y. *J. Am. Chem. Soc.* 1992, 114, 8295-8296. Sasai, H.; Emori, E.; Arai, T.; Shibasaki, M. *Tetrahedron Letters* 1996, 37, 5561-5564. Hamashima, Y.; Hotta, D.; Sodeoka, M. *J. Am. Chem. Soc.* 2002, 124, 11240-11241. Bella, M.; Jorgensen, A. *J. Am. Chem. Soc.* 2004, 126, 5672-5673. For chiral (salen)Al complex-catalyzed conjugate addition of α-phenyl α-cyanoacetate to an acyclic α, β-unsaturated ketones, see Taylor, M. S.; Zalatan, D. N.; Lerchner, A. M.; Jacobsen, E. N. *J. Am. Chem. Soc.* 2005, 127, 1313-1317. For a special issue focusing on asymmetric catalysis, see: *Proc. Natl. Acad. Sci. USA* 2004, 101, 5347-5850. (b) For a thematic issue for Enantioselective Catalysis see: (Eds: Bolm, C.; Gladysz, J.) *Chem. Rev.* 2003, 103, 2761-3400. (c) *Comprehensive Asymmetric Catalysis*, E. N. Jacobsen, A. Pfaltz, H. Yamamoto Eds, Springer-Verlag, Berlin, 1999, Vol. 1-3. An enantioselective catalytic conjugate addition of α-substituted ketoesters to vinyl ketones was reported by Shibasaki and coworkers in 1994. Sasai, H.; Emori, E.; Arai, T.; Shibasaki, M. *Tetrahedron Letters* 1996, 37, 5561-5564. With a bifunctional chiral La—Na—BINOL complex, the addition of cyclic and acyclic α-substituted ketoesters to methyl vinyl ketone (MVK) proceeded in 62-91% ee. More recently, Sodeoka and coworkers reported a Pd—BINAP complex that afforded 86-93% ee for the conjugate addition of α-substituted ketoesters to methyl and ethyl vinyl ketones. Hamashima, Y.; Hotta, D.; Sodeoka, M. *J. Am. Chem. Soc.* 2002, 124, 11240-11241. These chiral metal complex-mediated reactions, while demonstrating substantial scopes with respect to ketoester donors, afforded greater than 90% ee only with MVK as the Michael acceptor. Moreover, performed at −50 to −20° C., a catalyst loading of 5-10 mol % is required for the reaction to reach completion in 15 to 72 hours. Although representing remarkable progresses, these results underscore both the urgency and challenge for the development of an operationally simple, efficient and rapid enantioselective catalytic conjugate addition of broad substrate scopes for alkenyl ketones.

The present invention relates to the catalytic asymmetric synthesis of chiral compounds from prochiral substrates, such as nitroalkenes, alkenyl sulfones and alkenyl ketones.

Catalytic asymmetric synthesis is providing chemists with new and powerful tools for the efficient synthesis of complex molecules. While many of the catalytic systems are metal-based and rely on chiral Lewis acid and organometallic redox-based catalysis, increasing numbers of asymmetric reactions are catalyzed by chiral nucleophiles, building on the vast assortment of situations in nature in which nucleophiles play pivotal roles. For leading references, see: (a) In *Comprehensive Asymmetric Catalysis*; Jacobsen, E. N., Pfaltz, A., Yamamoto, H., Eds.; Springer: Heidelberg, 1999; (b) In *Asymmetric Catalysis in Organic Synthesis*, Noyori, R., Ed.; Wiley: New York, 1994; (c) In *Asymmetric Synthesis,* 2nd ed.; Ojima, I., Ed.; VCH: New York, 2000; (d) Acc. Chem. Res. 2000, 33, 323. (e) Groger, H.; Wilken, J. *Angew. Chem., Int. Ed.* 2001, 40, 529; (f) Pierre, J.-L. *Chem. Soc. Rev.* 2000, 29, 251-257. (g) Roberts, B. P. *Chem Soc. Rev.* 1999, 28, 25. Chiral amines play a central role in this expanding area of asymmetric catalysis. Although chiral amines have been utilized extensively as chiral ligands, they have also shown great promise in catalyzing a broad range of asymmetric transformations, yielding optically enriched products in high selectivity and yield that may not be accessible through alternative asymmetric technology. Seyden-Penne, J. *Chiral Auxiliaries and Ligands in Asymmetric Synthesis*; Wiley & Sons: New York, 1995.

Historically, the cinchona alkaloids were the first chiral amines to be used in asymmetric catalysis, most notably in the pioneering work of Pracejus from the 1960's on disubstituted ketene alcoholysis. Cinchona alkaloids also possess a rich and colorful history that is rooted in natural products and pharmaceutical chemistry. Turner, R. B.; Woodward, R. B. In *In the Alkaloids*; Manske, R. H. F.; Holmes, H. L., Eds.; Academic Press: New York, 1953; Vol. 3, p 24; Verpoorte, R.; Schripsema, J.; Van der Leer, T. In *In the Alkaloids. Chemistry and Pharmacology*, Brossi, A., Ed.; Academic Press: New York, 1988; Vol. 34; Michael, J. P. In *The Quinoline Alkaloids*, In *Rodd's Chemistry of Carbon Compounds,* 2nd ed.; Sainsbury, M., Ed.; Elsevier: Amsterdam, 1998; 2nd suppl., part F and G, vol 4; 432. They are isolated en masse by extracting the bark of the cinchona tree, which is native to tropical regions. Outside of organic chemistry, the cinchona alkaloids have found wide use as food flavorings (for example as the bitter principle of tonic water) and in the treatment of malaria. Fletcher, D. C. J. *Am. Med. Assoc.* 1976, 236, 305; Mturi, N.; Musumba, C. O.; Wamula, B. M.; Ogutu, B. R.; Newton, C. R. J. C. *CNS Drugs* 2003, 17, 153. Additionally, their roles as ligands, chromatographic selectors, and NMR discriminating agents have been examined extensively over the past thirty years. Several reviews have been published on the catalytic chemistry of cinchona alkaloids over the past four decades. Pracejus, H. Forschr. *Chem. Forsch.* 1967, 8, 493; Morrison, J. D.; Mosher, H. S. *Asymmetric Organic Reactions*; Prentice Hall: Englewood Cliffs, 1971; Wynberg, H. Top. *Stereochem.* 1986, 16, 87; Kacprzak, K.; Gawronski, J. Synthesis 2001, 7, 961.

These reactions appear to be broadly applicable to both research and industrial scale asymmetric synthesis of a wide variety of important chiral building blocks, such as hemiesters, α-amino acids and α-hydroxy acids. Commercially available modified dimeric cinchona alkaloids (DHQD)$_2$AQN, (DHQ)$_2$AQN (see FIG. 1), have been identified recently by Deng and coworkers as enantioselective and recyclable catalysts for enantioselective alcoholyses of cyclic anhydrides. However, commercially available (DHQD)$_2$AQN is expensive. For example, the commercial price (Aldrich Chemical Company) for a mole of (DHQD)$_2$AQN is more than $100,000.00. Furthermore, the dimeric catalyst is not available in large quantity (e.g., in kilogram quantity). Therefore, stereoselective reactions using dimeric catalysts are not practical on a relatively large scale (>0.1 mol). Consequently, the development of a new generation of monomeric catalysts that is comparably effective to (DHQD)$_2$AQN, but substantially less costly to produce, is of significant practical value.

Chiral metal and organic catalysts that possess both an acidic and a basic/nucleophilic structural moiety constitute an increasingly powerful platform for the development of asymmetric catalysis. The design and development of such bifunctional chiral catalysts that are efficient yet easily accessible continues to be a major challenge. Wynberg and coworkers demonstrated that natural cinchona alkaloids, via their C9-OH and amine groups, served as bifunctional chiral organic catalysts by activating the nucleophile and electrophile, respectively, for enantioselective reactions. Wynberg, H., Hiemstra, H., *J. Am. Chem. Soc.*, 1981, 103, 417. However, the enantioselectivity of various reactions catalyzed by natural cinchona alkaloids as chiral organic catalysts was usually modest. Hatakeyama and coworkers recently reported a rigid modified cinchona alkaloid that is readily accessible from quinidine. Hatakeyama, S. et al., *J. Am. Chem. Soc.,* 1999, 121, 10219; Hatakeyama, S., *Organic Lett.,* 2003, 5, 3103. The catalyst was found to be efficient for an enantioselective Morita-Baylis-Hillman (MBH) reaction. Both the C6'-OH and the amine groups are believed to be involved in the stabilization of the transition state of the enantioselective MBH reaction.

Remarkably, we have developed readily accessible bifunctional organic catalysts that can be derived from either quinidine or quinine and their successful use for a highly enantioselective C—C bond forming reaction.

SUMMARY OF THE INVENTION

One aspect of the present invention relates generally to quinine- and quinidine-based catalysts. In certain embodiments, the quinine- and quinidine-based catalysts contain a hydrogen bond donating group at the 6' position. In certain embodiments, the quinine- and quinidine-based catalysts contain a hydroxy group at the 6' position. In certain embodiments, the quinine- and quinidine-based catalysts contain an O-aryl group or an O-aralkyl group at the C9 position. In preferred embodiments, the quinine- and quinidine-based catalysts contain an O-phenanthrene group or an O-benzyl group at the C9 position.

Another aspect of the invention relates to a method of preparing a derivatized quinine- or quinidine-based catalyst comprising 1) reacting quinine or quinidine with base and a compound that has a suitable leaving group, and 2) converting the ring methoxy group to a hydroxy group. In certain embodiments, the leaving group is Cl, Br, I, $OSO_2CH_3$, or $OSO_2CF_3$. In a preferred embodiment, the leaving group is Cl or I. In a preferred embodiment, the base is a metal hydride. In a preferred embodiment, the hydroxyl group of the quinine- or quinidine-based catalyst undergoes reaction with an aryl or aralkyl halide.

Another aspect of the present invention relates to a method of preparing a chiral, non-racemic compound from a prochiral electron-deficient alkene or azo compound or prochiral aldehyde or prochiral ketone, comprising the step of: reacting a prochiral electron-deficient alkene or azo compound or prochiral aldehyde or prochiral ketone with a nucleophile in the presence of a catalyst; thereby producing a chiral, non-racemic compound; wherein said catalyst is a derivatized quinine or quinidine. In certain embodiments, the nucleophile is a malonate or a β-ketoester. In certain embodiments the nucleophile is an alkyl or aryl or aralkyl 2-cyano-2-alkylacetate. In certain embodiments the nucleophile is an alkyl or aryl or aralkyl 2-cyano-2-arylacetate.

In preferred embodiments, the nucleophile is dimethyl or diethyl malonate. In certain embodiments, the prochiral electron-deficient alkene or azo compound or prochiral aldehyde or prochiral ketone is a nitroalkene. In certain embodiments, the prochiral electron-deficient alkene or azo compound or prochiral aldehyde or prochiral ketone is an alkenyl sulfone. In certain embodiments, the prochiral electron-deficient alkene or azo compound or prochiral aldehyde or prochiral ketone is an alkenyl ketone. In certain embodiments, the catalyst is present in less than about 70 mol % relative to said prochiral electron-deficient alkene or azo compound or prochiral aldehyde or prochiral ketone. In a preferred embodiment, the catalyst is present in less than about 10 mol % relative to said prochiral electron-deficient alkene or azo compound or prochiral aldehyde or prochiral ketone. In a preferred embodiment, the catalyst is present in less than about 5 mol % relative to said prochiral electron-deficient alkene or azo compound or prochiral aldehyde or prochiral ketone. In certain embodiment, the chiral, non-racemic compound has an enantiomeric excess greater than about 90%.

Another aspect of the present invention relates to a method of kinetic resolution, comprising the step of: reacting racemic chiral alkene with a nucleophile in the presence of a derivatized quinine or quinidine. In a preferred embodiment, the nucleophile is a malonate or a β-ketoester. In a preferred embodiment, the nucleophile is an alkyl or aryl or aralkyl 2-cyano-2-alkylacetate. In a preferred embodiment, the nucleophile is an alkyl or aryl or aralkyl 2-cyano-2-arylacetate.

BRIEF DESCRIPTION OF THE DRAWINGS

FIG. 13 depicts the kinetic determination of the order of nitroalkene (2a). The graph shows a linear relationship between ln[2a] and time indicating the reaction is first order in 2a.

FIG. 14 depicts the kinetic determination of the order of nitroalkene (4a). The graph shows a nonlinear relationship between 1/[4a] and time indicating the reaction is not second order in 2a.

DETAILED DESCRIPTION OF THE INVENTION

Definitions

Figure 1:
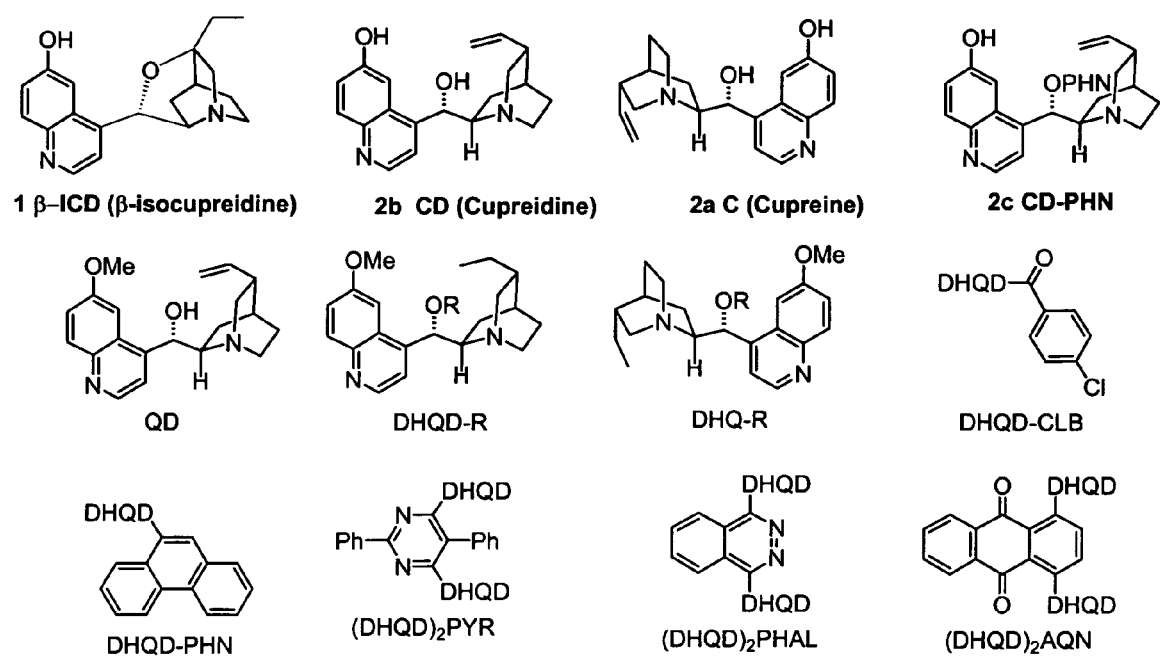
FIG. 1 depicts the structure and nomenclature of several cinchona-alkaloid-based catalysts of the present invention.

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "Bronsted base" is art-recognized and refers to an uncharged or charged atom or molecule, e.g., an oxide, amine, alkoxide, or carbonate, that is a proton acceptor.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an ee for a particular enantiomer that is larger than the ee of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A$ (ee)=(% Enantiomer $A$)−(% Enantiomer $B$)

where A and B are the enantiomers formed. Additional terms that are used in conjunction with enatioselectivity include "optical purity" or "optical activity". An enantioselective reaction yields a product with an ee greater than zero. Preferred enantioselective reactions yield a product with an ee greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

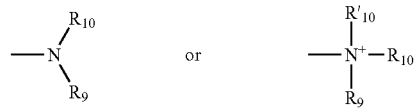

wherein $R_9$, $R_{10}$ and $R'_{10}$ each independently represent a group permitted by the rules of valence.

The term "acylamino" is art-recognized and refers to a moiety that can be represented by the general formula:

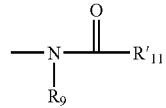

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art-recognized as an amino-substituted carbonyl and includes a moiety that can be represented by the general formula:

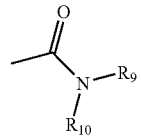

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art-recognized and includes such moieties as can be represented by the general formula:

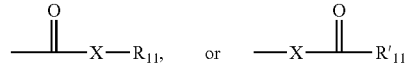

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art-recognized and includes a moiety that can be represented by the general formula:

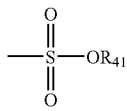

in which $R_{41}$ is an electron pair, hydrogen, alkyl, cycloalkyl, or aryl.

The term "sulfonylamino" is art-recognized and includes a moiety that can be represented by the general formula:

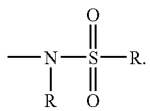

The term "sulfamoyl" is art-recognized and includes a moiety that can be represented by the general formula:

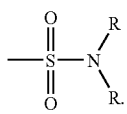

The term "sulfonyl", as used herein, refers to a moiety that can be represented by the general formula:

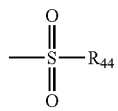

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

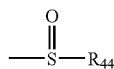

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

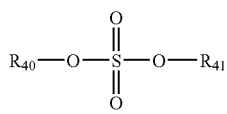

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, naphthalene, anthracene, phenanthrene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "aralkyl", as used herein, refers to an alkyl group substituted with an aryl group (as defined above). For example, a benzyl group (—$CH_2Ph$) is an aralkyl group.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986-87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The term "1-adamantyl" is art-recognized and includes a moiety represented by the formula:

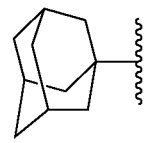

The term "(−)-menthyl" is art-recognized and includes a moiety represented by the formula:

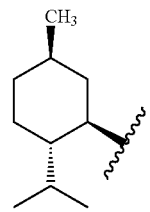

The term "(+)-menthyl" is art-recognized and includes a moiety represented by the formula:

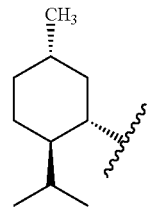

The term "isobornyl" is art-recognized and includes a moiety represented by the formula:

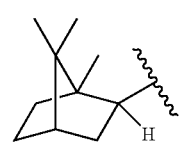

The term "isopinocamphyl" is art-recognized and includes a moiety represented by the formula:

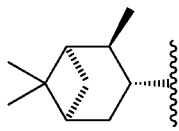

The term "(+)-fenchyl" is art-recognized and includes a moiety represented by the formula:

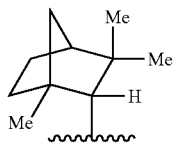

The abbreviation "QD" represents a moiety according to the following formula:

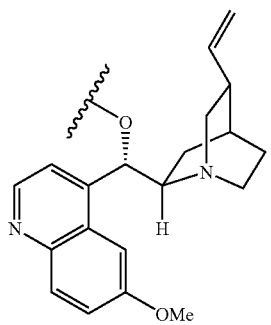

The term "Q" represents a moiety according to the following formula:

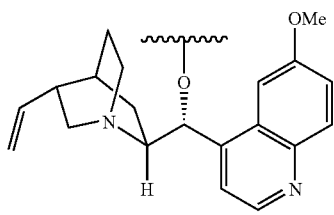

Catalysts of the Invention

The catalysts employed in the subject methods are non-racemic chiral amines which present an asymmetric environment, causing stereochemical discrimination between two stereogenic faces of an alkene; or two or more prochiral moieties (e.g., related by symmetry in a prochiral or meso molecule, (i.e., a molecule comprising at least two chiral centers), both of which comprise an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity.

As mentioned above, the choice of catalyst substituents can also effect the electronic properties of the catalyst. Substitution of the catalyst with electron-rich (electron-donating) moieties (for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

One aspect of the present invention relates to a compound represented by formula I:

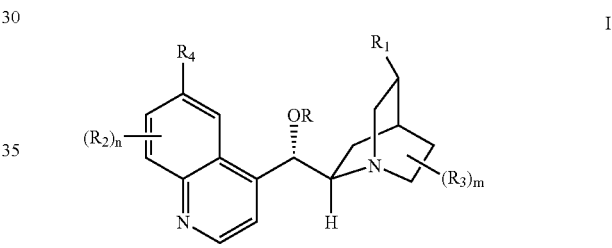

wherein, independently for each occurrence:

R represents a substituted or unsubstituted alkyl, alkenyl, alkynyl, aryl, aralkyl, heteroaryl, heteroaralkyl, heterocyclic, or heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$.

In certain embodiments, the compounds of the present invention are represented by formula I and any of the attendant definitions, wherein $R_4$ represents —OH.

In certain embodiments, the compounds of the present invention are represented by formula I and any of the attendant definitions, wherein R represents aryl or aralkyl.

In certain embodiments, the compounds of the present invention are represented by formula I and any of the attendant definitions, wherein R represents aryl.

In certain embodiments, the compounds of the present invention are represented by formula I and any of the attendant definitions, wherein R represents phenanthrene.

In certain embodiments, the compounds of the present invention are represented by formula I and any of the attendant definitions, wherein R represents aralkyl.

In certain embodiments, the compounds of the present invention are represented by formula I and any of the attendant definitions, wherein R represents benzyl.

In certain embodiments, the compounds of the present invention are represented by formula I and any of the attendant definitions, wherein $R_1$ is alkyl.

In certain embodiments, the compounds of the present invention are represented by formula I and any of the attendant definitions, wherein $R_1$ is ethyl.

In certain embodiments, the compounds of the present invention are represented by formula I and any of the attendant definitions, wherein $R_1$ is alkenyl.

In certain embodiments, the compounds of the present invention are represented by formula I and any of the attendant definitions, wherein $R_1$ is —CH=$CH_2$.

In certain embodiments, the compounds of the present invention are represented by formula I and any of the attendant definitions, wherein n is 0.

In certain embodiments, the compounds of the present invention are represented by formula I and any of the attendant definitions, wherein m is 0.

In certain embodiments, the compounds of the present invention are represented by formula I and any of the attendant definitions, wherein R is aryl and $R_1$ is alkyl.

In certain embodiments, the compounds of the present invention are represented by formula I and any of the attendant definitions, wherein R is phenanthrene and $R_1$ is alkyl.

In certain embodiments, the compounds of the present invention are represented by formula I and any of the attendant definitions, wherein R is phenanthrene and $R_1$ is ethyl.

In certain embodiments, the compounds of the present invention are represented by formula I and any of the attendant definitions, wherein R is aryl and $R_1$ is alkenyl.

In certain embodiments, the compounds of the present invention are represented by formula I and any of the attendant definitions, wherein R is phenanthrene and $R_1$ is alkenyl.

In certain embodiments, the compounds of the present invention are represented by formula I and any of the attendant definitions, wherein R is phenanthrene and $R_1$ is —CH=$CH_2$.

In certain embodiments, the compounds of the present invention are represented by formula I and any of the attendant definitions, wherein R is aralkyl and $R_1$ is alkyl.

In certain embodiments, the compounds of the present invention are represented by formula I and any of the attendant definitions, wherein R is benzyl and $R_1$ is alkyl.

In certain embodiments, the compounds of the present invention are represented by formula I and any of the attendant definitions, wherein R is benzyl and $R_1$ is ethyl.

In certain embodiments, the compounds of the present invention are represented by formula I and any of the attendant definitions, wherein R is aralkyl and $R_1$ is alkenyl.

In certain embodiments, the compounds of the present invention are represented by formula I and any of the attendant definitions, wherein R is benzyl and $R_1$ is alkenyl.

In certain embodiments, the compounds of the present invention are represented by formula I and any of the attendant definitions, wherein R is benzyl and $R_1$ is —CH=$CH_2$.

In certain embodiments, the compounds of the present invention are represented by formula I and any of the attendant definitions, wherein R is aryl, $R_1$ is alkyl, m is 0, and n is 0.

In certain embodiments, the compounds of the present invention are represented by formula I and any of the attendant definitions, wherein R is phenanthrene, $R_1$ is alkyl, m is 0, and n is 0.

In certain embodiments, the compounds of the present invention are represented by formula I and any of the attendant definitions, wherein R is phenanthrene, $R_1$ is ethyl, m is 0, and n is 0.

In certain embodiments, the compounds of the present invention are represented by formula I and any of the attendant definitions, wherein R is aryl, $R_1$ is alkenyl, m is 0, and n is 0.

In certain embodiments, the compounds of the present invention are represented by formula I and any of the attendant definitions, wherein R is phenanthrene, $R_1$ is alkenyl, m is 0, and n is 0.

In certain embodiments, the compounds of the present invention are represented by formula I and any of the attendant definitions, wherein R is phenanthrene, $R_1$ is —CH=$CH_2$, m is 0, and n is 0.

In certain embodiments, the compounds of the present invention are represented by formula I and any of the attendant definitions, wherein R is aralkyl, $R_1$ is alkyl, m is 0, and n is 0.

In certain embodiments, the compounds of the present invention are represented by formula I and any of the attendant definitions, wherein R is benzyl, $R_1$ is alkyl, m is 0, and n is 0.

In certain embodiments, the compounds of the present invention are represented by formula I and any of the attendant definitions, wherein R is benzyl, $R_1$ is ethyl, m is 0, and n is 0.

In certain embodiments, the compounds of the present invention are represented by formula I and any of the attendant definitions, wherein R is aralkyl, $R_1$ is alkenyl, m is 0, and n is 0.

In certain embodiments, the compounds of the present invention are represented by formula I and any of the attendant definitions, wherein R is benzyl, $R_1$ is alkenyl, m is 0, and n is 0.

In certain embodiments, the compounds of the present invention are represented by formula I and any of the attendant definitions, wherein R is benzyl, $R_1$ is —CH=$CH_2$, m is 0, and n is 0.

Another aspect of the present invention relates to a compound represented by formula II:

wherein, independently for each occurrence:

R represents a substituted or unsubstituted alkyl, alkenyl, alkynyl, aryl, aralkyl, heteroaryl, heteroaralkyl, heterocyclic, or heterocycloalkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$.

In certain embodiments, the compounds of the present invention are represented by formula II and any of the attendant definitions, wherein $R_4$ represents —OH.

In certain embodiments, the compounds of the present invention are represented by formula II and any of the attendant definitions, wherein R represents aryl or aralkyl.

In certain embodiments, the compounds of the present invention are represented by formula II and any of the attendant definitions, wherein R represents aryl.

In certain embodiments, the compounds of the present invention are represented by formula II and any of the attendant definitions, wherein R represents phenanthrene.

In certain embodiments, the compounds of the present invention are represented by formula II and any of the attendant definitions, wherein R represents aralkyl.

In certain embodiments, the compounds of the present invention are represented by formula II and any of the attendant definitions, wherein R represents benzyl.

In certain embodiments, the compounds of the present invention are represented by formula II and any of the attendant definitions, wherein $R_1$ is alkyl.

In certain embodiments, the compounds of the present invention are represented by formula II and any of the attendant definitions, wherein $R_1$ is ethyl.

In certain embodiments, the compounds of the present invention are represented by formula II and any of the attendant definitions, wherein $R_1$ is alkenyl.

In certain embodiments, the compounds of the present invention are represented by formula II and any of the attendant definitions, wherein $R_1$ is —CH=CH$_2$.

In certain embodiments, the compounds of the present invention are represented by formula II and any of the attendant definitions, wherein n is 0.

In certain embodiments, the compounds of the present invention are represented by formula II and any of the attendant definitions, wherein m is 0.

In certain embodiments, the compounds of the present invention are represented by formula II and any of the attendant definitions, wherein R is aryl and $R_1$ is alkyl.

In certain embodiments, the compounds of the present invention are represented by formula II and any of the attendant definitions, wherein R is phenanthrene and $R_1$ is alkyl.

In certain embodiments, the compounds of the present invention are represented by formula II and any of the attendant definitions, wherein R is phenanthrene and $R_1$ is ethyl.

In certain embodiments, the compounds of the present invention are represented by formula II and any of the attendant definitions, wherein R is aryl and $R_1$ is alkenyl.

In certain embodiments, the compounds of the present invention are represented by formula II and any of the attendant definitions, wherein R is phenanthrene and $R_1$ is alkenyl.

In certain embodiments, the compounds of the present invention are represented by formula II and any of the attendant definitions, wherein R is phenanthrene and $R_1$ is —CH=CH$_2$.

In certain embodiments, the compounds of the present invention are represented by formula II and any of the attendant definitions, wherein R is aralkyl and $R_1$ is alkyl.

In certain embodiments, the compounds of the present invention are represented by formula II and any of the attendant definitions, wherein R is benzyl and $R_1$ is alkyl.

In certain embodiments, the compounds of the present invention are represented by formula II and any of the attendant definitions, wherein R is benzyl and $R_1$ is ethyl.

In certain embodiments, the compounds of the present invention are represented by formula II and any of the attendant definitions, wherein R is aralkyl and $R_1$ is alkenyl.

In certain embodiments, the compounds of the present invention are represented by formula II and any of the attendant definitions, wherein R is benzyl and $R_1$ is alkenyl.

In certain embodiments, the compounds of the present invention are represented by formula II and any of the attendant definitions, wherein R is benzyl and $R_1$ is —CH=CH$_2$.

In certain embodiments, the compounds of the present invention are represented by formula II and any of the attendant definitions, wherein R is aryl, $R_1$ is alkyl, m is 0, and n is 0.

In certain embodiments, the compounds of the present invention are represented by formula II and any of the attendant definitions, wherein R is phenanthrene, $R_1$ is alkyl, m is 0, and n is 0.

In certain embodiments, the compounds of the present invention are represented by formula II and any of the attendant definitions, wherein R is phenanthrene, $R_1$ is ethyl, m is 0, and n is 0.

In certain embodiments, the compounds of the present invention are represented by formula II and any of the attendant definitions, wherein R is aryl, $R_1$ is alkenyl, m is 0, and n is 0.

In certain embodiments, the compounds of the present invention are represented by formula II and any of the attendant definitions, wherein R is phenanthrene, $R_1$ is alkenyl, m is 0, and n is 0.

In certain embodiments, the compounds of the present invention are represented by formula II and any of the attendant definitions, wherein R is phenanthrene, $R_1$ is —CH=CH$_2$, m is 0, and n is 0.

In certain embodiments, the compounds of the present invention are represented by formula II and any of the attendant definitions, wherein R is aralkyl, $R_1$ is alkyl, m is 0, and n is 0.

In certain embodiments, the compounds of the present invention are represented by formula II and any of the attendant definitions, wherein R is benzyl, $R_1$ is alkyl, m is 0, and n is 0.

In certain embodiments, the compounds of the present invention are represented by formula II and any of the attendant definitions, wherein R is benzyl, $R_1$ is ethyl, m is 0, and n is 0.

In certain embodiments, the compounds of the present invention are represented by formula II and any of the attendant definitions, wherein R is aralkyl, $R_1$ is alkenyl, m is 0, and n is 0.

In certain embodiments, the compounds of the present invention are represented by formula II and any of the attendant definitions, wherein R is benzyl, $R_1$ is alkenyl, m is 0, and n is 0.

In certain embodiments, the compounds of the present invention are represented by formula II and any of the attendant definitions, wherein R is benzyl, $R_1$ is —CH=$CH_2$, m is 0, and n is 0.

Methods of the Invention—Preparation of Asymmetric Bifunctional Catalysts

One aspect of the invention relates to a method of preparing a bifunctional catalyst as depicted in Scheme 1:

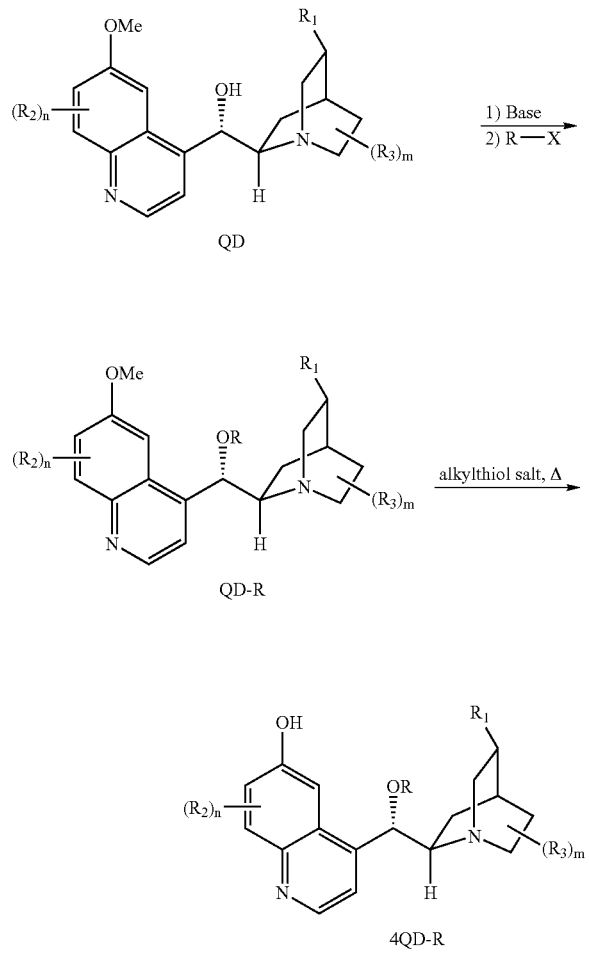

wherein, independently for each occurrence:

X represents Cl, Br, I, $OSO_2CH_3$, or $OSO_2CF_3$;

R represents a substituted or unsubstituted alkyl, alkenyl, alkynyl, aryl, aralkyl, heteroaryl, heteroaralkyl, heterocyclic, or heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and base is a Brønsted base.

In certain embodiments, the present invention relates to the aforementioned method and any of the attendant definitions, wherein X is Cl or I.

In certain embodiments, the present invention relates to the aforementioned method and any of the attendant definitions, wherein said base is a metal hydride, alkoxide, amide, or carbanion.

In certain embodiments, the present invention relates to the aforementioned method and any of the attendant definitions, wherein said base is NaH, $CaH_2$, KH, or Na.

In certain embodiments, the present invention relates to the aforementioned method and any of the attendant definitions, wherein R represents aryl or aralkyl.

In certain embodiments, the present invention relates to the aforementioned method and any of the attendant definitions, wherein R represents aryl.

In certain embodiments, the present invention relates to the aforementioned method and any of the attendant definitions, wherein R represents phenanthrene.

In certain embodiments, the present invention relates to the aforementioned method and any of the attendant definitions, wherein R represents aralkyl.

In certain embodiments, the present invention relates to the aforementioned method and any of the attendant definitions, wherein R represents benzyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is phenanthrene and $R_1$ is alkyl.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is phenanthrene and $R_1$ is alkenyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is benzyl and $R_1$ is alkyl.

In certain embodiments, the present invention relates to the aforementioned method and any of the attendant definitions, wherein R is benzyl and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is benzyl and $R_1$ is alkenyl.

In certain embodiments, the present invention relates to the aforementioned method and any of the attendant definitions, wherein R is benzyl and $R_1$ is —CH=$CH_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is phenanthrene, $R_1$ is alkyl, m is 0, and n is 0.

In certain embodiments, the present invention relates to the aforementioned method and any of the attendant definitions, wherein R is phenanthrene, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is phenanthrene, $R_1$ is alkenyl, m is 0, and n is 0.

In certain embodiments, the present invention relates to the aforementioned method and any of the attendant definitions, wherein R is phenanthrene, $R_1$ is —CH=$CH_2$, m is 0, and n is 0.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is benzyl, $R_1$ is alkyl, m is 0, and n is 0.

In certain embodiments, the present invention relates to the aforementioned method and any of the attendant definitions, wherein R is benzyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is benzyl, $R_1$ is alkenyl, m is 0, and n is 0.

In certain embodiments, the present invention relates to the aforementioned method and any of the attendant definitions, wherein R is benzyl, $R_1$ is —CH=$CH_2$, m is 0, and n is 0.

Another aspect of the invention relates to a method of preparing a bifunctional catalyst as depicted in Scheme 2:

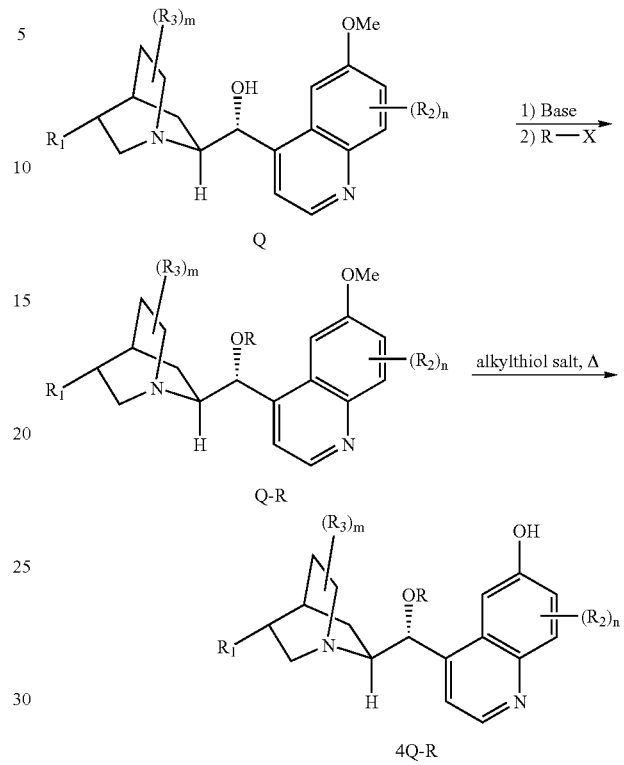

wherein, independently for each occurrence:
  X represents Cl, Br, I, $OSO_2CH_3$, or $OSO_2CF_3$;
  R represents a substituted or unsubstituted alkyl, alkenyl, alkynyl, aryl, aralkyl, heteroaryl, heteroaralkyl, heterocyclic, or heterocycloalkyl;
  $R_1$ represents alkyl or alkenyl;
  $R_2$ and $R_3$ represent alkyl, alkenyl, aryl, cycloalkyl, aralkyl, heteroalkyl, halogen, hydroxy, cyano, amino, acyl, alkoxyl, amino, silyloxy, amino, nitro, thiol, amine, imine, amide, phosphonate, phosphine, carbonyl, carboxyl, silyl, ether, thioether, sulfonyl, selenoether, ketone, aldehyde, or ester;
  n is an integer from 0 to 5 inclusive;
  m is an integer from 0 to 8 inclusive; and
  base is a Bronsted base.

In certain embodiments, the present invention relates to the aforementioned method and any of the attendant definitions, wherein X is Cl or I.

In certain embodiments, the present invention relates to the aforementioned method and any of the attendant definitions, wherein said base is a metal hydride, alkoxide, amide, or carbanion.

In certain embodiments, the present invention relates to the aforementioned method and any of the attendant definitions, wherein said base is NaH, $CaH_2$, KH, or Na.

In certain embodiments, the present invention relates to the aforementioned method and any of the attendant definitions, wherein R represents aryl or aralkyl.

In certain embodiments, the present invention relates to the aforementioned method and any of the attendant definitions, wherein R represents aryl.

In certain embodiments, the present invention relates to the aforementioned method and any of the attendant definitions, wherein R represents phenanthrene.

In certain embodiments, the present invention relates to the aforementioned method and any of the attendant definitions, wherein R represents aralkyl.

In certain embodiments, the present invention relates to the aforementioned method and any of the attendant definitions, wherein R represents benzyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is phenanthrene and $R_1$ is alkyl.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is phenanthrene and $R_1$ is alkenyl.

In certain embodiments, the present invention relates to the aforementioned method and any of the attendant definitions, wherein R is phenanthrene and $R_1$ is —CH=CH$_2$.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is benzyl and $R_1$ is alkyl.

In certain embodiments, the present invention relates to the aforementioned method and any of the attendant definitions, wherein R is benzyl and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is benzyl and $R_1$ is alkenyl.

In certain embodiments, the present invention relates to the aforementioned method and any of the attendant definitions, wherein R is benzyl and $R_1$ is —CH=CH$_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is phenanthrene, $R_1$ is alkyl, m is 0, and n is 0.

In certain embodiments, the present invention relates to the aforementioned method and any of the attendant definitions, wherein R is phenanthrene, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is phenanthrene, $R_1$ is alkenyl, m is 0, and n is 0.

In certain embodiments, the present invention relates to the aforementioned method and any of the attendant definitions, wherein R is phenanthrene, $R_1$ is —CH=CH$_2$, m is 0, and n is 0.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is benzyl, $R_1$ is alkyl, m is 0, and n is 0.

In certain embodiments, the present invention relates to the aforementioned method and any of the attendant definitions, wherein R is benzyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is benzyl, $R_1$ is alkenyl, m is 0, and n is 0.

In certain embodiments, the present invention relates to the aforementioned method and any of the attendant definitions, wherein R is benzyl, $R_1$ is —CH=CH$_2$, m is 0, and n is 0.

Methods of the Invention—Catalyzed Reactions

In one aspect of the present invention there is provided a process for stereoselectively producing compounds with at least one stereogenic center from prochiral, or racemic starting materials. An advantage of this invention is that enantiomerically enriched products can be synthesized from prochiral or racemic reactants. Another advantage is that yield losses associated with the production of an undesired enantiomer can be substantially reduced or eliminated altogether.

In general, the invention features a stereoselective conjugate addition process which comprises combining a nucleophilic reactant, a prochiral or chiral substrate, and at least a catalytic amount of non-racemic chiral catalyst of particular characteristics (as described below). The substrate of the reaction will include alkenes susceptible to attack by the nucleophile. The combination is maintained under conditions appropriate for the chiral catalyst to catalyze the conjugate addition between the nucleophilic reactant and alkene substrate. This reaction can be applied to enantioselective processes as well as diastereoselective processes. It may also be adapted for regioselective reactions. Examples of enantioselective reactions, kinetic resolutions, and regioselective reactions which may be catalyzed according to the present invention follow.

The processes of this invention can provide optically active products with very high stereoselectivity (e.g., enantioselectivity or diastereoselectivity) or regioselectivity. In preferred embodiments of the subject desymmetrization reactions, products with enantiomeric excesses of greater than about 50%, greater than about 70%, greater than about 90%, and most preferably greater than about 95% can be obtained. The processes of this invention can also be carried out under reaction conditions suitable for commercial use, and typically proceed at reaction rates suitable for large scale operations.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include the Nef reaction, the nucleophilic displacement, the reduction to amino group, the Myer reaction, the conversion into a nitrile oxide, and the like (Scheme 3).

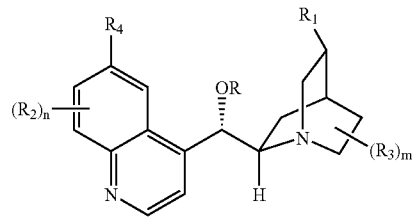

I

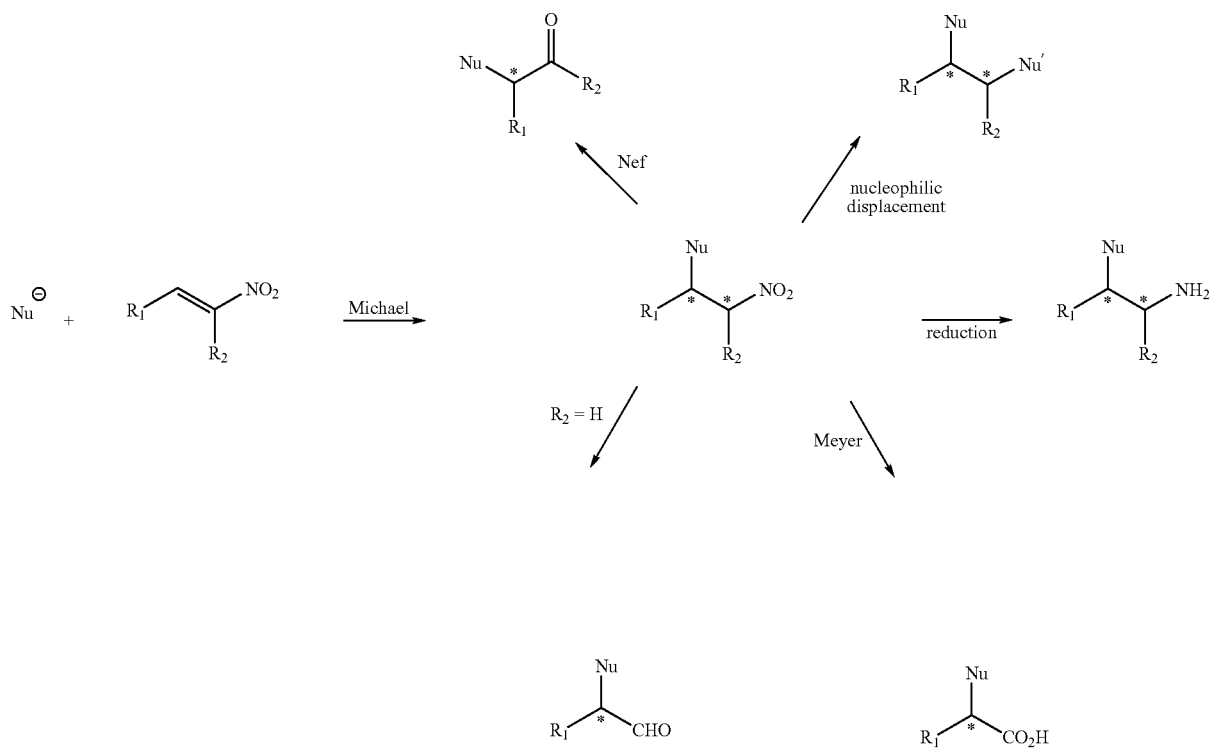

Scheme 3. Various derivatizations of the chiral product of the invention.

The invention expressly contemplates the preparation of end-products and synthetic intermediates which are useful for the preparation or development or both of therapeutic compounds.

One aspect of the present invention relates to a method of preparing a chiral, non-racemic compound from a prochiral electron-deficient alkene or azo compound or prochiral aldehyde or prochiral ketone, comprising the step of:

reacting a prochiral electron-deficient alkene or azo compound or prochiral aldehyde or prochiral ketone with a nucleophile in the presence of a catalyst; thereby producing a chiral, non-racemic compound; wherein said catalyst is represented by formula I:

wherein, independently for each occurrence:

R represents H or a substituted or unsubstituted alkyl, alkenyl, alkynyl, aryl, aralkyl, heteroaryl, heteroaralkyl, heterocyclic, or heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —$NH_2$, —$NHR_2$—NH(C=O)$NR_2R_3$, —NH($SO_2$)$R_2$, —NH(C=O)$OR_2$, or —NH(C=O)$R_2$.

In certain embodiments, the present invention relates to the aforementioned method and any of the attendant definitions, wherein $R_4$ represents —OH.

In certain embodiments, the present invention relates to the aforementioned method and any of the attendant definitions, wherein R represents H, aryl, or aralkyl.

In certain embodiments, the present invention relates to the aforementioned method and any of the attendant definitions, wherein R represents H.

In certain embodiments, the present invention relates to the aforementioned method and any of the attendant definitions, wherein R represents aryl.

In certain embodiments, the present invention relates to the aforementioned method and any of the attendant definitions, wherein R represents phenanthrene.

In certain embodiments, the present invention relates to the aforementioned method and any of the attendant definitions, wherein R represents aralkyl.

In certain embodiments, the present invention relates to the aforementioned method and any of the attendant definitions, wherein R represents benzyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is H and $R_1$ is alkyl.

In certain embodiments, the present invention relates to the aforementioned method and any of the attendant definitions, wherein R is H and $R_1$ is ethyl.

In certain embodiments, the present invention relates to the aforementioned method and any of the attendant definitions, wherein R is H and $R_1$ is alkenyl.

In certain embodiments, the present invention relates to the aforementioned method and any of the attendant definitions, wherein R is H and $R_1$ is —CH=$CH_2$.

In certain embodiments, the present invention relates to the aforementioned method and any of the attendant definitions, wherein R is H, $R_1$ is alkyl, m is 0, and n is 0.

In certain embodiments, the present invention relates to the aforementioned method and any of the attendant definitions, wherein R is H, $R_1$ is ethyl, m is 0, and n is 0.

In certain embodiments, the present invention relates to the aforementioned method and any of the attendant definitions, wherein R is H, $R_1$ is alkenyl, m is 0, and n is 0.

In certain embodiments, the present invention relates to the aforementioned method and any of the attendant definitions, wherein R is H, $R_1$ is —CH=$CH_2$, m is 0, and n is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is phenanthrene and $R_1$ is alkyl.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is phenanthrene and $R_1$ is alkenyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is benzyl and $R_1$ is alkyl.

In certain embodiments, the present invention relates to the aforementioned method and any of the attendant definitions, wherein R is benzyl and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is benzyl and $R_2$ is alkenyl.

In certain embodiments, the present invention relates to the aforementioned method and any of the attendant definitions, wherein R is benzyl and $R_1$ is —CH=$CH_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is phenanthrene, $R_1$ is alkyl, m is 0, and n is 0.

In certain embodiments, the present invention relates to the aforementioned method and any of the attendant definitions, wherein R is phenanthrene, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is phenanthrene, $R_1$ is alkenyl, m is 0, and n is 0.

In certain embodiments, the present invention relates to the aforementioned method and any of the attendant definitions, wherein R is phenanthrene, $R_1$ is —CH=$CH_2$, m is 0, and n is 0.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is benzyl, $R_1$ is alkyl, m is 0, and n is 0.

In certain embodiments, the present invention relates to the aforementioned method and any of the attendant definitions, wherein R is benzyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is benzyl, $R_1$ is alkenyl, m is 0, and n is 0.

In certain embodiments, the present invention relates to the aforementioned method and any of the attendant definitions, wherein R is benzyl, $R_1$ is —CH=$CH_2$, m is 0, and n is 0.

In certain embodiments, the present invention relates to the aforementioned method and any of the attendant definitions, wherein said nucleophile is a secondary or tertiary nucleophile.

In certain embodiments, the present invention relates to the aforementioned method and any of the attendant definitions, wherein said nucleophile is a secondary nucleophile.

In certain embodiments, the present invention relates to the aforementioned method and any of the attendant definitions, wherein said nucleophile is a tertiary nucleophile.

In certain embodiments, the present invention relates to the aforementioned method and any of the attendant definitions, wherein said nucleophile is a malonate or a β-ketoester.

In certain embodiments, the present invention relates to the aforementioned method and any of the attendant definitions, wherein said nucleophile is dimethyl malonate.

In certain embodiments, the present invention relates to the aforementioned method and any of the attendant definitions, wherein said nucleophile is an alkyl or aryl or aralkyl 2-cyano-2-alkylacetate.

In certain embodiments, the present invention relates to the aforementioned method and any of the attendant definitions, wherein said nucleophile is an alkyl or aryl or aralkyl 2-cyano-2-arylacetate.

In certain embodiments, the present invention relates to the aforementioned method and any of the attendant definitions, wherein said prochiral electron-deficient alkene or azo compound or prochiral aldehyde or prochiral ketone is a nitroalkene.

In certain embodiments, the present invention relates to the aforementioned method and any of the attendant definitions, wherein said prochiral electron-deficient alkene or azo compound or prochiral aldehyde or prochiral ketone is a dialkyl azodicarboxylate.

In certain embodiments, the present invention relates to the aforementioned method and any of the attendant definitions, wherein said prochiral electron-deficient alkene or azo compound or prochiral aldehyde or prochiral ketone is an alkenyl sulfone.

In certain embodiments, the present invention relates to the aforementioned method and any of the attendant definitions, wherein said prochiral electron-deficient alkene or azo compound or prochiral aldehyde or prochiral ketone is an alkenyl ketone.

In certain embodiments, the present invention relates to the aforementioned method and any of the attendant definitions, wherein said catalyst is present in less than about 70 mol % relative to said prochiral electron-deficient alkene or azo compound or prochiral aldehyde or prochiral ketone.

In certain embodiments, the present invention relates to the aforementioned method and any of the attendant definitions, wherein said catalyst is present in less than about 40 mol % relative to said prochiral electron-deficient alkene or azo compound or prochiral aldehyde or prochiral ketone.

In certain embodiments, the present invention relates to the aforementioned method and any of the attendant definitions, wherein said catalyst is present in less than about 10 mol % relative to said prochiral electron-deficient alkene or azo compound or prochiral aldehyde or prochiral ketone.

In certain embodiments, the present invention relates to the aforementioned method and any of the attendant definitions, wherein said catalyst is present in less than about 5 mol % relative to said prochiral electron-deficient alkene or azo compound or prochiral aldehyde or prochiral ketone.

In certain embodiments, the present invention relates to the aforementioned method and any of the attendant definitions, wherein said chiral, non-racemic compound has an enantiomeric excess greater than about 50%.

In certain embodiments, the present invention relates to the aforementioned method and any of the attendant definitions, wherein said chiral, non-racemic compound has an enantiomeric excess greater than about 70%.

In certain embodiments, the present invention relates to the aforementioned method and any of the attendant definitions, wherein said chiral, non-racemic compound has an enantiomeric excess greater than about 90%.

In certain embodiments, the present invention relates to the aforementioned method and any of the attendant definitions, wherein said chiral, non-racemic compound has an enantiomeric excess greater than about 95%.

In certain embodiments, the present invention relates to the aforementioned method and any of the attendant definitions, wherein R is H, aryl, or aralkyl; $R_1$ is alkyl or alkenyl; and said nucleophile is a malonate or a β-ketoester.

In certain embodiments, the present invention relates to the aforementioned method and any of the attendant definitions, wherein R is H; $R_1$ is alkyl or alkenyl; and said nucleophile is a malonate.

In certain embodiments, the present invention relates to the aforementioned method and any of the attendant definitions, wherein R is H; $R_1$ is —CH=$CH_2$; and said nucleophile is dimethyl malonate.

In certain embodiments, the present invention relates to the aforementioned method and any of the attendant definitions, wherein R is aryl; $R_1$ is alkyl or alkenyl; and said nucleophile is a malonate or β-ketoester.

In certain embodiments, the present invention relates to the aforementioned method and any of the attendant definitions, wherein R is phenanthrene; $R_1$ is —CH=$CH_2$; and said nucleophile is dimethyl malonate.

In certain embodiments, the present invention relates to the aforementioned method and any of the attendant definitions, wherein R is aralkyl; $R_1$ is alkyl or alkenyl; and said nucleophile is a malonate or β-ketoester.

In certain embodiments, the present invention relates to the aforementioned method and any of the attendant definitions, wherein R is benzyl; $R_1$ is —CH=$CH_2$; and said nucleophile is dimethyl malonate.

In certain embodiments, the present invention relates to the aforementioned method and any of the attendant definitions, wherein R is phenanthrene; $R_1$ is —CH=$CH_2$; and said nucleophile is a β-ketoester.

In certain embodiments, the present invention relates to the aforementioned method and any of the attendant definitions, wherein R is phenanthrene; $R_1$ is —CH=$CH_2$; and said nucleophile is an alkyl or aryl or aralkyl 2-cyano-2-alkylacetate In certain embodiments, the present invention relates to the aforementioned method and any of the attendant definitions, wherein R is phenanthrene; $R_1$ is —CH=CH$_2$; and said nucleophile is an alkyl or aryl or aralkyl 2-cyano-2-arylacetate.

Another aspect of the present invention relates to a method of preparing a chiral, non-racemic compound from a prochiral electron-deficient alkene or azo compound or prochiral aldehyde or prochiral ketone, comprising the step of:

reacting a prochiral electron-deficient alkene or azo compound or prochiral aldehyde or prochiral ketone with a nucleophile in the presence of a catalyst; thereby producing a chiral, non-racemic compound; wherein said catalyst is represented by formula II:

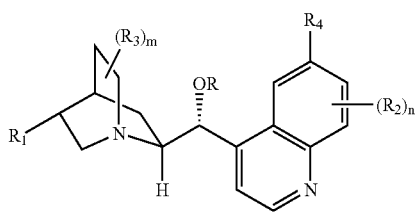

wherein, independently for each occurrence:

R represents H or a substituted or unsubstituted alkyl, alkenyl, alkynyl, aryl, aralkyl, heteroaryl, heteroaralkyl, heterocyclic, or heterocycloalkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$.

In certain embodiments, the present invention relates to the aforementioned method and any of the attendant definitions, wherein $R_4$ represents —OH.

In certain embodiments, the present invention relates to the aforementioned method and any of the attendant definitions, wherein R represents H, aryl, or aralkyl.

In certain embodiments, the present invention relates to the aforementioned method and any of the attendant definitions, wherein R represents H.

In certain embodiments, the present invention relates to the aforementioned method and any of the attendant definitions, wherein R represents aryl.

In certain embodiments, the present invention relates to the aforementioned method and any of the attendant definitions, wherein R represents phenanthrene.

In certain embodiments, the present invention relates to the aforementioned method and any of the attendant definitions, wherein R represents aralkyl.

In certain embodiments, the present invention relates to the aforementioned method and any of the attendant definitions, wherein R represents benzyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is H and $R_1$ is alkyl.

In certain embodiments, the present invention relates to the aforementioned method and any of the attendant definitions, wherein R is H and $R_1$ is ethyl.

In certain embodiments, the present invention relates to the aforementioned method and any of the attendant definitions, wherein R is H and $R_1$ is alkenyl.

In certain embodiments, the present invention relates to the aforementioned method and any of the attendant definitions, wherein R is H and $R_1$ is —CH=CH$_2$.

In certain embodiments, the present invention relates to the aforementioned method and any of the attendant definitions, wherein R is H, $R_1$ is alkyl, m is 0, and n is 0.

In certain embodiments, the present invention relates to the aforementioned method and any of the attendant definitions, wherein R is H, $R_1$ is ethyl, m is 0, and n is 0.

In certain embodiments, the present invention relates to the aforementioned method and any of the attendant definitions, wherein R is H, $R_1$ is alkenyl, m is 0, and n is 0.

In certain embodiments, the present invention relates to the aforementioned method and any of the attendant definitions, wherein R is H, $R_1$ is —CH=CH$_2$, m is 0, and n is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is phenanthrene and $R_1$ is alkyl.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is phenanthrene and $R_1$ is alkenyl.

In certain embodiments, the present invention relates to the aforementioned method and any of the attendant definitions, wherein R is phenanthrene and $R_1$ is —CH=CH$_2$.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is benzyl and $R_1$ is alkyl.

In certain embodiments, the present invention relates to the aforementioned method and any of the attendant definitions, wherein R is benzyl and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is benzyl and $R_1$ is alkenyl.

In certain embodiments, the present invention relates to the aforementioned method and any of the attendant definitions, wherein R is benzyl and $R_1$ is —CH=CH$_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is phenanthrene, $R_1$ is alkyl, m is 0, and n is 0.

In certain embodiments, the present invention relates to the aforementioned method and any of the attendant definitions, wherein R is phenanthrene, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is phenanthrene, $R_1$ is alkenyl, m is 0, and n is 0.

In certain embodiments, the present invention relates to the aforementioned method and any of the attendant definitions, wherein R is phenanthrene, $R_1$ is —CH=CH$_2$, m is 0, and n is 0.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is benzyl, $R_1$ is alkyl, m is 0, and n is 0.

In certain embodiments, the present invention relates to the aforementioned method and any of the attendant definitions, wherein R is benzyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is benzyl, $R_1$ is alkenyl, m is 0, and n is 0.

In certain embodiments, the present invention relates to the aforementioned method and any of the attendant definitions, wherein R is benzyl, $R_1$ is —CH=CH$_2$, m is 0, and n is 0.

In certain embodiments, the present invention relates to the aforementioned method and any of the attendant definitions, wherein said nucleophile is a secondary or tertiary nucleophile.

In certain embodiments, the present invention relates to the aforementioned method and any of the attendant definitions, wherein said nucleophile is a secondary nucleophile.

In certain embodiments, the present invention relates to the aforementioned method and any of the attendant definitions, wherein said nucleophile is a tertiary nucleophile.

In certain embodiments, the present invention relates to the aforementioned method and any of the attendant definitions, wherein said nucleophile is a malonate or a β-ketoester.

In certain embodiments, the present invention relates to the aforementioned method and any of the attendant definitions, wherein said nucleophile is dimethyl malonate.

In certain embodiments, the present invention relates to the aforementioned method and any of the attendant definitions, wherein said nucleophile is an alkyl or aryl or aralkyl 2-cyano-2-alkylacetate.

In certain embodiments, the present invention relates to the aforementioned method and any of the attendant definitions, wherein said nucleophile is an alkyl or aryl or aralkyl 2-cyano-2-arylacetate.

In certain embodiments, the present invention relates to the aforementioned method and any of the attendant definitions, wherein said prochiral electron-deficient alkene or azo compound or prochiral aldehyde or prochiral ketone is a nitroalkene.

In certain embodiments, the present invention relates to the aforementioned method and any of the attendant definitions, wherein said prochiral electron-deficient alkene or azo compound or prochiral aldehyde or prochiral ketone is a dialkyl azodicarboxylate.

In certain embodiments, the present invention relates to the aforementioned method and any of the attendant definitions, wherein said prochiral electron-deficient alkene or azo compound or prochiral aldehyde or prochiral ketone is an alkenyl sulfone.

In certain embodiments, the present invention relates to the aforementioned method and any of the attendant definitions, wherein said prochiral electron-deficient alkene or azo compound or prochiral aldehyde or prochiral ketone is an alkenyl ketone.

In certain embodiments, the present invention relates to the aforementioned method and any of the attendant definitions, wherein said catalyst is present in less than about 70 mol % relative to said prochiral electron-deficient alkene or azo compound or prochiral aldehyde or prochiral ketone.

In certain embodiments, the present invention relates to the aforementioned method and any of the attendant definitions, wherein said catalyst is present in less than about 40 mol % relative to said prochiral electron-deficient alkene or azo compound or prochiral aldehyde or prochiral ketone.

In certain embodiments, the present invention relates to the aforementioned method and any of the attendant definitions, wherein said catalyst is present in less than about 10 mol % relative to said prochiral electron-deficient alkene or azo compound or prochiral aldehyde or prochiral ketone.

In certain embodiments, the present invention relates to the aforementioned method and any of the attendant definitions, wherein said catalyst is present in less than about 5 mol % relative to said prochiral electron-deficient alkene or azo compound or prochiral aldehyde or prochiral ketone.

In certain embodiments, the present invention relates to the aforementioned method and any of the attendant definitions, wherein said chiral, non-racemic compound has an enantiomeric excess greater than about 50%.

In certain embodiments, the present invention relates to the aforementioned method and any of the attendant definitions, wherein said chiral, non-racemic compound has an enantiomeric excess greater than about 70%.

In certain embodiments, the present invention relates to the aforementioned method and any of the attendant definitions, wherein said chiral, non-racemic compound has an enantiomeric excess greater than about 90%.

In certain embodiments, the present invention relates to the aforementioned method and any of the attendant definitions, wherein said chiral, non-racemic compound has an enantiomeric excess greater than about 95%.

In certain embodiments, the present invention relates to the aforementioned method and any of the attendant definitions, wherein R is H, aryl, or aralkyl; $R_1$ is alkyl or alkenyl; and said nucleophile is a malonate or β-ketoester.

In certain embodiments, the present invention relates to the aforementioned method and any of the attendant definitions, wherein R is H; $R_1$ is alkyl or alkenyl; and said nucleophile is a malonate or β-ketoester.

In certain embodiments, the present invention relates to the aforementioned method and any of the attendant definitions, wherein R is H; $R_1$ is —CH=CH$_2$; and said nucleophile is dimethyl malonate.

In certain embodiments, the present invention relates to the aforementioned method and any of the attendant definitions, wherein R is aryl; $R_1$ is alkyl or alkenyl; and said nucleophile is a malonate or β-ketoester.

In certain embodiments, the present invention relates to the aforementioned method and any of the attendant definitions, wherein R is phenanthrene; $R_1$ is —CH=CH$_2$; and said nucleophile is dimethyl malonate.

In certain embodiments, the present invention relates to the aforementioned method and any of the attendant definitions, wherein R is aralkyl; $R_1$ is alkyl or alkenyl; and said nucleophile is a malonate or β-ketoester.

In certain embodiments, the present invention relates to the aforementioned method and any of the attendant definitions, wherein R is benzyl; $R_1$ is —CH=CH$_2$; and said nucleophile is dimethyl malonate.

In certain embodiments, the present invention relates to the aforementioned method and any of the attendant definitions, wherein R is phenanthrene; $R_1$ is —CH=CH$_2$; and said nucleophile is β-ketoester.

In certain embodiments, the present invention relates to the aforementioned method and any of the attendant definitions, wherein R is phenanthrene; $R_1$ is —CH=CH$_2$; and said nucleophile is an alkyl or aryl or aralkyl 2-cyano-2-alkylacetate.

In certain embodiments, the present invention relates to the aforementioned method and any of the attendant definitions, wherein R is phenanthrene; $R_1$ is —CH=CH$_2$; and said nucleophile is an alkyl or aryl or aralkyl 2-cyano-2-arylacetate.

Methods of Invention—Kinetic Resolution

In another aspect of the present invention, kinetic resolution of enantiomers occurs by catalysis, using a subject chiral catalyst, of the transformation of a racemic substrate. In the subject kinetic resolution processes for a racemic substrate, one enantiomer can be recovered as unreacted substrate while the other is transformed to the desired product. Of course, it will be appreciated that the kinetic resolution can be performed by removing the undesired enantiomer by reaction with a nucleophile, and recovering the desired enantiomer unchanged from the reaction mixture. One significant advantage of this approach is the ability to use inexpensive racemic starting materials rather than the expensive, enantiomerically pure starting compounds. In certain embodiments, the subject catalysts may be used in kinetic resolutions of racemic substrates comprising a double bond.

One aspect of the present invention relates to a method of kinetic resolution, comprising the step of:

reacting a racemic substrate comprising a double bond with a nucleophile in the presence of a catalyst represented by formula I:

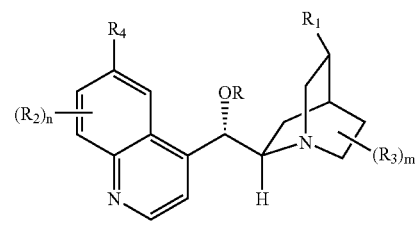

wherein, independently for each occurrence:

R represents H or a substituted or unsubstituted alkyl, alkenyl, alkynyl, aryl, aralkyl, heteroaryl, heteroaralkyl, heterocyclic, or heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —NH$_2$, —NHR$_2$—NH(C=O)NR$_2$R$_3$, —NH(SO$_2$)R$_2$, —NH(C=O)OR$_2$, or —NH(C=O)R$_2$.

In certain embodiments, the present invention relates to the aforementioned method wherein $R_4$ represents —OH.

In certain embodiments, the present invention relates to the aforementioned method and any of the attendant definitions, wherein R represents H, aryl, or aralkyl.

In certain embodiments, the present invention relates to the aforementioned method and any of the attendant definitions, wherein R represents H.

In certain embodiments, the present invention relates to the aforementioned method and any of the attendant definitions, wherein R represents aryl.

In certain embodiments, the present invention relates to the aforementioned method and any of the attendant definitions, wherein R represents phenanthrene.

In certain embodiments, the present invention relates to the aforementioned method and any of the attendant definitions, wherein R represents aralkyl.

In certain embodiments, the present invention relates to the aforementioned method and any of the attendant definitions, wherein R represents benzyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=CH$_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is H and $R_1$ is alkyl.

In certain embodiments, the present invention relates to the aforementioned method and any of the attendant definitions, wherein R is H and $R_1$ is ethyl.

In certain embodiments, the present invention relates to the aforementioned method and any of the attendant definitions, wherein R is H and $R_1$ is alkenyl.

In certain embodiments, the present invention relates to the aforementioned method and any of the attendant definitions, wherein R is H and $R_1$ is —CH=$CH_2$.

In certain embodiments, the present invention relates to the aforementioned method and any of the attendant definitions, wherein R is H, $R_1$ is alkyl, m is 0, and n is 0.

In certain embodiments, the present invention relates to the aforementioned method and any of the attendant definitions, wherein R is H, $R_1$ is ethyl, m is 0, and n is 0.

In certain embodiments, the present invention relates to the aforementioned method and any of the attendant definitions, wherein R is H, $R_1$ is alkenyl, m is 0, and n is 0.

In certain embodiments, the present invention relates to the aforementioned method and any of the attendant definitions, wherein R is H, $R_1$ is —CH=$CH_2$, m is 0, and n is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is phenanthrene and $R_1$ is alkyl.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is phenanthrene and $R_1$ is alkenyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is benzyl and $R_1$ is alkyl.

In certain embodiments, the present invention relates to the aforementioned method and any of the attendant definitions, wherein R is benzyl and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is benzyl and $R_2$ is alkenyl.

In certain embodiments, the present invention relates to the aforementioned method and any of the attendant definitions, wherein R is benzyl and $R_1$ is —CH=$CH_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is phenanthrene, $R_1$ is alkyl, m is 0, and n is 0.

In certain embodiments, the present invention relates to the aforementioned method and any of the attendant definitions, wherein R is phenanthrene, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is phenanthrene, $R_1$ is alkenyl, m is 0, and n is 0.

In certain embodiments, the present invention relates to the aforementioned method and any of the attendant definitions, wherein R is phenanthrene, $R_1$ is —CH=$CH_2$, m is 0, and n is 0.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is benzyl, $R_1$ is alkyl, m is 0, and n is 0.

In certain embodiments, the present invention relates to the aforementioned method and any of the attendant definitions, wherein R is benzyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is benzyl, $R_1$ is alkenyl, m is 0, and n is 0.

In certain embodiments, the present invention relates to the aforementioned method and any of the attendant definitions, wherein R is benzyl, $R_1$ is —CH=$CH_2$, m is 0, and n is 0.

In certain embodiments, the present invention relates to the aforementioned method and any of the attendant definitions, wherein said nucleophile is a secondary or tertiary nucleophile.

In certain embodiments, the present invention relates to the aforementioned method and any of the attendant definitions, wherein said nucleophile is a secondary nucleophile.

In certain embodiments, the present invention relates to the aforementioned method and any of the attendant definitions, wherein said nucleophile is a tertiary nucleophile.

In certain embodiments, the present invention relates to the aforementioned method and any of the attendant definitions, wherein said nucleophile is a malonate or a β-ketoester.

In certain embodiments, the present invention relates to the aforementioned method and any of the attendant definitions, wherein said nucleophile is dimethyl malonate.

In certain embodiments, the present invention relates to the aforementioned method and any of the attendant definitions, wherein said nucleophile is a β-ketoester.

In certain embodiments, the present invention relates to the aforementioned method and any of the attendant definitions, wherein said nucleophile is an alkyl or aryl or aralkyl 2-cyano-2-alkylacetate.

In certain embodiments, the present invention relates to the aforementioned method and any of the attendant definitions, wherein said nucleophile is an alkyl or aryl or aralkyl 2-cyano-2-arylacetate.

In certain embodiments, the present invention relates to the aforementioned method and any of the attendant definitions, wherein R is H, aryl, or aralkyl; $R_1$ is alkyl or alkenyl; and said nucleophile is a malonate or β-ketoester.

In certain embodiments, the present invention relates to the aforementioned method and any of the attendant definitions, wherein R is H; $R_1$ is alkyl or alkenyl; and said nucleophile is a malonate or β-ketoester.

In certain embodiments, the present invention relates to the aforementioned method and any of the attendant definitions, wherein R is H; $R_1$ is —CH=$CH_2$; and said nucleophile is dimethyl malonate.

In certain embodiments, the present invention relates to the aforementioned method and any of the attendant definitions, wherein R is aryl; $R_1$ is alkyl or alkenyl; and said nucleophile is a malonate or β-ketoester.

In certain embodiments, the present invention relates to the aforementioned method and any of the attendant definitions, wherein R is phenanthrene; $R_1$ is —CH=$CH_2$; and said nucleophile is dimethyl malonate.

In certain embodiments, the present invention relates to the aforementioned method and any of the attendant definitions, wherein R is aralkyl; $R_1$ is alkyl or alkenyl; and said nucleophile is a malonate or β-ketoester.

In certain embodiments, the present invention relates to the aforementioned method and any of the attendant definitions, wherein R is benzyl; $R_1$ is —CH=$CH_2$; and said nucleophile is dimethyl malonate.

In certain embodiments, the present invention relates to the aforementioned method and any of the attendant definitions, wherein R is phenanthrene; $R_1$ is —CH=$CH_2$; and said nucleophile is a β-ketoester.

In certain embodiments, the present invention relates to the aforementioned method and any of the attendant definitions, wherein R is phenanthrene; $R_1$ is —CH=$CH_2$; and said nucleophile is an alkyl or aryl or aralkyl 2-cyano-2-alkylacetate.

In certain embodiments, the present invention relates to the aforementioned method and any of the attendant definitions, wherein R is phenanthrene; $R_1$ is —CH=$CH_2$; and said nucleophile is an alkyl or aryl or aralkyl 2-cyano-2-arylacetate.

Another aspect of the present invention relates to a method of kinetic resolution, comprising the step of:

reacting a racemic substrate comprising a double bond with a nucleophile in the presence of a catalyst represented by formula II:

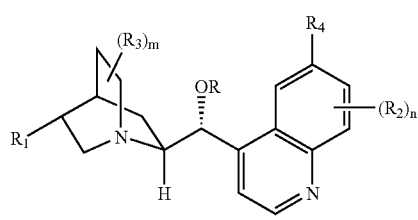

II wherein, wherein independently for each occurrence:

R represents H or a substituted or unsubstituted alkyl, alkenyl, alkynyl, aryl, aralkyl, heteroaryl, heteroaralkyl, heterocyclic, or heterocycloalkyl;

$R_1$ represents a substituted or unsubstituted alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents —OH, —OTf, —ONf, —SH, —$NH_2$, —$NHR_2$—NH(C=O)$NR_2R_3$, —NH($SO_2$)$R_2$, —NH(C=O)$OR_2$, or —NH(C=O)$R_2$.

In certain embodiments, the present invention relates to the aforementioned method and any of the attendant definitions, wherein $R_4$ represents —OH.

In certain embodiments, the present invention relates to the aforementioned method and any of the attendant definitions, wherein R represents H, aryl, or aralkyl.

In certain embodiments, the present invention relates to the aforementioned method and any of the attendant definitions, wherein R represents H.

In certain embodiments, the present invention relates to the aforementioned method and any of the attendant definitions, wherein R represents aryl.

In certain embodiments, the present invention relates to the aforementioned method and any of the attendant definitions, wherein R represents phenanthrene.

In certain embodiments, the present invention relates to the aforementioned method and any of the attendant definitions, wherein R represents aralkyl.

In certain embodiments, the present invention relates to the aforementioned method and any of the attendant definitions, wherein R represents benzyl.

In certain embodiments, the present invention relates to the aforementioned method and any of the attendant definitions, wherein $R_1$ is alkyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is alkenyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is H and $R_1$ is alkyl.

In certain embodiments, the present invention relates to the aforementioned method and any of the attendant definitions, wherein R is H and $R_1$ is ethyl.

In certain embodiments, the present invention relates to the aforementioned method and any of the attendant definitions, wherein R is H and $R_1$ is alkenyl.

In certain embodiments, the present invention relates to the aforementioned method and any of the attendant definitions, wherein R is H and $R_1$ is —CH=$CH_2$.

In certain embodiments, the present invention relates to the aforementioned method and any of the attendant definitions, wherein R is H, $R_1$ is alkyl, m is 0, and n is 0.

In certain embodiments, the present invention relates to the aforementioned method and any of the attendant definitions, wherein R is H, $R_1$ is ethyl, m is 0, and n is 0.

In certain embodiments, the present invention relates to the aforementioned method and any of the attendant definitions, wherein R is H, $R_1$ is alkenyl, m is 0, and n is 0.

In certain embodiments, the present invention relates to the aforementioned method and any of the attendant definitions, wherein R is H, $R_1$ is —CH=$CH_2$, m is 0, and n is 0.

In certain embodiments, the present invention relates to the aforementioned method and any of the attendant definitions, wherein R is aryl and $R_1$ is alkyl.

In certain embodiments, the present invention relates to the aforementioned method and any of the attendant definitions, wherein R is phenanthrene and $R_1$ is alkyl.

In certain embodiments, the present invention relates to the aforementioned method and any of the attendant definitions, wherein R is phenanthrene and $R_1$ is ethyl.

In certain embodiments, the present invention relates to the aforementioned method and any of the attendant definitions, wherein R is aryl and $R_1$ is alkenyl.

In certain embodiments, the present invention relates to the aforementioned method and any of the attendant definitions, wherein R is phenanthrene and $R_1$ is alkenyl.

In certain embodiments, the present invention relates to the aforementioned method and any of the attendant definitions, wherein R is phenanthrene and $R_1$ is —CH=$CH_2$.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is benzyl and $R_1$ is alkyl.

In certain embodiments, the present invention relates to the aforementioned method and any of the attendant definitions, wherein R is benzyl and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is benzyl and $R_2$ is alkenyl.

In certain embodiments, the present invention relates to the aforementioned method and any of the attendant definitions, wherein R is benzyl and $R_1$ is —CH=$CH_2$.

In certain embodiments, the present invention relates to the aforementioned method and any of the attendant definitions, wherein R is aryl, $R_1$ is alkyl, m is 0, and n is 0.

In certain embodiments, the present invention relates to the aforementioned method and any of the attendant definitions, wherein R is phenanthrene, $R_1$ is alkyl, m is 0, and n is 0.

In certain embodiments, the present invention relates to the aforementioned method and any of the attendant definitions, wherein R is phenanthrene, $R_1$ is ethyl, m is 0, and n is 0.

In certain embodiments, the present invention relates to the aforementioned method and any of the attendant definitions, wherein R is aryl, $R_1$ is alkenyl, m is 0, and n is 0.

In certain embodiments, the present invention relates to the aforementioned method and any of the attendant definitions, wherein R is phenanthrene, $R_1$ is alkenyl, m is 0, and n is 0.

In certain embodiments, the present invention relates to the aforementioned method and any of the attendant definitions, wherein R is phenanthrene, $R_1$ is —CH=$CH_2$, m is 0, and n is 0.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is benzyl, $R_1$ is alkyl, m is 0, and n is 0.

In certain embodiments, the present invention relates to the aforementioned method and any of the attendant definitions, wherein R is benzyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is benzyl, $R_1$ is alkenyl, m is 0, and n is 0.

In certain embodiments, the present invention relates to the aforementioned method and any of the attendant definitions, wherein R is benzyl, $R_1$ is —CH=$CH_2$, m is 0, and n is 0.

In certain embodiments, the present invention relates to the aforementioned method and any of the attendant definitions, wherein said nucleophile is a secondary or tertiary nucleophile.

In certain embodiments, the present invention relates to the aforementioned method and any of the attendant definitions, wherein said nucleophile is a secondary nucleophile.

In certain embodiments, the present invention relates to the aforementioned method and any of the attendant definitions, wherein said nucleophile is a tertiary nucleophile.

In certain embodiments, the present invention relates to the aforementioned method and any of the attendant definitions, wherein said nucleophile is a malonate or a β-ketoester.

In certain embodiments, the present invention relates to the aforementioned method and any of the attendant definitions, wherein said nucleophile is dimethyl malonate.

In certain embodiments, the present invention relates to the aforementioned method and any of the attendant definitions, wherein said nucleophile is a β-ketoester.

In certain embodiments, the present invention relates to the aforementioned method and any of the attendant definitions, wherein said nucleophile is an alkyl or aryl or aralkyl 2-cyano-2-alkylacetate.

In certain embodiments, the present invention relates to the aforementioned method and any of the attendant definitions, wherein said nucleophile is an alkyl or aryl or aralkyl 2-cyano-2-arylacetate.

In certain embodiments, the present invention relates to the aforementioned method and any of the attendant definitions, wherein R is H, aryl, or aralkyl; $R_1$ is alkyl or alkenyl; and said nucleophile is a malonate or β-ketoester.

In certain embodiments, the present invention relates to the aforementioned method and any of the attendant definitions, wherein R is H; $R_1$ is alkyl or alkenyl; and said nucleophile is a malonate.

In certain embodiments, the present invention relates to the aforementioned method and any of the attendant definitions, wherein R is H; $R_1$ is —CH=$CH_2$; and said nucleophile is dimethyl malonate.

In certain embodiments, the present invention relates to the aforementioned method and any of the attendant definitions, wherein R is aryl; $R_1$ is alkyl or alkenyl; and said nucleophile is a malonate or β-ketoester.

In certain embodiments, the present invention relates to the aforementioned method and any of the attendant definitions, wherein R is phenanthrene; $R_1$ is —CH=CH$_2$; and said nucleophile is dimethyl malonate.

In certain embodiments, the present invention relates to the aforementioned method and any of the attendant definitions, wherein R is aralkyl; $R_1$ is alkyl or alkenyl; and said nucleophile is a malonate or β-ketoester.

In certain embodiments, the present invention relates to the aforementioned method and any of the attendant definitions, wherein R is benzyl; $R_1$ is —CH=CH$_2$; and said nucleophile is dimethyl malonate.

In certain embodiments, the present invention relates to the aforementioned method and any of the attendant definitions, wherein R is phenanthrene; $R_1$ is —CH=CH$_2$; and said nucleophile is a β-ketoester.

In certain embodiments, the present invention relates to the aforementioned method and any of the attendant definitions, wherein R is phenanthrene; $R_1$ is —CH=CH$_2$; and said nucleophile is an alkyl or aryl or aralkyl 2-cyano-2-alkylacetate.

In certain embodiments, the present invention relates to the aforementioned method and any of the attendant definitions, wherein R is phenanthrene; $R_1$ is —CH=CH$_2$; and said nucleophile is alkyl or aryl or aralkyl 2-cyano-2-arylacetate.

Nucleophiles

Nucleophiles which are useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of reactants and conditions—in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art. For nucleophiles which exist as anions, the counterion can be any of a variety of conventional cations, including alkali and alkaline earth metal cations and ammonium cations. In certain embodiments, the nucleophile may be part of the substrate, thus resulting in an intramolecular reaction.

The nucleophile may be a primary (eq. 1), secondary (eq. 2), or tertiary (eq. 3) nucleophile as depicted below in Scheme 4.

Scheme 4

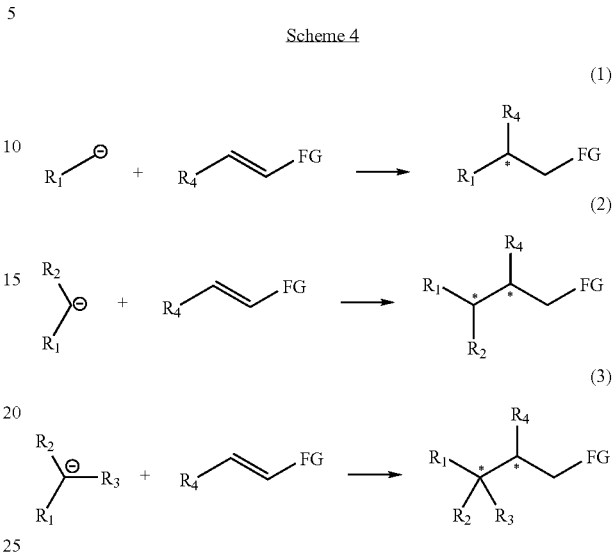

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain at least one reactive electrophilic center or moiety with distinct stereogenic faces; or at least two electrophilic moieties related by an internal plane or point of symmetry at which a nucleophile may attack with the assistance of the catalyst. The catalyzed, stereoselective attack of the nucleophile at the electrophilic center will produce a chiral non-racemic product. Most of the substrates contemplated for use in the methods of the present invention contain at least one double bond. The alkene in some embodiments will comprise an electron withdrawing group making the double bond more susceptible to nucleophilic attack. Examples of suitable alkene substrates which are susceptible to nucleophilic attack by the subject method include nitroalkenes, dialkyl azodicarboxylates, alkenyl sulfones, alkenyl ketones and the like.

In preferred embodiments, the alkene is a prochiral or meso compound. In other embodiments, the alkene will be a chiral compound. In certain embodiments, the substrate will be a racemic mixture. In certain embodiments, the substrate will be a mixture of diastereomers. In certain embodiments, the methods of the present invention effect a kinetic resolution. In certain embodiments, the methods of the present invention effect a dynamic kinetic resolution. In certain embodiments, the electron withdrawing group may be a nitro group, a sulfonyl, a ketone, or a carboxylate.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

Enantioselective Conjugate Addition

Adjacent quaternary and tertiary stereocenters are common structural motifs in complex natural products. In principle, a stereocontrolled conjugate addition of a prochiral trisubstituted or disubstituted carbon nucleophile to a prochiral β-substituted Michael acceptor with a chiral catalyst could provide a one-step construction of such highly congested motifs from simple precursors (see eq. 1 and 2 in Scheme 4). However, this requires the catalyst to impart both high enantioselectivity and diastereoselectivity in a sterically demanding, intermolecular C—C bond formation that simultaneously creates both the quaternary and tertiary stereocenters. This task has proven to be a formidable challenge. Among numerous literature examples, the chiral salen-Al complex mediated addition of substituted cyanoacetates to α,β-unsaturated imides may represent the only catalytic asymmetric conjugate addition that affords the 1,4-adducts containing adjacent quaternary and tertiary stereocenters in excellent ee and greater than 10/1 diastereomer ratio (dr) for a substantial number of trisubstituted carbon Michael donors. For reviews see: (a) Sibi, M. P.; Manyem, S. *Tetrahedron* 2000, 56, 8033; (b) Krause, N.; Hoffmann-Roder, A. *Synthesis* 2001, 171; (c) Berner, O. M.; Tedeschi, L.; Enders, D. *Eur. J. Org. Chem.* 2002, 1877. (d) Christoffers, J.; Baro, A. *Angew. Chem. Int. Ed.* 2003, 42, 1688; (e) Yamaguchi, M. In *Comprehensive Asymmetric Catalysis*; Jacobsen, E. N.; Pfaltz, A., Yamamoto, H, Eds.; Springer: Supplement 1; Supplement to Chapter 31.2, 151. Taylor, M. S.; Jacobsen, E. N. *J. Am. Chem. Soc.* 2003, 125, 11204. For other notable studies of intermolecular, diastereoselective and enantioselective catalytic conjugate additions for the construction of vicinal quaternary-tertiary stereocenters see: a) Hamashima, Y.; Hotta, D.; Sodeoka, M. *J. Am. Chem. Soc.* 2002, 124, 11240. b) Mase, M.; Thayumanavan, R.; Tanaka, F.; Barbas, C. F. *Org. Lett.* 2004, 6, 2527-2530.

Cinchona Alkaloid Catalyst

Figure 2:
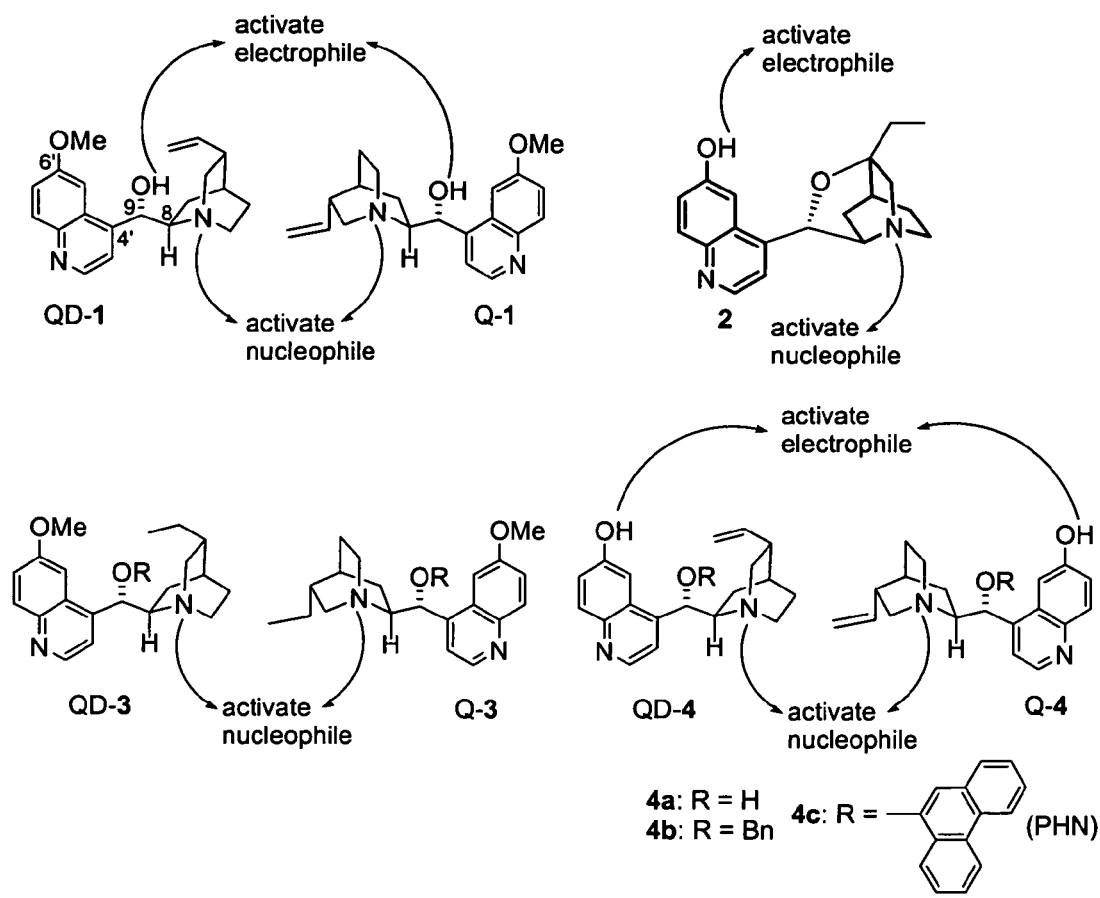
FIG. 2 depicts the bifunctional nature of several cinchona-alkaloid-based catalysts of the present invention.
Figure 3:
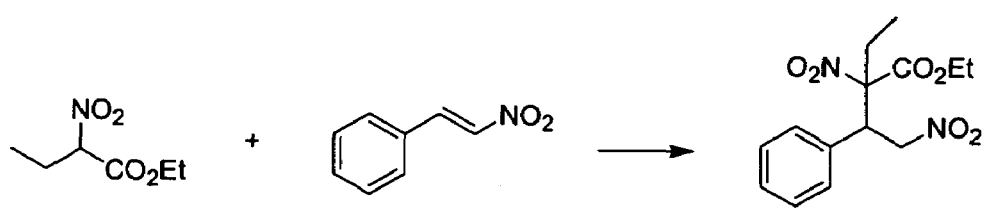
FIG. 3 depicts the results of several asymmetric Michael additions of the present invention.
Figure 3:
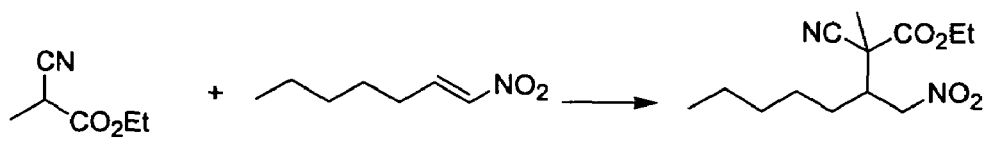
Figure 3:
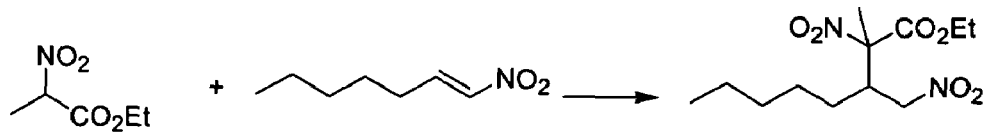
Figure 4:
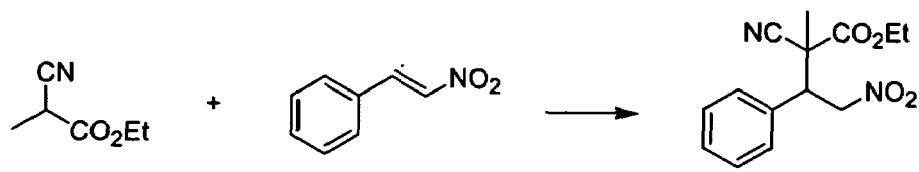
FIG. 4 depicts the results of several asymmetric Michael additions of the present invention.
Figure 4:
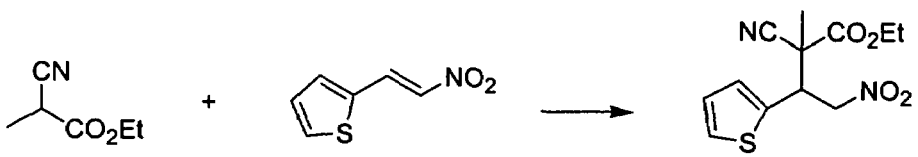
Figure 4:
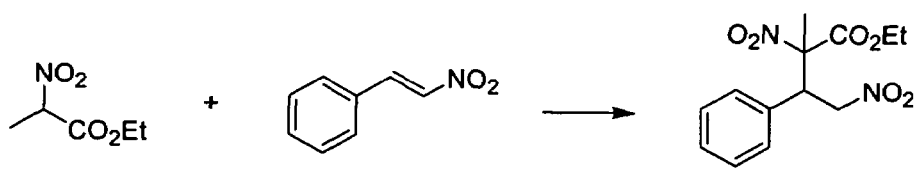
Figure 4:
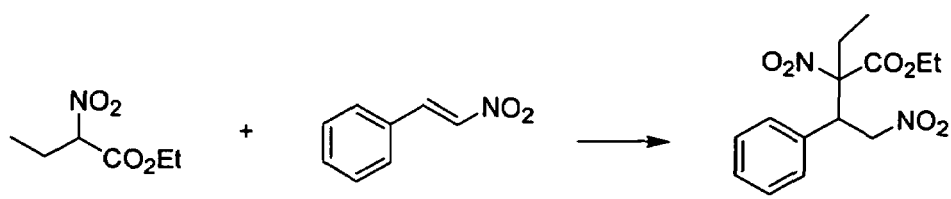
Figure 5:
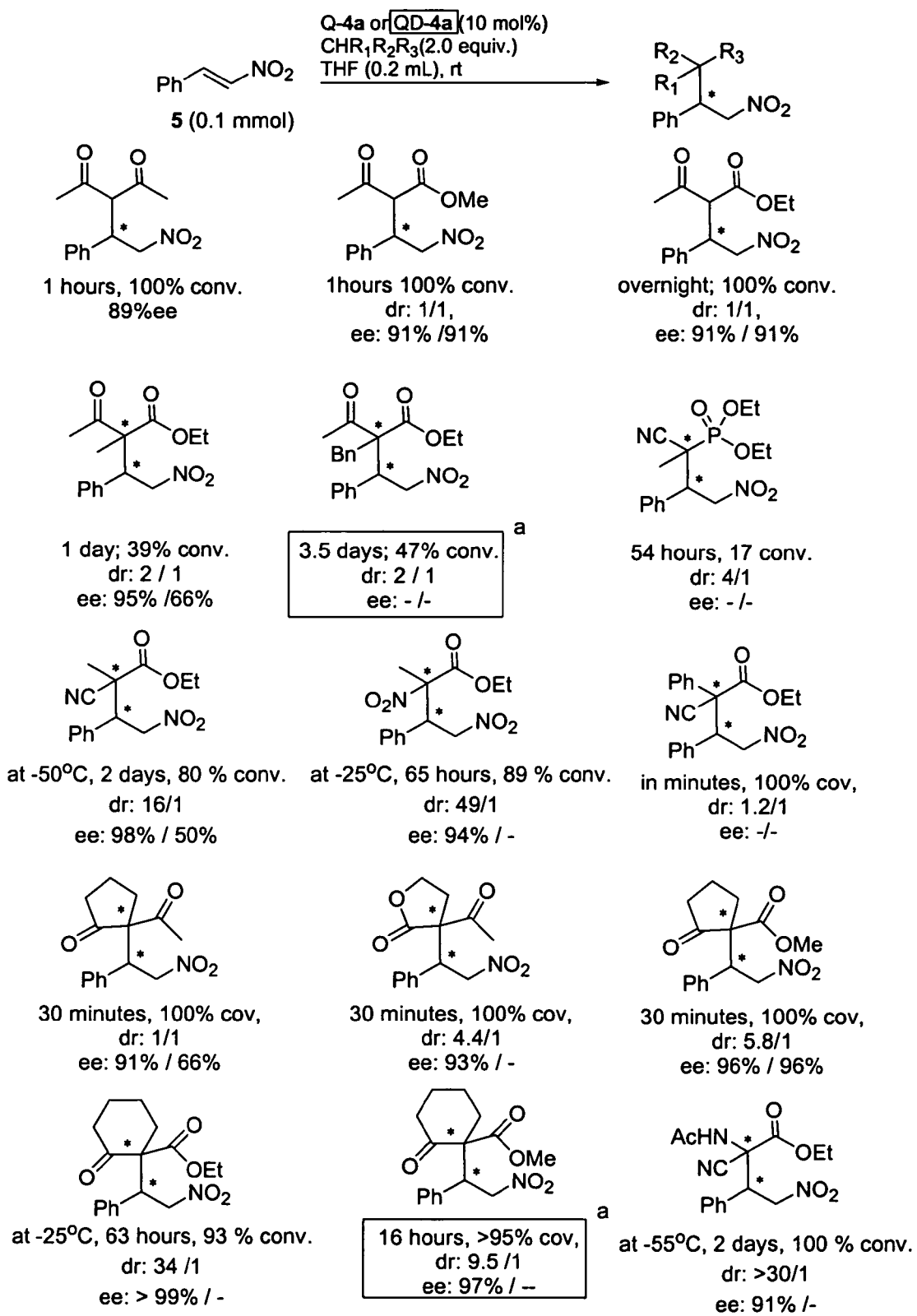
FIG. 5 depicts the results of several asymmetric Michael additions of the present invention.
Figure 6:
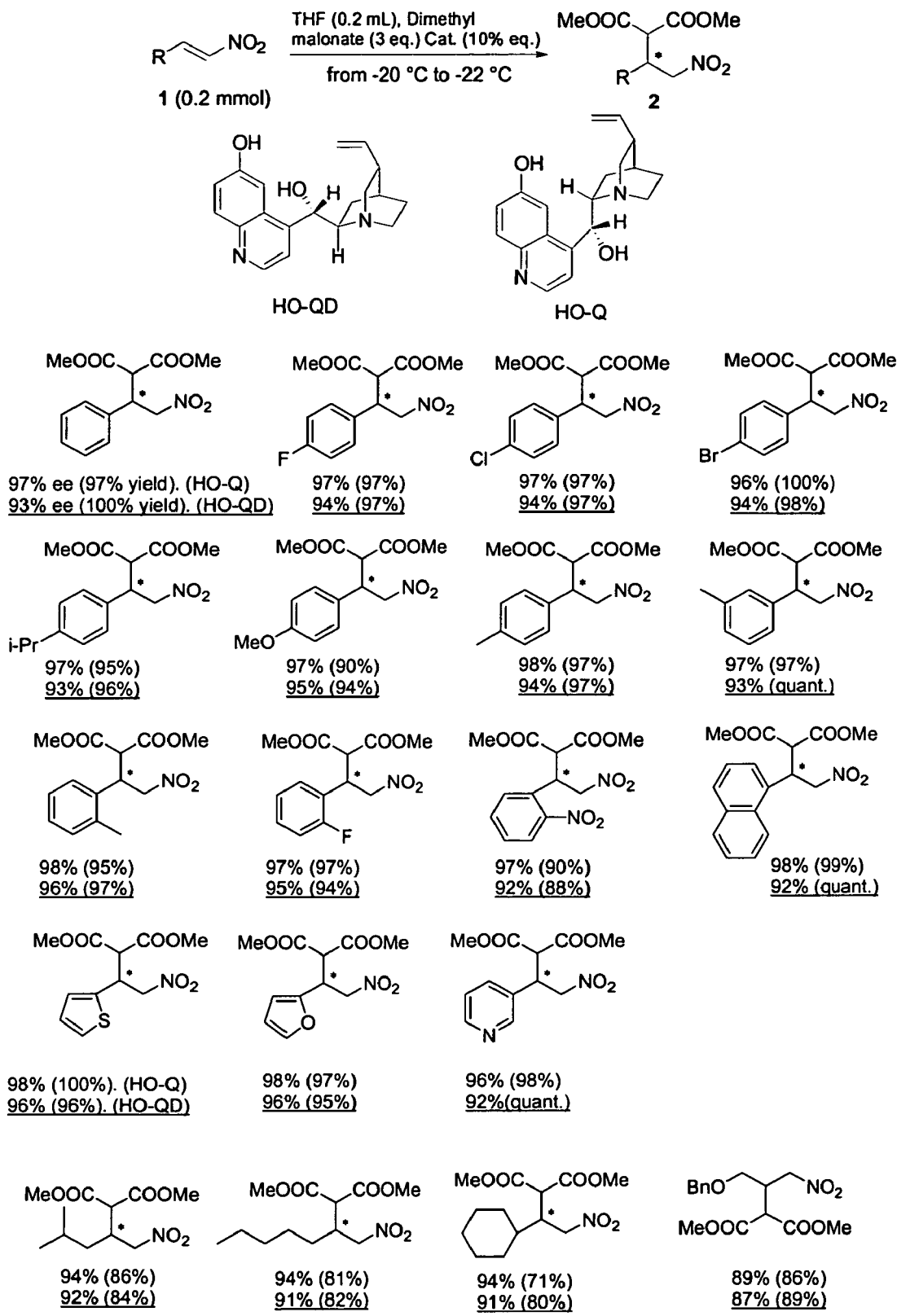
FIG. 6 depicts the results of several asymmetric Michael additions of the present invention.
Figure 7:
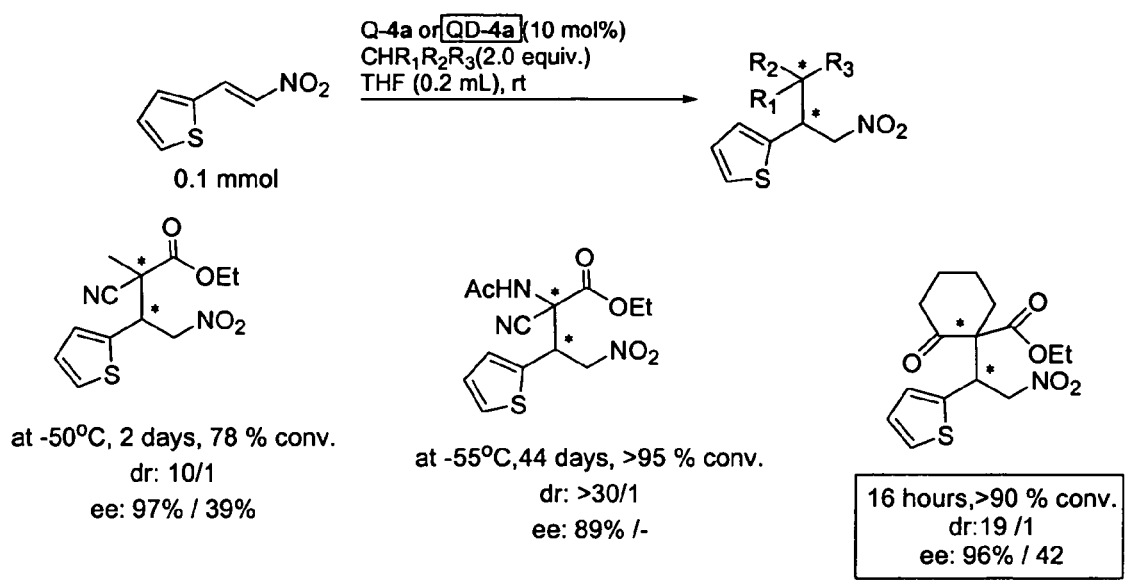
FIG. 7 depicts the results of several asymmetric Michael additions of the present invention.

With a cage-like structure that prevents rotation of the C8-C9 bond catalyst 2 is conformationally rigid, a common feature of many efficient chiral catalysts or ligands (see FIG. 2). However, recent extensive studies of asymmetric organic catalysis of C9-OH modified cinchona alkaloids demonstrated that cinchona alkaloids with rotational freedom around C8-C9 and C4'-C9 bonds are broadly effective organic catalysts (FIG. 1, compounds QD-1, Q-1, QD-3, and QD-3). Following this observation with an interest of developing efficient bifunctional chiral organic catalysts, we became interested in the asymmetric catalysis of cinchona alkaloids with a general structure portrayed as 4 (FIG. 2). Although previously not shown to be an effective catalyst for any asymmetric reaction, cinchona alkaloids 4 (QD-4 and Q-4) are easily accessible from both quinine and quinidine. Therefore they could serve as bifunctional chiral catalysts that provide straightforward access to either enantiomer of a given chiral product. Furthermore, with an easily tunable C9-OR group, 4 are more amenable than 1 or 2 towards modifications for optimizations of catalyst activity and selectivity.

Our investigations began with the preparation of catalysts QD-4a-c, from natural or commercially available modified cinchona alkaloids via high yielding and experimentally simple one or two-step protocols. These catalysts and other readily accessible natural and modified cinchona alkaloids were then examined for their ability to mediate enantioselective 1,4-addition of malonates to nitroalkenes, a synthetically important C—C bond forming reaction employing readily available starting materials. Although high enantioselectivity for this 1,4-addition is achieved with chiral Mg-bis(oxazoline) complexes and bifunctional organic catalysts derived from chiral 1,2-diaminocyclohexane, there is substantial room for improvement in terms of both enantioselectivity and substrate scope.

Reaction of Cinchona Alkaloid Catalysts with Secondary Nucleophiles

Presented in Table 1 are results obtained from addition of methyl and ethyl malonate to nitroalkene 5a mediated by various cinchona alkaloids in THF.

TABLE 1

Asymmetric 1,4-Addition of Malonates to trans-Phenyl Nitroatkene (5a)[a].

| Entry | Cat. | R | T/° C. | % Conv. | % ee |
|---|---|---|---|---|---|
| 1 | QD | Et | 23 | 78 | 16 |
| 2 | DHQD-PHN | Et | 23 | 28 | 6 |
| 3 | DHQD-CLB | Et | 23 | 10 | 12 |
| 4 | (DHQD)$_2$AQN | Et | 23 | 38 | 18 |
| 5 | (DHQD)$_2$PYR | Et | 23 | 46 | 24 |
| 6 | (DHQD)$_2$PHAL | Et | 23 | 18 | 13 |
| 7 | 2 | Et | 23 | 90 | 75 |
| 8 | QD-4a | Et | 23 | >98 | 79 |
| 9 | QD-4b | Et | 23 | 91 | 78 |
| 10 | QD-4c | Et | 23 | 84 | 82 |
| 11 | 2 | Et[b] | −20 | 75 | 86 |
| 12 | QD-4a | Et[b] | −20 | 86 | 90 |
| 13 | QD-4b | Et[b] | −20 | 90 | 88 |
| 14 | QD-4c | Et[b] | −20 | 73 | 91 |
| 15 | QD-4a | Me[c] | −20 | >98 | 93 |
| 16 | Q-4a | Me[c] | −20 | >98 | 96 |
| 17 | QD-4a | Me[d] | −55 | 81 | 97 |
| 18 | Q-4a | Me[d] | −55 | 93 | 99 |

[a]Unless noted, reactions were run with 0.1 mmol of 4 at r.t. for 12 h.
[b]Reaction was run for 36 h.
[c]Reaction was run for 36 h using 3.0 equiv. CH$_2$(CO$_2$Me)$_2$.
[d]Reaction was run for 108 h.

Cinchona alkaloids bearing a C6'-OH (2 and 4) were found to afford significantly higher enantioselectivity and faster rate than those bearing a C6'-OMe (entries 7-10 vs. 1-6). Catalysts QD-4a-c, although conformationally unlocked, afforded higher enantioselectivity than 2 did. Interestingly, the structurally most simple and practically most accessible cinchona alkaloid bearing a C6'-OH, QD-4a, was found to be a highly efficient catalyst in spite of possessing two hydrogen-bond donors. While excellent enantioselectivity can be achieved with ethyl malonate with either catalyst 4a or 4c at −20° C., the addition of methyl malonate with 4a under the same condition proceeded in faster rate and higher enantioselectivity (entries 13-15). Importantly, Q-4a afforded even higher enantioselectivity with an opposite sense of asymmetric induction (entry 16) and up to 99% ee could be attained with Q-4a at −55° C. (entry 18).

A wide range of nitroalkenes (5) bearing aryl, heteroaryl and alkyl groups were treated with methyl malonate in THF at −20° C. in the presence of either QD-4a and Q-4a. Results are shown in Table 2.

TABLE 2

1,4-Addition of Dimethyl Malonate to Nitroalkenes Catalyzed by Q-4a and QD-4a[a,b].

| Entry | R | Time (h) | Yield (%)[c] | ee (%)[d] |
|---|---|---|---|---|
| 1 | 5a Ph | 36 (36) | 97 (99) | 96[g] (93) |
| 2 | 5b 4-F-Ph | 36 (36) | 97 (97) | 97 (94) |
| 3 | 5c 4-Cl-Ph | 36 (36) | 97 (97) | 97 (94) |

TABLE 2-continued 1,4-Addition of Dimethyl Malonate to
Nitroalkenes Catalyzed by Q-4a and QD-4a[a,b].

Q-4a or QD-4a (10 mol %)
CH$_2$(CO$_2$Me)$_2$ (3.0 equiv.)
THF (0.2 mL)
−20° C.

R—CH=CH—NO$_2$  →  MeOOC—CH(COOMe)—CH(R)*—CH$_2$—NO$_2$ 5 (0.2 mmol)        6

| Entry | | R | Time (h) | Yield (%)[c] | ee (%)[d] |
|---|---|---|---|---|---|
| 4 | 5d | 4-Br-Ph | 36 (36) | 99 (98) | 96 (94) |
| 5 | 5e | 4-Me-Ph | 36 (44) | 97 (97) | 98 (94) |
| 6 | 5f | 4-$^i$Pr-Ph | 36 (39) | 95 (96) | 97 (93) |
| 7 | 5g | 4-MeO-Ph | 44 (47) | 90 (94) | 97 (95) |
| 8 | 5h | 3-Me-Ph | 36 (36) | 97 (99) | 97 (93) |
| 9 | 5i | 2-Me-Ph | 36 (36) | 95 (97) | 98 (96) |
| 10 | 5j | 2-F-Ph | 36 (36) | 97 (94) | 97 (95) |
| 11 | 5k | 2-NO$_2$-Ph[e] | 69 (72) | 90 (88) | 97 (92) |
| 12 | 5l | 1-naphthyl | 36 (36) | 99 (99) | 98 (92) |
| 13 | 5m | 2-thienyl | 36 (44) | 99 (96) | 98 (95) |
| 14 | 5n | 2-furyl | 36 (36) | 97 (95) | 98 (96) |
| 15 | 5o | 3-pyridinyl | 36 (36) | 98 (99) | 96 (92) |
| 16 | 5p | pentyl | 72 (72) | 81 (82) | 94 (91) |
| 17 | 5q | $^t$Bu | 72 (72) | 86 (84) | 94 (92) |
| 18 | 5r | cyclohexyl[f] | 108 (108) | 71 (80 | 94 (91) |
| 19 | 5s | BOCH$_2$ | | | 89 (87) |

[a]Unless noted the reaction is run at −20° C.
[b]The results in parentheses are obtained with QD-4a.
[c]Reaction was performed at −55° C.
[d]Using 20 mol% catalyst.
[e]The absolute configuration is determined to be S.

Aryl and heteroaryl nitroalkenes (5a-o) were found to be cleanly converted into the corresponding 1,4-adducts in 92-98% ee and 90-99% yield. High enantioselectivity and yield were also obtained with nitroalkenes (5p-r) bearing alkyl groups of various steric properties. The consistently excellent results obtained with heteroaryl and alkyl nitroalkenes (5m-r) are noteworthy, as they were shown to be relatively challenging substrates in previous studies involving chiral Mg-bis(oxazoline) complexes and organic catalysts. The results obtained with 5r represent the first example of a highly enantioselective addition of a malonate to a sterically hindered γ-branched nitroalkene.

The significantly higher enantioselectivity and faster rate obtained with QD-4a-c vs. those obtained with quinidine (QD-1) indicate that the C6'-OH plays an important role in the stabilization and organization of the transition state of the enantioselective 1,4-addition. We have also attempted to use phenol, instead of QD-4a or Q-4a, to promote the addition of methyl malonate to nitroalkene 5a, and detected no formation of the 1,4-adduct after 24 h. These results indicate that the presence of both the C6'-OH and the amine functionalities are critical for the highly efficient enantioselective catalysis of cinchona alkaloids 4. FIGS. 3-7 depict additional reaction results of the present invention.

Reaction of Cinchona Alkaloid Catalysts with Tertiary Nucleophiles

The results with secondary nucleophiles prompted the examination of conjugate additions involving trisubstituted carbon nucleophiles, especially those that could be conveniently generated in situ from readily available racemic carbonyl compounds. Screening of catalysts 4 for addition of cyclic ketoester 3A to nitroalkene 2a in THF at room temperature revealed that Q-2b affords excellent ee (94 and 95%) for both diastereomers of the 1,4-adducts, which were, however, generated in only a 4.5/1 ratio (Scheme 5). Interestingly, the reaction temperature was found to have a dramatic impact on the diastereoselectivity. Conjugate addition at −60° C. afforded an 18/1 diastereomer ratio with 99% ee for the major diastereomer.

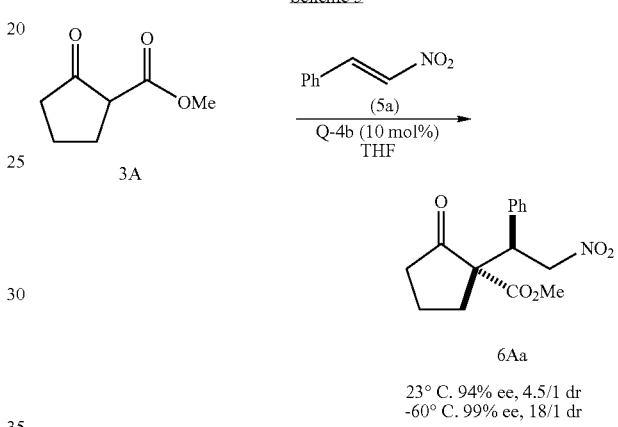

Scheme 5

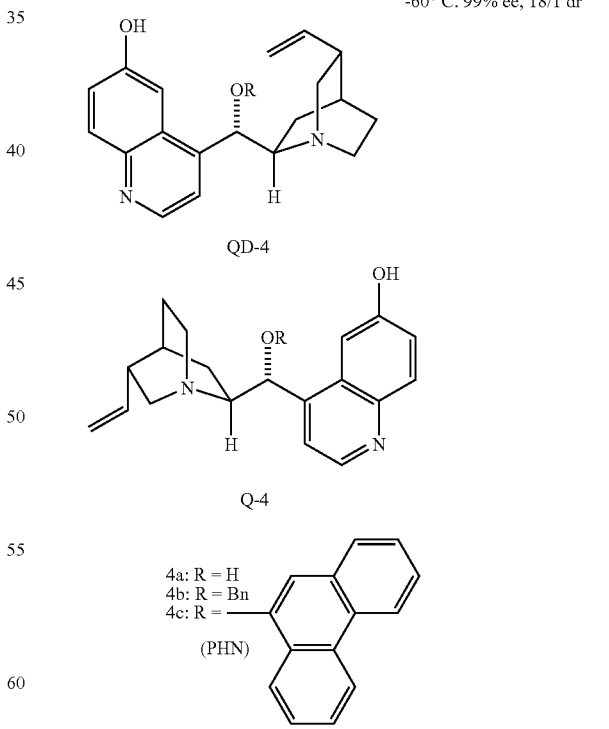

Following this encouraging result, a wide variety of trisubstituted carbon Michael donors were examined for conjugate additions to nitroalkenes 5 mediated by Q-4 (Table 3).

TABLE 3

Diastereoselective and Enantioselective 1,4-Addition Catalyzed by Q-4.

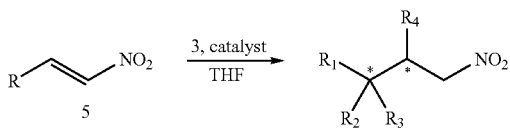

5: a, R = Ph;
b, R = 2-thienyl;
c, R = 4-Br-Ph;
d, R = 4-Cl-Ph;
e, R = $^i$Bu;
f, R = $^n$Pentyl

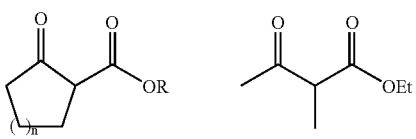

3A n = 1, R = Me
3B n = 2, R = Et

3C

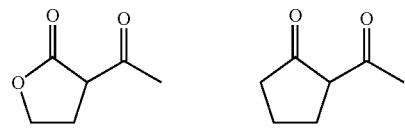

3D

3E

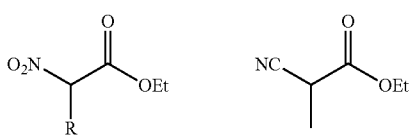

3F R = Me
3G R = Et

3H

| Entry | 3 | 5 | catalyst | T/° C. | time | % ee[b] | dr[c] | % yield[d] |
|---|---|---|---|---|---|---|---|---|
| 1 | 3A | 5a | Q-4b | −60 | 48 h | 99 | 95:5 | 94 |
| 2 | 3A | 5e | Q-4b | −60 | 4 d | 99 | >98:2 | 87 |
| 3 | 3B | 5a | Q-4a | −20 | 72 h | 99 | >98:2 | 93 |
| 4 | 3B | 5b | Q-4a | −20 | 74 h | 99 | >98:2 | 91 |
| 5 | 3B | 5c | Q-4a | −20 | 74 h | >99 | >98:2 | 95 |
| 6 | 3B | 5e | Q-4c | 23 | 4 d | 99 | >98:2 | 83 |
| 7 | 3C | 5a | Q-4c[e] | −20 | 63 h | >99 | 91:9 | 73[g] |
| 8 | 3D | 5d | Q-4b | −60 | 44 h | 99 | 98:2 | 87 |
| 9 | 3D | 5e | Q-4c | −60 | 48 h | 99 | 98:2 | 82 |
| 10 | 3E | 5a | Q-4b | −60 | 48 h | 99 | 86:14 | 76[g] |
| 11 | 3F | 5a | Q-4a | −20 | 60 h | 92 | 92:8 | 78[g] |
| 12 | 3F | 5f | Q-4a | −20 | 84 h | 92 | 93:7 | 78[g] |
| 13 | 3G | 5a | Q-4a[f] | −50 | 6 d | 96 | 95:5 | 77 |
| 14 | 3H | 5a | Q-4b[f] | −50 | 6 d | >99 | >98:2 | 77g |
| 15 | 3H | 5f | Q-5a | −20 | 84 h | 98 | 93:7 | 75 |

[a]Reactions were run with 0.2 mmol scale in 0.2 mL THF with 10 mol % Q-2.
[b]Determined by HPLC analysis.
[c]Determined by $^1$H NMR analysis of crude product.
[d]Isolated yield.
[e]15 mmol % catalyst was used.
[f]20 mol % catalyst was used.
[g]For pure major diastereomer. (see Supporting Information)

Outstanding diastereoselectivity and enantioselectivity were obtained with various cyclic and acyclic β-ketoesters (3A-D). Similarly high enantioselectivity was also observed for 2-substituted-1,3-diketone 3E, the diastereoselectivity decreased noticeably yet remains synthetically useful. Importantly, high diastereoselectivity and enantioselectivity can also be attained with trisubstituted carbon Michael donors that are not 1,3-dicarbonyl compounds (3F-H), including even those bearing a heteroatom substituent (3F-G). It is noteworthy that catalysts Q-4 accept this unprecedented scope of trisubstituted carbon Michael donors and still tolerate a wide range of nitroalkenes (5a-f) bearing aryl, heteroaryl and alkyl groups with varying electronic and steric properties.

Mechanistic studies were carried out to gain insight into the transition state assembly of this reaction. The absolute configuration of 6Dd generated using Q-4b and the relative configuration of 6De have been determined by X-ray crystallography. We established that the asymmetric Michael addition follows a first-order dependence on the catalyst, the donor and the acceptor. We also found that the reaction proceeds at significantly higher stereoselectivities in aprotic solvents (THF, ether and toluene) rather than protic solvents (MeOH, EtOH) that could form hydrogen bond with either the catalyst or the substrates. To delineate the active conformer for the flexible catalysts 4 in the transition state, we compared their stereoselectivities with those of 7, a conformationally rigid catalyst, in Michael additions utilizing a variety of combinations of donors and acceptors (catalyst 6 is first reported by Hatakeyama, see: (a) Iwabuchi, Y.; Nakatani, M.; Yokoyama, N.; Hatakeyama, S. *J. Am. Chem. Soc.* 1999, 121, 10219; (b) Kawahara, S.; Nakano, A.; Esumi, T.; Iwabuchi, Y.; Hatakeyama, S. *Org. Lett.* 2003, 5, 3103). The remarkably similar dr and ee profiles thus exhibited by QD-4 and 6 provide powerful evidence to support a gauche-open active conformer for catalysts 4 in the transition state (Table 4). For the use of conformationally rigid cinchona alkaloids to probe the active conformer of cinchona alkaloids as ligands for Os-catalyzed Sharpless asymmetric dihydroxylations see: (a) Corey, E. J.; Noe, M. C. *J. Am. Chem. Soc.* 1993, 115, 12579. (b) Corey, E. J.; Noe, M. C. *J. Am. Chem. Soc.* 1996, 118, 11038. For a study of the active conformer of cinchona alkaloids as organic catalysts see: Cortez, G. S.; Oh, S. H.; Romo, D. *Synthesis* 2001, 1731.

TABLE 4

Asymmetric Michael Additions Catalyzed by QD-4 and 6[a].

| Entry | 3 | 5 | catalyst | T/° C. | % ee | dr | % yield |
|---|---|---|---|---|---|---|---|
| 1 | 3A | 5a | QD-4c(6) | −60 | >99(98) | 94:6(97:3) | 97(97) |
| 2 | 3B | 5c | QD-4a(6) | −60 | 99(98) | >98:2(>98:2) | 96(97) |
| 3 | 3C | 5a | QD-4c(6) | −20 | 99(96) | 82:18(89:11) | 70(75) |
| 4 | 3D | 5d | QD-4c(6) | −60 | 98(98) | 97:3(97:3) | 92(92) |
| 5 | 3E | 5a | QD-4c(6) | −60 | 98(96) | 88:12(90:10) | 70(80) |
| 6 | 3F | 5a | QD-4a(6) | −20 | 89(88) | 89:11(95:5) | 74(80) |
| 7 | 3H | 5a | QD-4a(6) | −20 | 95(88) | 86:14(86:14) | 76(74) |

[a]Reactions were run under the same condition as described in Table-3.

These results are also synthetically noteworthy for establishing QD-4 and 6 as efficient catalysts for the asymmetric Michael addition.

With this key insight into the active conformer of the catalysts 4, the kinetic results consistent with an acid-base bifunctional catalysis mode, and the observed solvent effect indicating an important role played by hydrogen bond interactions between the catalyst and the substrates, a transition state model (8) to rationalize the stereochemical outcome of the asymmetric Michael addition is proposed (Scheme 6).

Scheme 6. Stereochemical model for Michael additions catalyzed by QD-4 and 6.

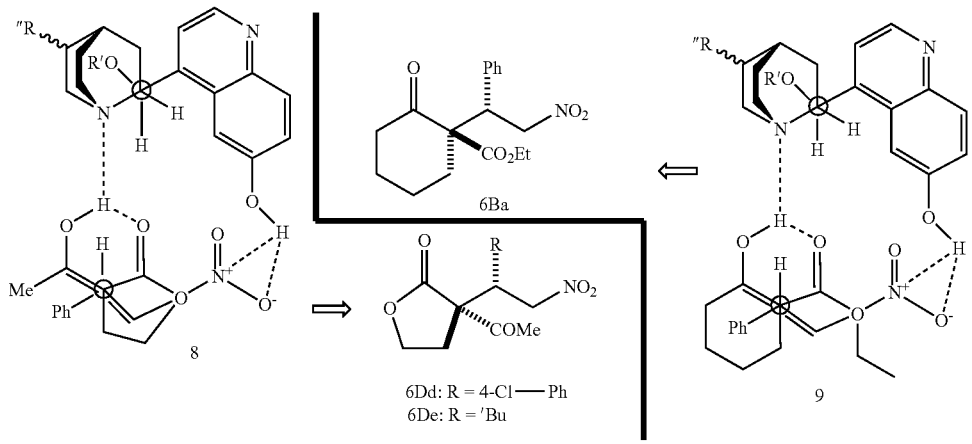

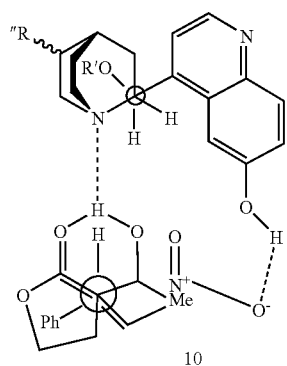

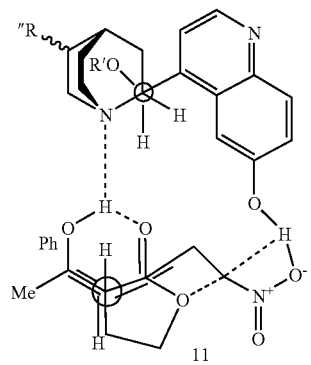

In this model cinchona alkaloids 4 or 7 adopt a gauche-open conformer to simultaneously activate and orient the Michael donor and the acceptor via a network of hydrogen bonding interactions. The substituents of the two bond-forming carbons are in a staggered rather than eclipsed arrangement. Alternative transition states generating the other stereoisomers are relatively disfavored due to either the loss of hydrogen bond interaction between the chiral catalyst and the substrates (10) or the engagement of unfavorable eclipsed interactions between the substituents of the bond forming carbons (11). This model (9) predicted that the adduct 6Ba should have a relative configuration as shown in Scheme 6. Gratifyingly, this was confirmed by X-ray analysis.

Figure 8:
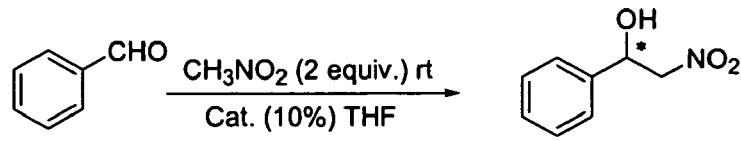
FIG. 8 depicts the results of several asymmetric Michael additions and Aldol additions of the present invention.
Figure 8:
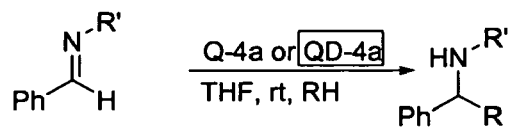
Figure 8:
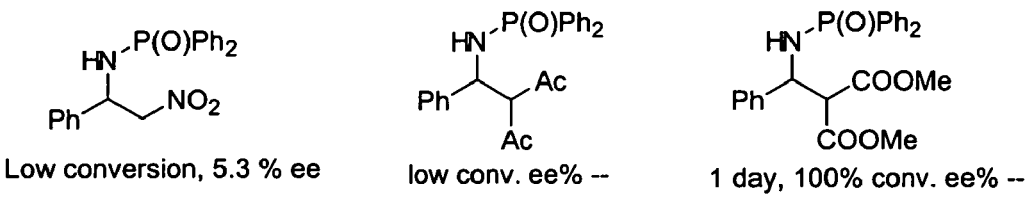
Figure 8:
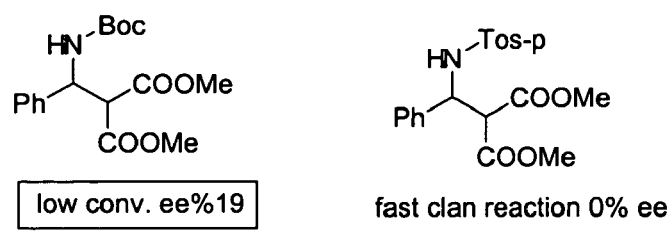
Figure 8:
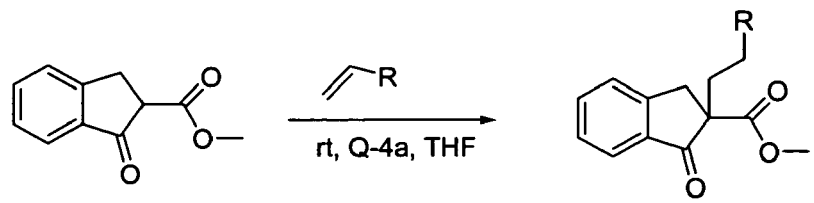
Figure 8:
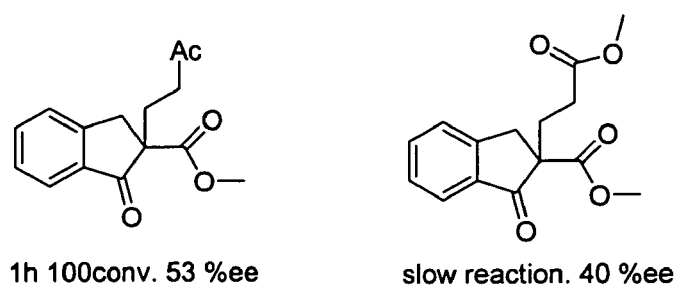
Figure 9:
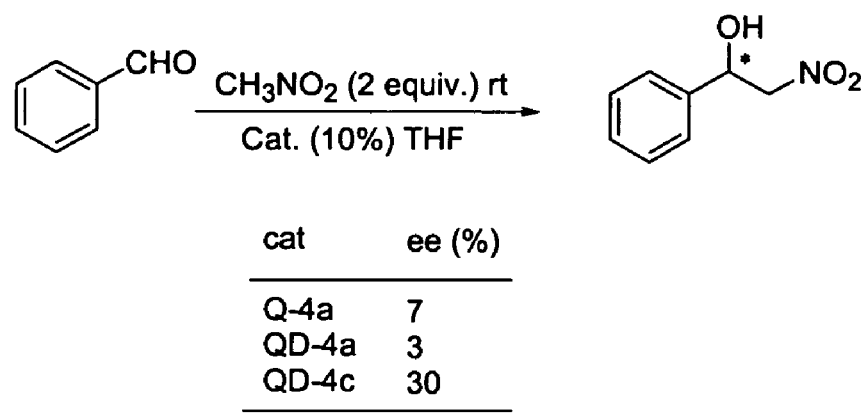
FIG. 9 depicts the results of several asymmetric Aldol additions of the present invention.
Figure 10:
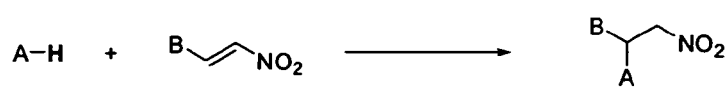
FIG. 10 depicts the results of several asymmetric Michael additions of the present invention.
Figure 11:
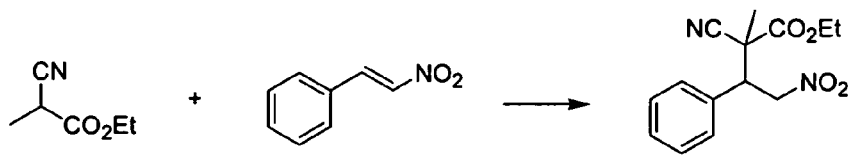
FIG. 11 depicts the results of several asymmetric Michael additions of the present invention.
Figure 11:
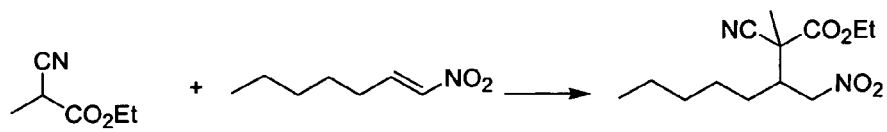
Figure 11:
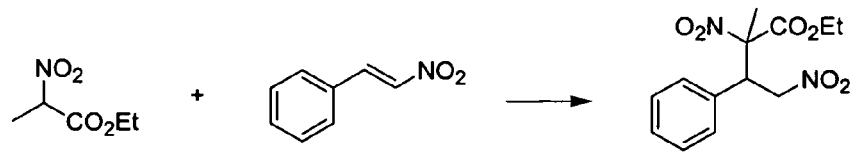
Figure 12:
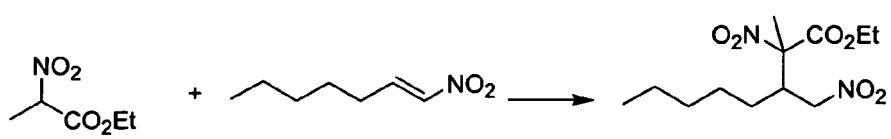
FIG. 12 depicts the results of several asymmetric Michael additions of the present invention.
Figure 12:
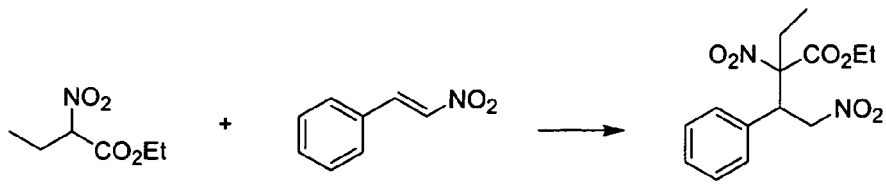
Figure 12:
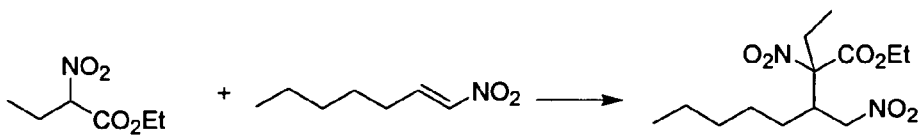

In addition to stereoselective Michael additions of tertiary nucleophiles to nitroalkenes (see also FIGS. 3-5, 7, 10, 11, and 12), reactions with substrates other than nitroalkenes were also carried out (see FIGS. 8 and 9 for aldol additions and Michael additions where the $NO_2$ group is replaced by Ac or $CO_2Me$). Although the ee's obtained are not as impressive as those obtained with nitroalkenes, a notable exception is when the substrate is an azodicarboxylate as shown in Table 5.

TABLE 5

Catalytic asymmetric reaction of ethyl 2-cyano-2-arylacetate and dialkyl azodicarboxylate at optimized conditions.

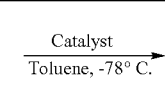

| Entry | Ar | R | Catalyst (%) | Time (h) | Yield (%) | ee % |
|---|---|---|---|---|---|---|
| 1 | Ph | t-Bu | Q-4b(5) | 4 | 92 | 97 |
|   |    |      | QD-4b (5) | 2 | 92 | 95 |
| 2 | p-F-C$_6$H$_4$ | t-Bu | Q-4b (5) | 2 | 95 | 96 |
|   |   |   | QD-4b (5) | 1 | 97 | 94 |
| 3 | p-Br-C$_6$H$_4$ | t-Bu | Q-4b (5) | 2 | 97 | 96 |
|   |   |   | QD-4b (5) | 1 | 99 | 93 |
| 4 | 1-naphthyl | t-Bu | Q-4b (10) | 12 | 98 | 99 |
|   |   |   | QD-4b (10) | 8 | 99 | 96 |
| 5 | p-Me-C$_6$H$_4$ | t-Bu | Q-4b (5) | 8 | 96 | 96 |
|   |   |   | QD-4b (5) | 8 | 96 | 94 |
| 6 | p-MeO—C$_6$H$_4$ | t-Bu | Q-4b (10) | 10 | 96 | 97 |
|   |   |   | QD-4b (10) | 5 | 96 | 94 |
| 7 | o-Me-C$_6$H$_4$ | Bn | Q-4b (5) | 3.5 | 72 | 87 |
|   |   |   | QD-4b (5) | 1 | 71 | 82 |

Reaction was performed with 1.1 equiv of ethyl α-Aryl-α-Cynoacetate in toluene (0.1 M) in the presence of chiral catalyst (5%-10%), 1.0 eqiuiv of Dialkyl Azodicarboxylate in toulene (0.5 M) was added dropwise. The mixture was stirred at −78° C. for 1-12 h.

Table 6 shows that doubling the amount of catalyst loading from 10 (mol %) to 20 (mol %) results in lower ee's.

TABLE 6

Reaction condition screening.

| Substrate | Substrate Loading (mmol) | Substrate conc. | Catalyst | Catalyst Loading (mol %) | Azo Compound Loading (eq.) | Solvent | Temp (° C.) | Reaction Time | ee % |
|---|---|---|---|---|---|---|---|---|---|
| 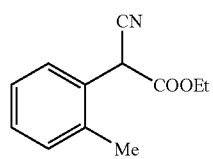 | 0.1 | 0.083 | Bn-QD-4 | 10 | DTAB (1) | Toluene | −78 | 6d (NC) | 94.0% |
| 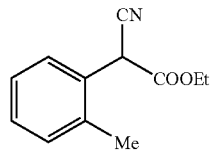 | 0.22 | 0.083 | Bn-QD-4 | 20 | DTAB (1) | Toluene | −78 | 6d (NC) | 81.0% |

NC = Reaction was not completed.

Conjugate additions of carbon nucleophiles to alkenyl sulfones in parallel to those to nitroalkenes constitute a class of synthetically valuable C—C bond forming reactions. A variety of cinchona alkaloid derivatives were screened for their ability to promote enantioselective addition of ethyl 2-cyano-2-phenylacetate to commercially available phenylvinyl sulfone. (a) Taylor, M. S.; Jacobsen, E. N. *J. Am. Chem. Soc.* 2003, 125, 11204; (b) Taylor, M. S.; Zalatan, D. N.; Lerchner, A. M.; Jacobsen, E. N. *J. Am. Chem. Soc.* 2005, 127, 1313. As summarized in Table 7, the conjugate addition proceeded smoothly in toluene at room temperature in the presence of various natural or modified cinchona alkaloids. The enantioselectivity of the reaction was, however, found to be critically dependent on the structure of the cinchona alkaloid derivatives. Reactions with natural cinchona alkaloids such as quinidine and quinine generated the 1,4-adduct as a nearly racemic mixture (entries 1-2). The enantioselectivity was in general improved with cinchona alkaloids bearing a C9-substituent (entries 3-7, 9-12), among which those bearing a C6'-OH were found to be more effective than those bearing a C6'-OMe. The pronounced effect of the C9-substituent on the enantioselectivity of the C6'-OH cinchona alkaloids is also noteworthy. While modest enantioselectivity was afforded by either the C6'-OH cinchona alkaloid bearing a C9-OH (entry 8) or a rigid C6'-OH cinchona alkaloid derivative (entry 7), significantly higher enantioselectivity could be attained with C6'-OH cinchona alkaloids bearing either an aryl or alkyl ether at C9 (entries 9-12). Thus the tunable nature of cinchona alkaloids provided a crucial handle for the optimization of catalytic enantioselectivity. Upon further optimization, an excellent enantioselectivity could be achieved with either QD-4c or Q-4c at −25° C. in toluene (entries 13-14). Various solvents were screened under the same condition as described in entry 11 of Table 7, using Q-4c (20 mol %) as catalyst, at −25° C., after 17 h: TBME (9% conv., 58% ee), CHCl₃ (17% conv. 79% ee), CH₂Cl₂ (17% conv. 74% ee), DCE (22% conv. 81% ee), toluene (46% conv., 95% ee).

TABLE 7

Cinchona Alkaloid-Catalyzed Addition of Ethyl 2-cyano-2-phenylacetate to Phenylvinyl sulfone[a]

| Entry | Cat.[b] | Conv.(%)[c] | ee(%)[d] |
|---|---|---|---|
| 1 | Q | >98 | 0 |
| 2 | QD | >98 | 3 |
| 3 | DHQD-PHN | 79 | 24 |
| 4 | (DHQD)₂PYR | >98 | 33 |
| 5 | (DHQD)₂PHAL | 80 | 9 |
| 6 | (DHQD)₂AQN | >98 | 4 |
| 7 | β-ICD | >98 | 42 |

| Entry | Cat. | Conv.(%) | ee(%) |
|---|---|---|---|
| 8 | QD-4a | 90 | 45 |
| 9 | QD-4b | >98 | 63 |
| 10 | QD-4c | 91 | 74 |
| 11 | Q-4b | 65 | 74 |
| 12 | Q-4c | >98 | 84 |
| 13[e] | QD-4c | 85 | 91 |
| 14[e] | Q-4c | 95 | 95 |

[a]Unless noted, reactions were run with 0.3 mmol of Ethyl 2-cyano-2-phenylacetate, 0.1 mmol phenylvinyl sulfone in 0.2 mL toluene with 20 mol % catalyst at r.t. for 17 h.
[b]Determined by ¹H NMR analysis.
[c]Determined by HPLC analysis
[d]Reaction was run at −25° C. for 72 h.

A substrate scope study revealed that Ethyl 2-cyano-2-arylacetates 12 bearing a range of aryl groups of varying electronic and steric properties underwent efficient enantioselective addition to phenylvinyl sulfone, providing the 1,4-adduct 14 bearing the all-carbon quaternary stereocenter in excellent enantioselectivity and good to excellent yield (Table 8). Notably, high enantioselectivity and yield could also be obtained with an Ethyl 2-cyano-2-heteroarylacetates (entry 9, Table 8).

TABLE 8

Enantioselective Conjugate Addition of Ethyl 2-cyano-2-Arylacetate 12 to Phenylvinyl sulfone Catalyzed by Q-4c and QD-4c (in brackets).[a]

| Entry | R | T/° C. | Time/h | yield/%[b] | ee/%[c] |
|---|---|---|---|---|---|
| 1 | 12A Ph- | −25 | 72 (72) | 89 (80) | 95 (91) |
| 2 | 12B 4-Me-Ph- | 0 | 48 | 96 | 93 |
| 3 | 12C 4-MeO-Ph- | 0 | 70 | 92 | 93 |
| 4 | 12D 4-F-Ph- | −25 | 72 | 90 | 94 |
| 5 | 12E 4-Cl-Ph- | −25 | 69 (72) | 95 (94) | 94 (89) |
| 6 | 12F 4-Br-Ph- | −25 | 66 (72) | 95 (95) | 94 (88) |
| 7 | 12G 3-Cl-Ph- | −25 | 60 | 96 | 93 |
| 8 | 12H 2-Naphthyl- | −25 | 60 (60) | 96 (95) | 97 (90) |
| 9 | 12I 2-Thienyl- | −25 | 48 (48) | 95 (91) | 93 (88) |

[a]Unless noted, reactions were run with 0.5–0.6 mmol of 2, 0.2 mmol phenylvinyl sulfone in 0.4 mL toluene with 20 mol% Q-4c and the catalyst was recovered in greater than 95% yield, the results in parentheses were obtained with QD-4c to give opposite enantiomer.
[b]Isolated yield.
[c]Determined by HPLC analysis.

Having established a general scope with respect to ethyl 2-cyano-2-arylacetates, conjugate addition with ethyl 2-cyano-2-alkylacetates were carried out. When compared to their aryl congeners, ethyl 2-cyano-2-alkylacetates were significantly less active as Michael donor for the cinchona alkaloid-catalyzed conjugate addition to alkenyl sulfones. While addition of ethyl 2-cyano-2-phenylacetate 12A to phenylvinyl sulfone with Q-4c proceeded to completion at room temperature after 17 hours (entry 12, Table 9), the addition of ethyl 2-cyano-2-allylacetate 12J proceeded to only 17% conversion during the same period (entry 1, Table 9).

Michael donor and acceptor employed in a practically attractive 1:1 stoichiometry, the conjugate addition of 12J to 13b in complete conversion and excellent enantioselectivity was eventually attained at 0° C. (entry 3, Table 9). Importantly, the high enantioselectivity could be readily extended to the conjugate addition of ethyl 2-cyano-2-methylacetate 12K to 13b (entry 4, Table 9).

TABLE 9

9 Enantioselective Conjugate Addition of Ethyl 2-cyano-2-alkylacetates 12 to Phenylvinyl sulfone 13 Catalyzed by Q-4c and QD-4c (in brackets).[a]

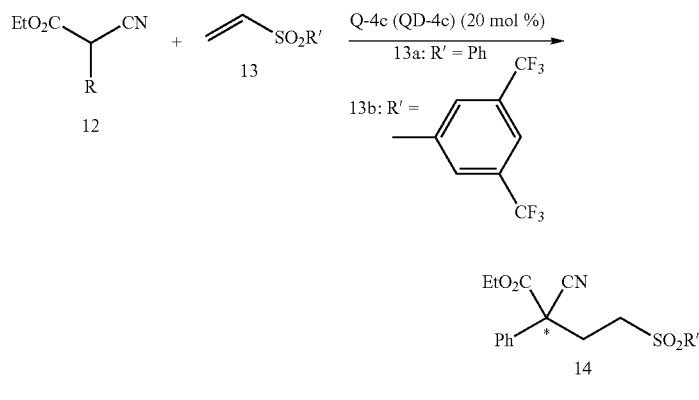

| Entry | 12 | R | 13 | T/° C. | Time/h | Conv./%[b] | yield/%[c] | ee/%[d] |
|---|---|---|---|---|---|---|---|---|
| 1[e] | 12J | Allyl- | 13a | 23 | 17 | 17 | N.D. | 87 |
| 2[e] | 12J | Allyl- | 13b | 23 | 17 | 88 | N.D. | 86 |
| 3 | 12J | Allyl- | 13b | 0 | 96 | 100 | 76 | 94 |
| 4 | 12K | Me- | 13b | 0 | 96 (96) | 100 (100) | 85 (83) | 92 (88) |

[a]Unless noted, reactions were run with 0.5-0.6 mmol of 12, 0.2 mmol 13 in 0.4 mL toluene with 20 mol% Q-4c and the catalyst was recovered in greater than 95% yield, the results in parentheses were obtained with QD-4c to give opposite enantiomer.
[b]Determined by $^1$HNMR analysis.
[c]Isolated yield.
[d]Determined by HPLC analysis.
[e]Reactions were run with 0.6 mmol of 12, 0.2 mmol 13.

Cinchona alkaloid-catalyzed conjugate addition with ethyl 2-cyano-2-alkylacetates may be accelerated considerably by enhancing the electrophilicity of the alkenyl sulfone 13, which could be implemented via the introduction of electron-withdrawing substituents on the aromatic ring of 13. With this in mind the conjugate addition of 12J to 3,5-bis(triflouromethyl)phenyl vinyl sulfone 13b with Q-4c was carried out at room temperature. The reaction was indeed accelerated, proceeding to 88% conversion after 17 hours to afford the 1,4-adduct in 86% ee (entry 2, Table 9). Thus the ability of 6'-OH cinchona alkaloid catalysts to tolerate the structural change of the alkenyl sulfone acceptor allowed significant improvement of the rate of the conjugate addition of an ethyl 2-cyano-2-alkylacetate by tuning the electronic property of the alkenyl sulfone acceptor. With the The synthetic utility of the optically active chiral sulfones 14 is demonstrated in the development of a versatile catalytic enantioselective approach toward α,α-disubstituted amino acids. (Scheme 6).

Scheme 6 Synthesis of optically active α,α-disubstituted amino acids

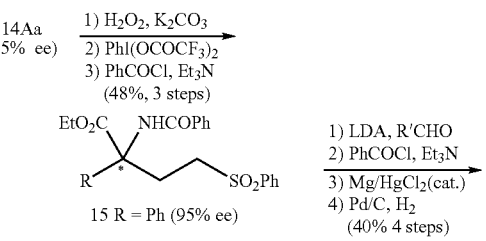

-continued

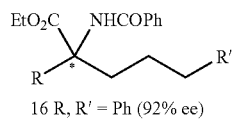

16 R, R' = Ph (92% ee)

The enantioselective addition with alkenyl sulfones was applied to the asymmetric synthesis of the biologically significant α,α-disubstituted amino acids. As shown in the synthesis of 16, an amino acid that was previously not accessible via asymmetric catalysis, the approach complements existing catalytic methods, thereby expanding the range of α,α-disubstituted amino acids accessible by catalytic a symmetric synthesis. For a review, see: Cativiela, C.; Díaz-de-Villegas, M. D. *Tetrahedron: Asymmetry* 1998, 9, 3517; for recent reports see: (b) Ooi, T.; Takeuchi, M.; Kameda, M.; Maruoka, K. *J. Am. Chem. Soc.* 2000, 122, 5228; (c) Maruoka, K.; Ooi, T. *Chem. Rev.* 2003, 103, 3013; (d) Vachal, P.; Jacobsen, E. N. *Org. Lett.* 2000, 2, 867; (e) Vachal, P.; Jacobsen, E. N. *J. Am. Chem. Soc.* 2002, 124, 10012; (f) Chavarol, M.; Byrne, J. J.; Chavant, P. Y.; Vallée, Y. *Tetrahedron: Asymmetry* 2001, 12, 1147; (g) Masumoto, S.; Usuda, H.; Suzuki, M.; Kanai, M.; Shibasaki, M. *J. Am. Chem. Soc.* 2003, 125, 5634.

Similarly, the conjugate addition of β-ketoesters to alkenyl ketones provides a powerful strategy for the creation of all-carbon quaternary stereocenters, due to the accessibility of a wide range of both the Michael donors and acceptors and the proven wide utility of the 1,4-adducts. Although 6'-OH cinchona alkaloids Q-4 and QD-4 were shown to be efficient bifunctional chiral organic catalysts for the conjugate additions of various carbon nucleophiles to nitroalkenes, initial attempts to apply Q-4 and QD-4 to promote an enantioselective addition of α-substituted-β-ketoesters 22 to methylvinyl ketone (MVK) were, however, unsuccessful. The reaction of ketoester 22A and MVK with Q-4 in toluene went to completion at room temperature after 0.5-2 hours. Unfortunately, the 1,4-adduct 24Aa was formed in only moderate ee (entries 1-3, table 10). The enantioselectivity could be improved by performing the reaction in either methylene chloride or ether (ethyl acetate, THF, DMF, chloroform, TBME, diethyl ether, methanol, toluene have been screened) and by decreasing the reaction temperature. However, even at −78° C., it could not reach a synthetically useful level (entry 6, table 10). Investigations into the effect of modifying the ester group of ketoesters 22 on the enantioselectivity were carried out. The conjugate addition of t-butyl ketoester 22B to MVK with either QD-4b or Q-4b proceeded to completion in only 30 minutes, and more significantly, occurred in a highly enantioselective fashion even at room temperature (entries 7-8, table 10). The enantioselectivity was further increased with catalyst Q-4c, generating the 1,4-adduct 24Ba in up to 97% ee (entry 10, table 10). Significantly, complete and highly enantioselective conjugate addition could be secured within three hours even with a catalyst loading of only 1.0 mol % (entry 11, table 10).

TABLE 10

Conjugate addition of ketone ester 22A-B to MVK[a,b]

22A R = Me
22B R = ᵗBu

22Aa R = Me
22Ba R = ᵗBu

| Entry | 22 | Catalyst | Solvent | T(° C.) | Time | ee %[c] |
|---|---|---|---|---|---|---|
| 1 | 22A | QD-4a | Toluene | 23 | 1 h | 40 |
| 2 | 22A | QD-4b | Toluene | 23 | 0.5 h | 59 |
| 3 | 22A | QD-4c | Toluene | 23 | 2 h | 58 |
| 4 | 22A | QD-4b | Et$_2$O | 23 | 0.5 h | 64 |
| 5 | 22A | QD-4b | CH$_2$Cl$_2$ | 23 | 0.5 h | 66 |
| 6 | 22A | QD-4b | CH$_2$Cl$_2$ | −78 | 12 h | 80 |
| 7 | 22B | QD-4b | CH$_2$Cl$_2$ | 23 | 0.5 h | 91 |
| 8 | 22B | Q-4b | CH$_2$Cl$_2$ | 23 | 1 h | 92 |
| 9 | 22B | QD-4c | CH$_2$Cl$_2$ | 23 | 1 h | 94 |
| 10 | 22B | Q-4 | CH$_2$Cl$_2$ | 23 | 1 h | 97 |
| 11[d] | 22B | Q-4c | CH$_2$Cl$_2$ | 23 | 3 h | 96 |

[a]Unless specified, the reaction was run with 22 (0.5 M in the indicated solvent) and MVK (2.5 eq.) in the presence of Q-4 and QD-4 (10 mol %).
[b]All reactions went to completion at the indicated time.
[c]Determined by HPLC analysis.
[d]The reaction was run with 22B (0.5 M in CH$_2$Cl$_2$) and MYK (2.5 eq.) with 1 mol % Q-4c.

In light of these promising results, the scope of the reaction was investigated (table 11). The additions of cyclic aromatic β-ketoesters 22B-D to methyl, ethyl, and aryl alkenyl ketones (23a-d) proceeded rapidly to completion in excellent enantioselectivity and high yield (entries 1-5, table 11). Relative to the addition of 22B to 23a, the reaction rate decreased noticeably for the addition of 22E, an aliphatic cyclic ketoester, to 23a, (entry 6 vs. 1, table 11). Additional inquiries were guided by the hypothesis that the significantly decreased acidity of the α-proton of 22E relative to that of 22B could be the cause of the dramatically reduced rate, the addition of 22F, an aliphatic ketoester bearing a strong electron-withdrawing hexafluoroisopropyl ester group, to MVK 23a. Delightfully, the reaction with 10 mol % of Q-4c and QD-4c proceeded to completion within 30 minutes to afford the 1,4-adduct 24Da in 96% and 95% ee and excellent yields, respectively. Again, both the enantioselectivity and yield remains high when the catalyst loading was reduced to 1.0 mol % (entry 8, table II). The additions of the 6-membered cyclic ketoester 22G and acyclic ketoester 22H to MVK (23a) with QD-4c were also found to be highly enantioselective (entries 9-10, table 11). Although 10 mol % of QD-4c was employed for these additions to ensure a complete reaction within 24 h, it should be noted that QD-4c could be easily recycled in nearly quantitative fashion.

TABLE 11

Construction of All-Carbon Quaternary Stereocenters via Conjugate addition of ketoester to enone[a]

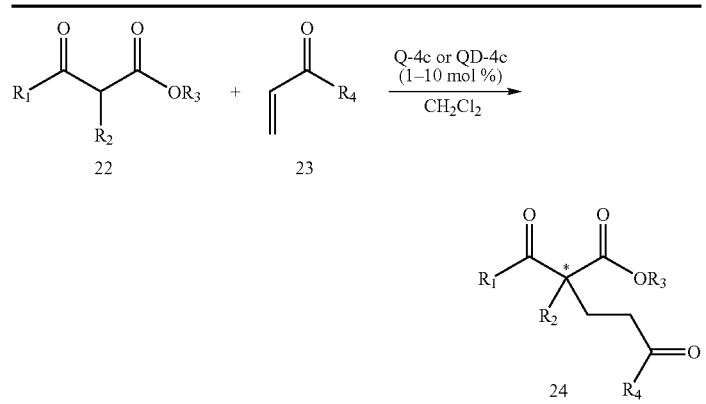

Cyclic α-substituted β-ketoester:

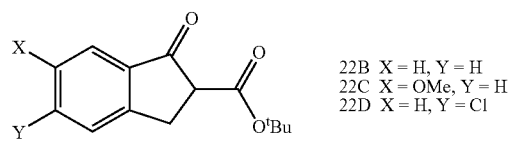

22B X = H, Y = H
22C X = OMe, Y = H
22D X = H, Y = Cl

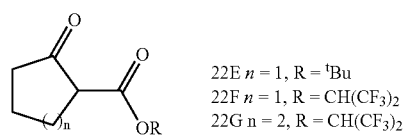

22E n = 1, R = tBu
22F n = 1, R = CH(CF$_3$)$_2$
22G n = 2, R = CH(CF$_3$)$_2$

Acyclic α-substituted β-ketoester:

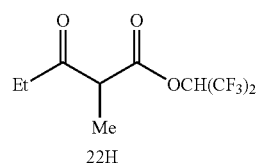

22H

Vinyl Ketone:

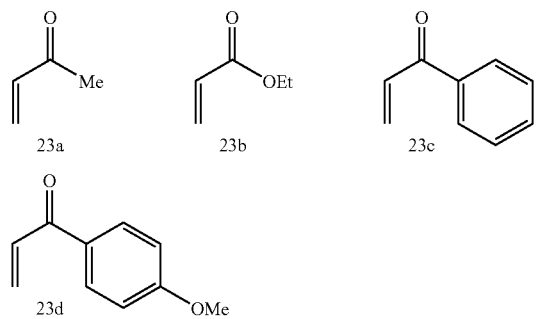

| Entry | 22 | 23 | Catalyst | Cat. Loading (mol %) | T (°C.) | Time (h) | Yield[b] (%) | ee[c] (%) |
|---|---|---|---|---|---|---|---|---|
| 1 | 22B | 23a | Q-4c (QD-4c) | 1 | 23 | 3 h | 96(93) | 96[d](95) |
| 2 | 22B | 23b | Q-4c | 1 | 23 | 5 h | 94 | 94 |

TABLE 11-continued

Construction of All-Carbon Quaternary Stereocenters
via Conjugate addition of ketoester to enone[a]

| | | | | | | | | |
|---|---|---|---|---|---|---|---|---|
| 3 | 22C | 23a | Q-4c (QD-4c) | 1 | 23 | 5 h | 98(99) | 96(96) |
| 4 | 22B | 23c | Q-4c (QD-4c) | 10 | −24 | 0.5 h | 94(94) | 96(93) |
| 5[e] | 22D | 23d | Q-4c (QD-4c) | 10 | −27 | 8 h | 94(93) | 96(93) |
| 6 | 22E | 23a | Q-4c | 10 | 23 | 84 h | 95 | 96 |
| 7 | 22F | 23a | Q-4c (QD-4c) | 10 | 23 | 0.5 h | 93(90) | 96(95) |
| 8 | 22F | 23a | Q-4c | 1 | 23 | 24 h | 92 | 94 |
| 9 | 22G | 23a | Q-4c (QD-4c) | 10 | 23 | 24 h | 89(86) | 98(96) |
| 10 | 22H | 23a | Q-4c (QD-4c) | 10 | −24 | 20 h | 82(85f) | 90(90) |

[a]Unless specified, the reaction was performed by treatment of 22 (0.3 mmol) with 23 (0.75 mmol, 2.5 eq.) and the catalyst in $CH_2Cl_2$ (0.6 mL). The results in parenthesis were obtained with QD-4c.
[b]Isolated yield.
[c]Determined by HPLC analysis.
[d]The absolute configuration was determined to be R by comparison with reported data.
[e]The reaction was started with a solution of 22 (0.2 mmol) and QD-4c (0.02 mmol, 10 mol%) in $CH_2Cl_2$ (0.4 mL), then a solution of 23 (0.5 mmol, 2.5 eq.) in $CH_2Cl_2$ (0.4 mL) was added at a speed of 0.07 mL/hr.
[f]The reaction was run for 40 h.

The substrate scope study summarized in Table 11 reveals a rapid, clean and highly enantioselective conjugated addition that allows the employment of cyclic and acyclic β-ketoesters as the donor and alkenyl ketones bearing either an alkyl or an aryl substituent as the acceptor. The ability of QD-4c to afford consistently excellent enantioselectivity for various alkenyl ketones is particularly noteworthy, as excellent enantioselectivity (>90% ee), to our knowledge, had not been achieved for catalytic conjugate additions of α-substituted ketoesters to alkenyl ketones other than MVK (23a).

EXEMPLIFICATION

The invention now being generally described, it will be more readily understood by reference to the following examples which are included merely for purposes of illustration of certain aspects and embodiments of the present invention, and are not intended to limit the invention.

General Information. $^1$H and $^{13}$C NMR spectra were recorded on a Varian instrument (400 MHz and 100 MHz, respectively) and internally referenced to tetramethylsilane signal or residual protic solvent signals. Data for $^1$H NMR are recorded as follows: chemical shift (δ, ppm), multiplicity (s, singlet; d, doublet; t, triplet; q, quartet; m, multiplet), integration, coupling constant (Hz). Data for $^{13}$C NMR are reported in terms of chemical shift (δ, ppm). Infrared spectra were recorded on a Perkin Elmer FT-IR Spectrometer and are reported in frequency of absorption. Low resolution mass spectra for all the new compounds done by either 20 eV, $CH_4$/CI or $NH_3$/CI were recorded on a Hewlett-Packard 5989A GC/MS, and exact mass spectra on a VG 7070 high resolution mass spectrometer. Specific rotations were measured on a Jasco Digital Polarimeter.

High pressure liquid chromatography (HPLC) analysis was performed on a Hewlett-Packard 1100 Series instrument equipped with a quaternary pump, using a Daicel Chiralpak OD, Column (250×4.6 mm) or Regis (R,R)Whelk-O1 Reversible Column (250×4.6 mm). UV detection was monitored at 220 nm or at 254 nm.

Nitroalkenes 5a, 5d, 5k, 5m were purchased from Aldrich Inc. and 5o was purchased from TCI America. They were used without further purification. Other nitroalkenes were prepared according to literature procedures. (a) Denmark, S. E.; Marcin, L, R. *J. Org. Chem.* 1993, 58, 3850-3856. (b) Bulbule, V. J.; Jnaneshwara, G. K.; Deshmukh, R. R.; Borate, H. B.; Deshpande, V. H. *Synthetic Comm.* 2001, 31, 3623-3626.

Ethyl 2-cyano-2-methylacetate was purchased from TCI America, ethyl 2-cyano-2-phenylacetate and all dialkyl azodicarboxylates were purchased from Lancaster and were used as received. Other ethyl 2-cyano-2-arylacetates were prepared according to literature procedures. (a) Kaiser, E. M.; Solter, L. E.; Schwarz, R., A.; Beard, R. D.; Hauser, C. R. *J. Am. Chem. Soc.* 1971, 93, 4237. (b) Albarella, J. M. *J. Org. Chem.* 1977, 42, 2009.

Anhydrous toluene and phenylvinyl sulfone were purchased from Aldrich Inc. Other alkenyl sulfones were prepared according to literature procedure. Alonos, D. A.; Nujera, C.; Varea, M. *Synthesis,* 2003, 277. β-ketone esters were prepared according to literature procedures. (a) Nakajima, M.; Yamamoto, S.; Yamaguchi, Y.; Nakamura, S.; Hashimoto, S. *Tetrahedron,* 2003, 59, 7307-7313. (b) Babler, J. H.; Sarussi, S. J. *J. Org. Chem.,* 1987, 52, 3462-3464. (d) Hintermann, L.; Togni, A. *Helvetiva Chimica Acta,* 2000, 83, 2425-2435. β-ketone ester 22C, 2dD were prepared with modified literature procedures. α,β-unsaturated ketones 23a, 23h were purchased from Aldrich Inc., 23b was purchased from Acros and all were used without other purifications. Other catalysts were purchased from Aldrich Inc. and used without further purification. All solvents were freshly distilled from sodium or $CaH_2$ before use.

Example 1

Preparation of Quinidine 9-O-(9'-Phenanthryl) Ether, QD-PHN

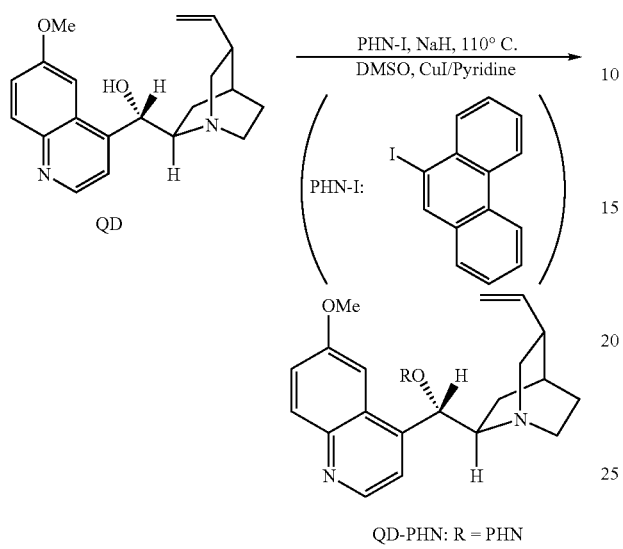

QD-PHN: R = PHN

A 500 mL three-necked round-bottomed flask equipped with a mechanical stirrer, reflux condenser, and inert gas in- and outlet was charged with quinidine (QD-1, 12.8 g, 39.5 mmol, 1.2 eq). The flask was flushed for 30 min with a gentle stream of argon. Anhydrous dimethyl sulfoxide (130 mL, freshly distilled in presence of $CaH_2$) was added, and the reaction mixture was stirred at room temperature until all the quinidine was dissolved. Sodium hydride (60% oil dispersion, 2.0 g, 1.5 eq.) was added in small-portions yielding an orange, slightly cloudy-solution of the corresponding sodium alkoxide. Upon addition of pyridine (6.4 mL, 2.4 eq.) and copper(I) iodide (7.8 g, 1.2 eq.) to the reaction mixture at room temperature, the color of the reaction mixture was changed from orange to dark green. After 30 min all of the precipitate dissolved, and a clear solution was formed. 9-iodophenanthrene (10.0 g, 32.9 mmol), was added, and the reaction mixture was kept at 113° C. for 70 h (oil bath, temperature: 120° C.). The reaction mixture was allowed to cool to room temperature. Water (100 mL), methylene chloride (100 mL), and diethyl ether (100 mL) were successively added to the brown solution followed by ethylenediaminetetraacetate disodium salt dehydrate (20 g) and concentrated aqueous ammonia solution (20 mL, 29%, w/w). The argon inlet was removed, and a gentle stream of air was flushed through the well-agitated reaction mixture for about 1 h. The reaction mixture was transferred to a separatory funnel and the turquoise blue aqueous phase separated from the dark brown organic phase. The aqueous layer was washed twice with methylene chloride (100 mL), and the combined organic phases were extracted three times with aqueous ammonia solution (200 mL, 5%, w/w) until the aqueous phase remained colorless. Then the organic layer was washed with HCl aq (1 N 2×50 mL) twice and washed with $H_2O$ three times (3×50 mL) to remove the left QD. The organic layer was washed with $NH_4OH$ to neutralize the salt and dried over $Na_2SO_4$ and the solvent was removed in vacuo to yield the crude product. The crude product was dissolved in ethyl ether (300 mL) and treated with HCl (1N in $Et_2O$) until no further precipitates was generated. The precipitates were collected and dissolved in $CH_2Cl_2$ and basified with $NH_4OH$ and dried over $Na_2SO_4$ and the solvent in vacuo to give yellowish foam QD-PHN (5.6 g, 66% yield). $[\alpha]_D^{23}=+310.7$(C 0.89 EtOH) $^1$HNMR (CDCl$_3$, 400 Hz) δ 8.65-8.71(m, 2H), 8.61(d, J=4.8 Hz, 1H), 8.52(d, J=8 Hz, 1H), 8.07(d, J=9.2 Hz, 1H), 7.70-7.75(m, 2H), 7.55(d, J=2.4 Hz, 1H), 7.38-7.46(m, 5H), 6.66(s, 1H), 6.35(br, 1H), 6.12-6.21(m, 1H), 5.18(d, J=10.4 Hz, 1H), 5.12(m, 1H), 4.03(s, 3H), 3.32-3.42(m, 2H), 2.97-3.06(m, 2H), 2.79-2.87(m, 1H), 2.44-2.50(t, J=10 Hz, 1H), 2.34-3.25(m, 1H), 1.97(br, 1H), 1.55-1.62(m, 3H). $^{13}$CNMR: (CDCl$_3$, 100 Hz): 158.1, 150.4, 147.71, 144.7, 143.7, 140.3, 132.3, 132.2, 131.5, 127.5, 127.3, 126.8, 126.7, 126.6, 126.4, 124.5, 122.8, 122.7, 122.3, 121.8, 118.2, 114.7, 104.8, 100.8, 78.8, 60.5, 55.8, 50.2, 49.9, 39.6, 27.8, 26.5, 22.1. IR: 3062, 2935, 2863, 1622, 1594, 1507, 1454, 1226, 1117, 750.

Example 2

Preparation of Quinidine 9-O-Benzyl Ether, OD-OBn

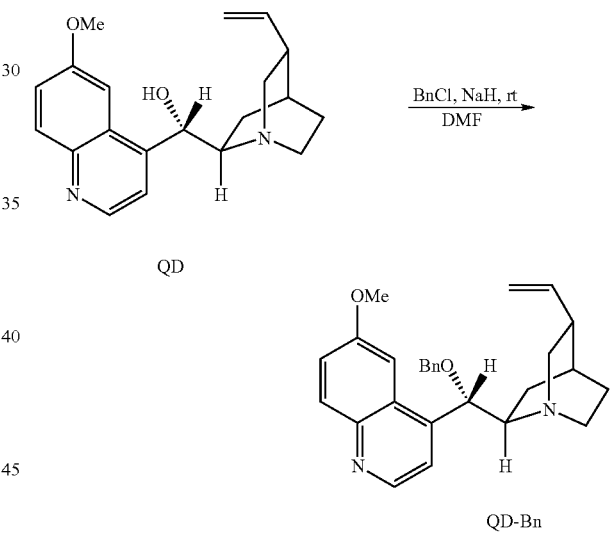

To the solution of QD (2.0 g, 6.2 mmol) in DMF (20 mL, freshly distilled from the suspension of $CaH_2$ in DMF) was added NaH (0.68 g, 57% suspension in mineral oil, 2.5 eq.) and let it stirred at rt for 2 h. Then BnCl (0.78 mL, 1.1 eq.) was added dropwise through syringe in 10 minutes and let it stir overnight. When the reaction was done, the brine was added carefully (20 mL) and the resulting mixture was extracted with ethyl acetate (100 mL). The organic phase was washed with brine (3×50 mL) and dried over $Na_2SO_4$. The solvent was removed in vacuo and purified by flash chromatography (MeOH/Ethyl acetate: 1/40) to give a yellowish oil (2.3 g, 90% yield). $^1$HNMR (400 MHz, CDCl$_3$) δ: 8.77 (d, J=5.2 Hz, 1H), 8.05 (d, J=9.2 Hz, 1H), 7.49 (d, J=4.0 Hz, 1H), 7.40-7.31 (m, 7H), 6.00-5.92 (m, 1H), 5.23 (br, 1H), 5.02-5.00 (m, 1H), 4.97 (s, 1H), 4.49-4.37 (AB, 2H), 3.90 (s, 3H), 3.26 (m, 1H), 3.09-3.08 (m, 1H), 2.93-2.71 (m, 3H), 2.26-2.22 (m, 1H), 2.11-2.05 (m, 1H), 1.75 (br, 1H), 1.51-1.43 (m, 2H), 1.29-1.24 (m, 1H). $^3$CNMR (100

Hz, CDCl$_3$) δ 157.8, 147.6, 144.7, 137.8, 31.9, 128.4, 128.0, 127.8, 127.5, 121.9, 119.1, 114.5, 101.2, 71.3, 60.1, 55.7, 50.1, 49.4, 40.0, 28.1, 26.4.

Example 3

General Procedure for the Preparation of OD-4a, OD-4b, QD-4c and Q-4a

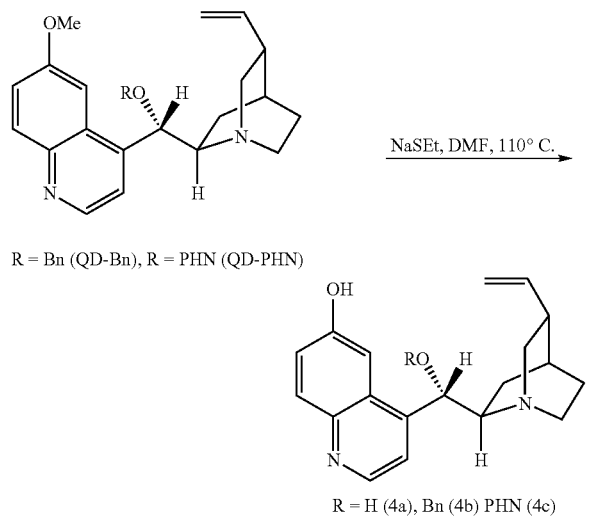

R = Bn (QD-Bn), R = PHN (QD-PHN)

R = H (4a), Bn (4b) PHN (4c)

distilled from the suspension of CaH$_2$ in DMF) was heated at 110° C. for 4-6 hours until a TLC analysis showed that QD was completely consumed. The reaction mixture was cooled down to room temperature, then mixed with sat. NH$_4$Cl (40 mL) and H$_2$O (50 mL) and monitored by pH paper till pH=7. The resulting mixture was extracted with Ethyl Acetate (2×200 mL), the organic phase was washed with brine (4×50 mL), dried over Na$_2$SO$_4$, and concentrated in vacuo. The residue was subjected to flash chromatography (Ethyl Acetate/MeOH/NEt$_3$ system) to afford the desired product.

QD-4a was obtained as a yellowish solid in 92% yield from quinidine. [α]$_D^{25}$=+240.3 (c 1.13, EtOH); $^1$HNMR (400 MHz, CD$_3$OD) δ 8.58 (d, 1H, J=4.4 Hz), 7.88 (d, 1H, J=9.2 Hz), 7.62(d, 1H, J=5.2 Hz), 7.31 (dd, 1H, J=2.4 Hz, 9.2 Hz), 7.25 (d, 1H, J=2.4 Hz), 6.10-6.19 (m, 1H), 5.58 (d, 1H, J=2.8 Hz), 5.10 (d, 1H, J=18.8 Hz), 5.06 (d, 1H, J=10.4 Hz), 3.60 (ddd, 1H, J=2.0 Hz, 8.0 Hz, 13.6 Hz), 3.03 (dt, 1H, J=2.4 Hz, 9.2 Hz), 2.87-2.94(m, 2H), 2.74-2.82(m, 1H), 2.30 (dt, 1H, J=8.8 Hz, 8.4 Hz), 2.18-2.23 (m, 1H), 1.71 (br, 1H), 1.50-1.58 (m, 2H), 1.00-1.07 (m, 1H); $^{13}$CNMR (100 Hz, CD$_3$OD) δ 158.0, 149.8, 147.4, 143.9, 141.6, 131.4, 128.4, 123.3, 119.7, 115.2, 105.1, 72.2, 60.6, 50.8, 50.4, 41.3, 29.7, 27.0, 21.2; IR(CHCl$_3$) ν 3062, 2929, 2300-3500 (br), 1616, 1505, 1229, 739 cm$^{-1}$; HRMS (FAB) m/z calcd for (C$_{19}$H$_{22}$N$_2$O$_2$+H$^+$): 311.1760, found: 311.1755.

QD-4b was obtained as a yellowish powder in 87% yield from QD-Bn. [α]$_D^{25}$=−138.9 (c 1.05, CHCl$_3$); $^1$HNMR (400 MHz, CDCl$_3$) δ 10.92 (br, 1H), 8.67 (d, J=4.4 Hz, 1H), 8.01(d, J=9.2 Hz, 1H), 7.86 (s, 1H), 7.44 (br, 1H), 7.35 (dd, J=2.4 Hz, 8.8 Hz, 1H), 7.24-7.28 (m, 5H), 5.97-5.89 (m, 1H), 5.53 (br, 1H), 4.97 (d, J=10.0 Hz, 1H), 4.94 (s, 1H), 4.34-4.25 (AB, 2H), 3.56 (br, 1H), 3.05-3.03 (m, 2H), 2.87-2.78 (m, 2H), 2.26-2.24 (m, 1H), 1.74 (br, 1H), 1.52-1.39 (m, 2H), 1.13 (br, 1H); $^{13}$CNMR (100 Hz, CDCl$_3$) δ 157.0, 146.5, 143.6, 139.9, 137.7, 131.3, 128.3, 127.9, 127.8, 127.7, 127.6, 123.4, 114.9, 106.7, 79.0, 71.2, 59.0, 49.7, 49.2, 39.6, 28.0, 25.9.

QD-4c was obtained as a yellowish solid in 91% yield from QD-PHN. [α]$_D^{25}$=−304.6 (c 0.98, CHCl$_3$); $^1$HNMR (400 MHz, CDCl$_3$) δ 8.69-8.67 (m, 1H), 8.63-8.61 (m, 1H), 8.46 (d, J=8.0 Hz, 1H), 8.20 (d, 1H, J=2.0 Hz, 1H), 7.78 (d, J=9.2 Hz, 1H), 7.74-7.70 (m, 2H), 7.35 (d, J=5.2 Hz, 1H), 7.25-7.26 (m, 1H), 7.20 (t, J=7.2 Hz, 1H), 6.80 (t, J=7.2 Hz, 1H), 6.64 (s, 1H), 6.50 (d, J=7.2 Hz, 1H), 6.33(s, 1H), 6.23-6.15 (m, 1H), 5.27 (d, J=14.4 Hz, 1H), 5.12 (d, J=17.2 Hz, 1H), 3.58-3.53 (m, 1H), 3.36 (t, J=9.2 Hz, 1H), 3.09-2.99(m, 2H), 2.79-2.68 (m, 2H), 2.30-2.28 (m, 1H), 2.00 (br, 1H), 1.54-1.52 (m, 2H), 1.43-1.34 (m, 1H); $^{13}$CNMR (100 Hz, CDCl$_3$) δ157.0, 149.6, 146.9, 143.7, 142.4, 139.4, 131.9, 131.8, 131.5, 127.3, 127.2, 127.1, 126.6, 126.4, 126.3, 126.1, 124.5, 123.4, 122.8, 122.6, 121.9, 117.5, 115.3, 106.1, 105.0, 76.8, 59.2, 49.7, 49.5, 38.8, 27.4, 25.7, 20.3; IR(CHCl$_3$) ν 3300-2800 (br), 3070, 2939, 2870, 1622, 1506, 1455, 1225, 1115, 753 cm$^{-1}$;

Q-4a was obtained as a white solid in 80% yield from quinine. [α]$_D^{25}$=−162.8 (c 0.93, EtOH); $^1$HNMR (400 MHz, CD$_3$OD) δ 8.58 (d, 1H, J=4.8 Hz), 7.89 (d, J=9.2 Hz, 1H), 7.61 (d, J=4.8 Hz, 1H), 7.32 (dd, J=2.4 Hz, 9.2 Hz, 1H), 7.28 (d, J=2.4 Hz, 1H), 5.69-5.78 (m, 1H), 5.51 (d, J=3.2 Hz, 1H), 4.95 (d, J=17.2 Hz, 1H), 4.88 (d, J=9.2 Hz, 1H), 3.66-3.73 (m, 1H), 3.05-3.13(m, 2H), 2.63-2.74 (m, 2H), 2.34 (br, 1H), 1.80-1.89 (m, 2H), 1.77-1.78 (m, 1H), 1.54-1.61(m, 1H), 1.39-1.46(m, 1H). $^{13}$CNMR (100 Hz, CD$_3$OD) δ 157.9, 149.8, 147.4, 144.0, 142.6, 131.4, 128.4, 123.3, 119.8, 115.0, 105.1, 72.2, 60.9, 57.6, 48.4, 44.2, 40.9, 29.2, 28.1, 21.8; IR(CHCl$_3$) ν 3055, 2937, 2870, 2300-3500(br), 1616, 1457, 1236, 1067 cm$^{-1}$; HRMS (FAB) m/z calcd. for (C$_{19}$H$_{22}$N$_2$O$_2$+H$^+$): 311.1760, found: 311.1761.

Example 4

Preparation of Racemic Adducts (6a-r)

At room temperature to a solution of a nitroalkene (0.1 mmol) in THF (1.0 M) was added dimethyl malonate and a base [for aryl substituted 5a-5o, DABCO (20 mol %) was used; for alkyl substituted 5p-r, KOBu$^t$ (5 mol %) was used]. After the reaction went to completion, the reaction mixture was diluted with ethyl acetate, washed with HCl (1.0 N, aq.) and brine. The organic layer was dried over Na$_2$SO$_4$ and concentrated in vacuo. The residue was purified by flash chromatography.

Example 5

General Procedure for Enantioselective Michael Addition of Dimethyl Malonate to Nitroalkenes

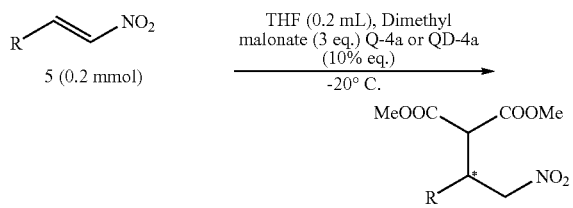

At −20° C., to a solution of a nitroalkene (0.2 mmol) in THF (0.2 mL) was added dimethyl malonate (68 μL, 3 eq.)

and the chiral catalyst (6.2 mg, 10 mol %.). The resulting mixture was kept at −20° C. until 5 is consumed. The reaction mixture was then passed through a plug of silica gel for the removal of the catalyst (eluent: ether or ethyl acetate). The filtrate was concentrated in vacuo and the residue was purified by flash chromatography.

Example 6

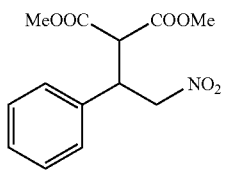

6a (+)-Methyl 2-carbomethoxy-4-nitro-3-phenyl-butyrate (+)-6a

This product was obtained as a colorless oil in 97% yield and 96% ee as determined by HPLC analysis [Daicel chiralpak OD, Hexanes:IPA, 70:30, 0.9 mL/min, λ 220 nm, t (major)=11.6 min, t (minor)=13.7 min] from a reaction catalyzed by Q-4a (10 mol %) at −20° C. for 36 hours. $[\alpha]_D^{23}$=+5.9 (c 1.02, CHCl$_3$) (lit[4]. $[\alpha]_D^{25}$=+4.40 (c 1.02, CHCl$_3$) 93% ee for (S)-isomer); $^1$HNMR (400 MHz, CDCl$_3$) δ 7.34–7.22 (m, 5H), 4.95–4.85 (m, 2H), 4.25 (dt, J=5.2 Hz, 8.8 Hz, 1H), 3.86 (d, J=9.2 Hz, 1H), 3.77 (s, 3H), 3.57 (s, 3H); $^{13}$C NMR (100 Hz, CDCl$_3$) δ 167.8, 167.2, 136.1, 128.9, 128.3, 127.8, 77.3, 54.7, 52.9, 52.7, 42.9; IR(CHCl$_3$) ν 3034, 2957, 1732, 1557, 1435, 1259 cm$^{-1}$; HRMS (CI) m/z calcd. for (C$_{13}$H$_{15}$NO$_6$+H$^+$) 282.0964, found 282.0969.

(−)-Methyl 2-carbomethoxy-4-nitro-3-phenyl-butyrate (−)-6a

This product was obtained as a colorless oil in 99% yield and 93% ee from a reaction catalyzed by QD-4a (10 mol %) at −20° C. for 36 hours.

Example 7

(+)-Methyl 2-carbomethoxy-4-nitro-3-(4-fluoro-phenyl)-butyrate (+)-6b

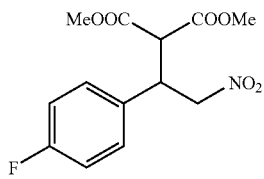

6b

This product was obtained as a colorless oil in 97% yield and 97% ee as determined by HPLC analysis [Chiralcel AD, Hexanes:IPA, 70:30, 1.0 mL/min, λ 220 nm, t (minor)=7.6 min, t (major)=12.4 min] from a reaction catalyzed by Q-4a (10 mol %) at −20° C. for 36 hours. $[\alpha]_D^{23}$=+6.2 (c 1.04, CHCl$_3$); $^1$HNMR (400 MHz, CDCl$_3$) δ 7.22 (dd, J=4.8 Hz, 8.4 Hz, 2H), 7.02 (t, J=8.4 Hz, 2H), 4.91 (dd, J=4.8 Hz, 12.8 Hz, 1H), 4.84 (dd, J=9.2 Hz, 12.8 Hz, 1H), 4.24 (dt, J=5.6 Hz, 9.2 Hz, 1H), 3.82 (d, J=9.2 Hz, 1H), 3.77 (s, 3H), 3.58 (s, 3H); $^{13}$C NMR (100 Hz, CDCl$_3$) δ 167.6, 167.1, 163.7, 161.2, 131.84, 131.80, 129.68, 129.60, 116.1, 115.9, 77.4, 54.6, 53.0, 52.9, 42.2; IR(CHCl$_3$) ν 3011, 2958, 2915, 1733, 1606, 1557, 1436, 1231 cm$^{-1}$; HRMS (CI) m/z calcd. for (C$_{13}$H$_{14}$FNO$_6$+H$^+$): 300.0883, found 300.0886.

(−)-Methyl 2-carbomethoxy-4-nitro-3-(4-fluoro-phenyl)-butyrate (−)-6b

This product was obtained as a colorless oil in 97% yield and 94% ee from a reaction catalyzed by QD-4a (10 mol %) at −20° C. for 36 hours.

Example 8

(+)-Methyl 2-carbomethoxy-4-nitro-3-(4-chloro-phenyl)-butyrate. (+)-6c

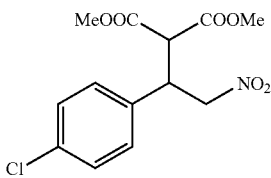

6c

This product was obtained as a white solid in 97% yield and 97% ee as determined by HPLC analysis [Daicel chiralpak OD, Hexanes:IPA, 70:30, 1.0 mL/min, λ 220 nm, t (major)=10.5 min, t (minor)=15.6 min] from a reaction catalyzed by Q-4a (10 mol %) at −20° C. for 36 hours. $[\alpha]_D^{23}$=+7.5 (c 1.08, CHCl$_3$); $^1$HNMR (400 MHz, CDCl$_3$) δ 7.31 (d, J=8.4 Hz, 2H), 7.18 (d, J=8.4 Hz, 2H), 4.91 (dd, J=4.8 Hz, 12.8 Hz, 1H), 4.85 (dd, J=8.4 Hz, 13.6 Hz, 1H), 4.23 (dt, J=4.8 Hz, 9.2 Hz, 1H), 8.83 (d, J=9.2 Hz, 1H), 3.77 (s, 3H), 3.60 (s, 3H); $^{13}$CNMR (100 Hz, CDCl$_3$) δ 167.6, 167.0, 134.6, 134.4, 129.3, 129.2, 77.1, 54.4, 53.0, 52.9, 42.3; IR(CHCl$_3$) ν 3011, 2956, 1736, 1653, 1557, 1494, 1436, 1259, 1015 cm$^{-1}$; HRMS (CI) m/z calcd. for (C$_{13}$H$_{14}$ClNO$_6$+H$^+$): 316.0583, found 316.0582.

(−)-Methyl 2-carbomethoxy-4-nitro-3-(4-chloro-phenyl)butyrate (−)-6c

This product was obtained as a white solid in 97% yield and 94% ee from a reaction catalyzed by QD-4a (10 mol %) at −20° C. for 36 hours.

Example 9

(+)-Methyl 2-carbomethoxy-4-nitro-3-(4-bromo-phenyl)-butyrate (+)-6d

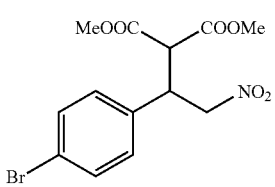

6d

This product was obtained as a white solid in 99% yield and 96% ee as determined by HPLC analysis [Daicel chiralpak OD, Hexanes:IPA, 60:40, 1.0 mL/min, λ 220 nm, t(major)=9.6 min, t(minor)=12.9 min] from a reaction catalyzed by Q-4a (10 mol %) at −20° C. for 36 hours. $[\alpha]_D^{23}$=+6.9 (c 1.12, CHCl$_3$); $^1$HNMR (400 MHz, CDCl$_3$) δ 7.46 (d, J=8.4 Hz, 1H), 7.12, (d, J=8.8 Hz, 1H), 4.91(dd, J=5.6 Hz, 13.6 Hz, 1H), 4.85 (dd, J=9.2 Hz, 13.6 Hz, 1H), 4.22 dt, J=4.8 Hz, 9.2 Hz, 1H), 3.82 (d, J=9.2 Hz, 1H), 3.77 (s, 3H), 3.60 (s, 3H); $^{13}$CNMR (100 Hz, CDCl$_3$) δ 167.6, 167.0, 135.1, 132.2, 129.6, 122.5, 77.1, 54.4, 53.1, 52.9, 42.3; IR(CHCl$_3$) ν 2952, 1734, 1653, 1558, 1507, 1436 cm$^{-1}$; HRMS (CI) m/z calcd. for (C$_{13}$H$_{14}$BrNO$_6$+H$^+$): 360.0083, found 360.0082.

(−)-Methyl 2-carbomethoxy-4-nitro-3-(4-bromo-phenyl)-butyrate (−)-6d

This product was obtained as a white solid in 98% yield and 94% ee from a reaction catalyzed by QD-4a (10 mol %) at −20° C. for 36 hours.

Example 10

(+)-Methyl 2-carbomethoxy-4-nitro-3-(4-methylphe-nyl) butyrate (+)-6e

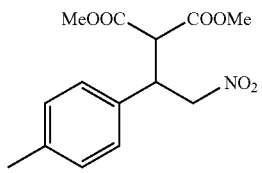

This product was obtained as a colorless oil in 97% yield and 98% ee as determined by HPLC analysis [Daicel chiralpak OD, Hexanes:IPA, 70:30, 1.0 mL/min, λ 220 nm, t(major)=9.8 min, t(minor)=11.0 min] from a reaction catalyzed by Q-4a (10 mol %) at −20° C. for 36 hours. $[\alpha]_D^{23}$=+3.0 (c, 1.40 CHCl$_3$); $^1$HNMR (400 MHz, CDCl$_3$) δ 7.14-7.09 (m, 4H), 4.93-4.82 (m, 2H), 4.20 (dt, J=9.2 Hz, 5.6 Hz, 1H), 3.85 (d, J=9.2 Hz, 1H), 3.76 (s, 3H), 3.58 (s, 3H), 2.30 (s, 3H); $^{13}$CNMR (100 Hz, CDCl$_3$) δ167.9, 167.2, 138.1, 132.9, 129.7, 127.6, 77.5, 54.7, 52.9, 52.8, 42.5, 21.1; IR(CHCl$_3$) ν 3018, 2956, 1736, 1557, 1436, 1259 cm$^{-1}$; HRMS (CI) m/z calcd. for (C$_{14}$H$_{17}$NO$_6$+H$^+$): 296.1134, found 296.1141.

(−)-Methyl 2-carbomethoxy-4-nitro-3-(4-methylphe-nyl)-butyrate (−)-6e

This product was obtained as a colorless oil in 97% yield and 94% ee from a reaction catalyzed by QD-4a (10 mol %) at −20° C. for 44 hours.

Example 11

(+)-Methyl 2-carbomethoxy-4-nitro-3-(4-isopropa-nylphenyl)-butyrate (+)-6f

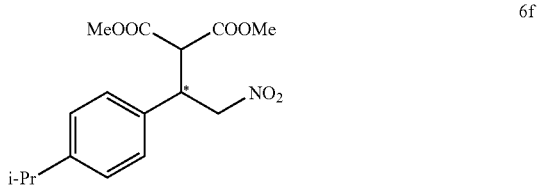

This product was obtained as a white solid in 95% yield and 97% ee as determined by HPLC analysis [Daicel chiralpak OD, Hexanes:IPA, 70:30, 1.0 mL/min, λ 220 nm, t(major)=10.1 min, t(minor)=13.4 min] from a reaction catalyzed by Q-4a (10 mol %) at −20° C. for 36 hours. $[\alpha]_D^{23}$=+4.7 (c 1.08, CHCl$_3$); $^1$HNMR (400 MHz, CDCl$_3$) δ 7.15 (dd, J=8.0 Hz, 14.0 Hz, 4H), 4.94-4.84 (m, 2H), 4.22 (dt, J=5.6 Hz, 8.8 Hz, 1H), 3.85 (d, J=9.2 Hz, 1H), 3.76 (s, 3H), 3.57 (s, 3H), 2.90-2.82 (m, 1H), 1.21(d, J=7.6 Hz, 6H); $^{13}$CNMR (100 Hz, CDCl$_3$) δ167.9, 167.3, 148.9, 133.3, 127.7, 127.0, 77.4, 54.8, 52.9, 52.7, 42.5, 33.6, 23.8; IR(CHCl$_3$) ν 2960, 1735, 1558, 1436, 1259 cm$^{-1}$; HRMS (CI) m/z calcd. for (C$_{16}$H$_{21}$NO$_6$+H$^+$): 324.1447, found 324.1444.

(−)-Methyl 2-carbomethoxy-4-nitro-3-(4-isopropa-nylphenyl)-butyrate (−)-6f

This product was obtained as a white solid in 96% yield and 93% ee from a reaction catalyzed by QD-4a (10 mol %) at −20° C. for 39 hours.

Example 12

(+)-Methyl 2-carbomethoxy-4-nitro-3-(4-methoxy-phenyl)-butyrate (+)-6g

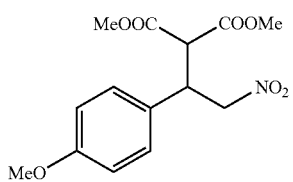

This product was obtained as a colorless oil in 90% yield and 97% ee as determined by HPLC analysis [Chiralcel AD, Hexanes:IPA, 60:40, 1.0 mL/min, t(minor)=7.6 min, t(major)=11.9 min] from a reaction catalyzed by Q-4a (10 mol %) at −20° C. for 44 hours. $[\alpha]_D^{23}$=+5.0 (c 1.18, CHCl$_3$); $^1$HNMR (400 MHz, CDCl$_3$) δ 7.14 (d, J=9.2 Hz, 2H), 6.84 (d, J=8.8 Hz, 2H), 4.89 (dd, J=4.8 Hz, 12.8 Hz, 1H), 4.83 (dd, J=8.8 Hz, 13.6 Hz, 1H), 4.19 (dt, J=4.8 Hz, 13.2 Hz, 1H), 3.82 (d, J=9.2 Hz, 1H), 3.78 (s, 3H), 3.76 (s, 3H), 3.58(s, 3H); $^{13}$CNMR (100 Hz, CDCl$_3$) δ 167.9, 167.3, 159.4, 129.0, 127.8, 114.3, 77.6, 55.2, 54.8, 52.9, 52.8, 42.2; IR(CHCl$_3$) ν 3011, 2957, 2841, 1733, 1557, 1516, 1436, 1258, 1032 cm$^{-1}$; HRMS (CI) m/z calcd for (C$_{14}$H$_{17}$NO$_7$+H$^+$): 312.1070, found 312.1076.

(−)-Methyl 2-carbomethoxy-4-nitro-3-(4-methoxyphenyl)butyrate (−)-6g

This product was obtained as a colorless oil in 94% yield and 95% ee from a reaction catalyzed by QD-4a (10 mol %) at −20° C. for 47 hours.

Example 13

(+)-Methyl 2-carbomethoxy-4-nitro-3-(3-methyl henyl)-butyrate (+)-6h

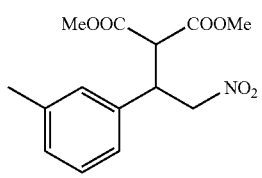

6h

This product was obtained as a colorless oil in 97% yield and 97% ee as determined by HPLC analysis [Daicel chiralpak OD, Hexanes:EPA, 92:8, 0.9 mL/min, λ 220 nm, t (major)=19.8 min, t (minor)=22.2 min] from a reaction catalyzed by Q-4a (10 mol %) at −20° C. for 36 hours. $[\alpha]_D^{23}=+1.0$ (c 1.00, CHCl$_3$); $^1$HNMR (400 MHz, CDCl$_3$) δ 7.21 (t, J=7.2 Hz, 1H), 7.09 (d, J=7.2 Hz, 1H), 7.02 (s, 1H), 7.01 (d, J=7.2 Hz, 1H), 4.94-4.84 (m, 2H), 4.24-4.18 (dt, J=5.6 Hz, 8.4 Hz, 1H), 3.86-3.84 (d, J=8.4 Hz, 1H), 3.76 (s, 3H), 3.58 (s, 3H), 2.32 (s, 3H); $^{13}$CNMR (100 Hz, CDCl$_3$) δ 167.9, 167.2, 138.6, 136.0, 129.1, 128.8, 128.6, 124.6, 77.3, 54.7, 52.9, 52.8, 42.8, 21.3; IR(CHCl$_3$) ν 3029, 2957, 1736, 1557, 1436, 1259 cm$^{-1}$; HRMS (CI) m/z calcd. for $(C_{14}H_{17}NO_6+H^+)$: 296.1134, found 296.1141.

(−)-Methyl 2-carbomethoxy-4-nitro-3-(3-methylphenyl)butyrate (−)-6h

This product was obtained as a colorless oil in 99% yield and 93% ee from a reaction catalyzed by QD-4a (10 mol %) at −20° C. for 36 hours.

Example 14

(−)-Methyl 2-carbomethoxy-4-nitro-3-(2-methylphenyl)-butyrate (−)-6i

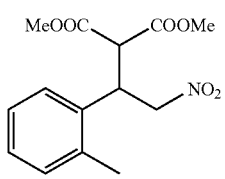

6i

This product was obtained as a colorless oil in 95% yield and 98% ee as determined by HPLC analysis [Chiralcel AD, Hexanes:IPA, 80:20, 1.0 mL/min, λ 220 nm, t(minor)=6.5 min, t(major)=12.2 min] from a reaction catalyzed by Q-4a (10 mol %) at −20° C. for 36 hours. $[\alpha]_D^{23}=-1.6$ (c 1.25, CHCl$_3$); $^1$HNMR (400 MHz, CDCl$_3$) δ 7.17-7.11 (m, 4H), 4.94-4.83 (m, 2H), 4.57 (dt, J=5.6 Hz, 9.2 Hz, 1H), 3.83 (d, J=9.2 Hz, 1H), 3.77 (s, 3H), 3.54 (s, 3H), 2.44 (s, 3H); $^{13}$CNMR (100 Hz, CDCl$_3$) δ 167.9, 167.3, 136.9, 134.4, 131.2, 128.0, 126.5, 125.7, 77.3, 54.4, 52.9, 52.7, 37.7, 19.4; IR(CHCl$_3$) ν 3011, 2956, 1734, 1558, 1436, 1260 cm$^{-1}$; HRMS (CI) m/z calcd for $(C_{14}H_{17}NO_6+H^+)$: 296.1134, found 296.1128.

(+)-Methyl 2-carbomethoxy-4-nitro-3-(2-methylphenyl)butyrate (+)-6i

This product was obtained as a colorless oil in 97% yield and 96% ee from a reaction catalyzed by QD-4a (10 mol %) at −20° C. for 36 hours.

Example 15

(+)-Methyl 2-carbomethoxy-4-nitro-3-(2-fluorophenyl)-butyrate (+)-6i

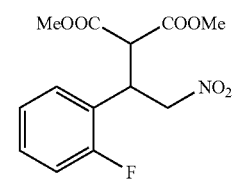

6j

This product was obtained as a colorless oil in 97% yield and 97% ee as determined by HPLC analysis [Chiralcel AD, Hexanes:IPA, 80:20, 1.0 mL/min, λ 220 nm, t(minor)=8.2 min, t(major)=10.1 min] from a reaction catalyzed by Q-4a (10 mol %) at −20° C. for 36 hours. $[\alpha]_D^{23}=+14.6$ (c 1.08, CHCl$_3$); $^1$HNMR (400 MHz, CDCl$_3$) δ 7.32-7.22 (m, 2H), 7.12-7.05 (m, 2H), 4.95-4.93 (d, J=7.2 Hz, 2H), 4.46-4.4 (m, 1H), 4.00 (d, J=9.6 Hz, 1H), 3.78 (s, 3H), 3.56 (s, 3H); $^{13}$CNMR (100 Hz, CDCl$_3$) δ 167.7, 167.1, 162.1, 159.7, 130.47, 130.44, 130.36, 130.3, 124.61, 24.58, 123.0, 122.9, 116.2, 116.0, 76.00, 75.98, 53.05, 52.99, 52.97, 52.81, 38.5. IR(CHCl$_3$) ν 3011, 2958, 2848, 1733, 1557, 1495, 1436, 1259 cm$^{-1}$; HRMS (CI) m/z calcd. for $(C_{13}H_{14}FNO_6+H^+)$: 300.0883, found 300.0879.

(−)-Methyl 2-carbomethoxy-4-nitro-3-(2-fluorophenyl)butyrate (−)-6i

This product was obtained as a colorless oil in 94% yield and 95% ee from a reaction catalyzed by QD-4a (10 mol %) at −20° C. for 36 hours.

Example 16

(+)-Methyl 2-carbomethoxy-4-nitro-3-(2-nitrophenyl)-butyrate (+)-6k

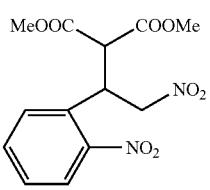

6k

This product was obtained as a yellowish oil in 90% yield and 97% ee as determined by HPLC analysis [Daicel chiralpak OD, Hexanes:IPA, 50:50, 0.9 mL/min, λ 220 nm, t(major)=8.5 min, t(minor)=15.7 min] from a reaction catalyzed by Q-4a (10 mol %) at −55° C. for 69 hours. $[\alpha]_D^{23}$=+18.9 (c 1.04, CHCl$_3$); $^1$HNMR (400 MHz, CDCl$_3$) δ 7.95 (dd, J=1.2 Hz, 8.8 Hz, 1H), 7.60 (dt, J=1.2 Hz, 8.0 Hz, 1H), 7.49 (dt, J=1.2 Hz, 8.0 Hz, 1H), 7.41 (dd, J=1.2 Hz, 8.0 Hz, 1H), 5.17 (dd, J=8.0 Hz, 14.0 Hz, 1H), 5.06 (dd, J=4.0 Hz, 14.0 Hz, 11H), 4.77 (td, J=4.0 Hz, 8.0 Hz, 1H), 4.25 (d, J=8.0 Hz, 1H), 3.77 (s, 3H), 3.65 (s, 3H); $^3$CNMR (100 Hz, CDCl$_3$) δ 167.6, 167.0, 149.8, 133.3, 131.1, 129.3, 128.7, 125.4, 75.9, 53.4, 53.11, 53.08, 37.4; IR(CHCl$_3$) ν 3018, 2958, 1733, 1558, 1436, 1361 cm$^{-1}$; HRMS (CI) m/z calcd. for (C$_{13}$H$_{14}$N$_2$O$_8$+H$^+$): 327.0828, found 327.0822.

(−)-Methyl 2-carbomethoxy-4-nitro-3-(2-nitrophenyl)butyrate (−)-6k

This product was obtained as a yellowish oil in 88% yield and 92% ee from a reaction catalyzed by QD-4a (10 mol %) at −55° C. for 72 hours.

Example 17

(−)-Methyl 2-carbomethoxy-4-nitro-3-(1-naphthyl)butyrate (−)-6l

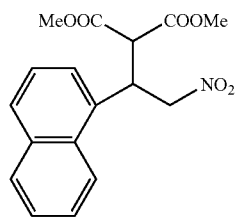

61

This product was obtained as a colorless oil in 99% yield and 98% ee as determined by HPLC analysis [Chiralcel AD, Hexanes:IPA, 80:20, 1.0 mL/min, λ 280 nm, t(minor)=9.5 min, t(major)=13.7 min] from a reaction catalyzed by Q-4a (10 mol %) at −20° C. for 36 hours. $[\alpha]_D^{23}$=−3.8 (c 1.32, CHCl$_3$); $^1$HNMR (400 MHz, CDCl$_3$) δ 8.18 (d, J=8.4 Hz, 1H), 7.88 (d, J=8.8 Hz, 1H), 7.80 (d, J=8.0 Hz, 1H), 7.62 (t, J=8.0 Hz, 1H), 7.53 (t, J=8.0 Hz, 1H), 7.45-7.28 (m, 2H), 5.24-5.05 (m, 3H), 4.13-4.10 (d, J=7.2 Hz, 1H), 3.72 (s, 3H), 3.55 (s, 3H); $^{13}$CNMR (100 Hz, CDCl$_3$) δ167.9, 167.4, 134.1, 132.2, 130.9, 129.2, 128.9, 127.0, 126.1, 125.1, 123.9, 122.1, 76.6, 54.3, 52.9, 36.7; IR(CHCl$_3$) ν 3040, 3011, 2955, 1734, 1557, 1436, 1252, 1028 cm$^{-1}$; HRMS (CI) m/z calcd for (C$_{17}$H$_{17}$NO$_6$+H$^+$): 311.1056, found 311.1055.

(+)-Methyl 2-carbomethoxy-4-nitro-3-(1-naphthyl)butyrate (+)-6l

This product was obtained as a colorless oil in 99% yield and 92% ee from a reaction catalyzed by QD-4a (10 mol %) at −20° C. for 36 hours.

Example 18

(−)-Methyl 2-carbomethoxy-4-nitro-3-(2-thienyl)butyrate (−)-6m

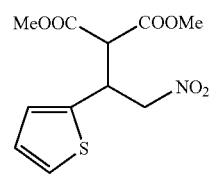

6m

This product was obtained as a colorless oil in 99% yield and 98% ee as determined by HPLC analysis [Chiralcel AD, Hexanes: EPA, 80:20, 1.0 mL/min, λ 220 nm, t(minor)=8.8 min, t(major)=10.6 min] from a reaction catalyzed by Q-4a (10 mol %) at −20° C. for 36 hours. $[\alpha]_D^{23}$=−7.8 (c 2.70, CHCl$_3$); $^1$HNMR (400 MHz, CDCl$_3$) δ 7.24 (d, J=5.2 Hz, 1H), 6.96-6.93 (m, 2H), 4.98-4.89 (m, 2H), 4.60-4.54(dt, J=5.2 Hz, 8.0 Hz, 1H), 3.92(d, J=7.2 Hz, 1H), 3.77(s, 3H), 3.68(s, 3H); $^{13}$CNMR (100 Hz, CDCl$_3$) δ167.6, 167.1, 138.3, 127.1, 126.7, 125.6, 77.8, 55.2, 53.1, 53.0, 38.3; IR(CHCl$_3$) ν 3099, 3003, 2957, 1733, 1557, 1436, 1264 cm$^{-1}$; HRMS (CI) m/z calcd. for (C$_{11}$H$_{13}$NO$_6$S+H$^+$): 288.0528, found 288.0530.

(+)-Methyl 2-carbomethoxy-4-nitro-3-(2-thienyl)butyrate (+)-6m

This product was obtained as a colorless oil in 96% yield and 95% ee from a reaction catalyzed by QD-4a (10 mol %) at −20° C. for 44 hours.

Example 19

(−)-Methyl 2-carbomethoxy-4-nitro-3-(2-furyl)-butyrate (−)-6n

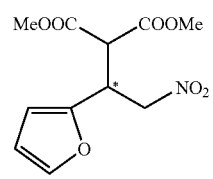

6n

This product was obtained as a yellowish oil in 97% yield and 98% ee as determined by HPLC analysis [Daicel chiralpak OD, Hexanes:IPA, 60:40, 1.0 mL/min, λ 220 nm, t(major)=6.2 min, t(minor)=14.9 min] from a reaction catalyzed by Q-4a (10 mol %) at −20° C. for 36 hours. $[\alpha]_D^{23}$=−4.9 (c 1.10, CHCl$_3$); $^1$HNMR (400 MHz, CDCl$_3$) δ 7.35 (d, J=1.6 Hz, 1H), 6.30 (dd, J=1.6 Hz, 3.2 Hz, 1H), 6.23 (d, J=3.2 Hz), 4.96-4.86 (m, 2H), 4.39 (dt, J=4.8 Hz, 8.0 Hz, 1H), 3.95 (d, J=8.0 Hz, 1H), 3.77(s, 3H), 3.70(s, 3H); $^{13}$CNMR (100 Hz, CDCl$_3$) δ 167.5, 167.2, 149.3, 142.8, 110.5, 108.4, 75.2, 53.03, 52.99, 52.5, 36.7; IR(CHCl$_3$) ν 3018, 2958, 1733, 1558, 1436, 1263, 1014 cm$^{-1}$; HRMS (CD) m/z calcd. for (C$_{11}$H$_{13}$NO$_7$+H$^+$): 272.0770, found 272.0768.

(+)-Methyl 2-carbomethoxy-4-nitro-3-(2-furyl)-butyrate (+)-6n

This product was obtained as a yellowish oil in 99% yield and 96% ee from a reaction catalyzed by QD-4a (10 mol %) at −20° C. for 36 hours.

Example 20

(+)-Methyl 2-carbomethoxy-4-nitro-3-(3-pyridinyl)-butyrate (+)-6o

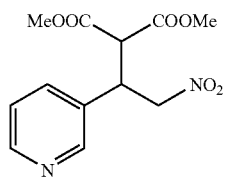

6o

This product was obtained as a white solid in 98% yield and 96% ee as determined by HPLC analysis [Chiralcel AD, Hexanes:IPA, 60:40, 1.0 mL/min, λ 220 nm, t(minor)=6.6 min, t(major)=9.2 min] from a reaction catalyzed by Q-4a (10 mol %) at −20° C. for 36 hours. $[α]_D^{23}$=+3.3 (c 1.30, CHCl$_3$); $^1$HNMR (400 MHz, CDCl$_3$) δ: 8.56 (dd, J=1.6 Hz, 4.8 Hz, 1H), 8.54 (d, J=2.8 Hz, 1H), 7.61(dt, J=8.0 Hz, 2.0 Hz, 1H), 7.28 (dd, J=4.8 Hz, 8.0 Hz, 1H), 4.99-4.88 (m, 2H), 4.28 (dt, J=5.2 Hz, 9.2 Hz, 1H), 3.88 (d, J=9.2 Hz, 1H), 3.78 (s, 3H), 3.61 (s, 3H); $^{13}$CNMR (100 Hz, CDCl$_3$) δ167.4, 166.9, 149.8, 149.6, 135.3, 131.9, 123.6, 76.7, 54.1, 53.2, 53.0, 40.5; IR(CHCl$_3$) ν 3025, 2957, 1733, 1558, 1435, 1265, 1025 cm$^{-1}$; HRMS (CD) m/z calcd. for (C$_{12}$H$_{14}$N$_2$O$_6$+H$^+$): 283.0930, found 283.0923.

(−)-Methyl 2-carbomethoxy-4-nitro-3-(3-pyridinyl) butyrate (−)-6o

This product was obtained as a white solid in 99% yield and 92% ee from a reaction catalyzed by QD-4a (10 mol %) at −20° C. for 36 hours.

Example 21

(+)-Methyl 2-carbomethoxy-3-nitromethyloctanoate (+)-6p

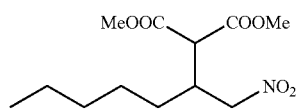

6p

This product was obtained as a colorless oil in 81% yield and 94% ee as determined by HPLC analysis [Daicel chiralpak OD, Hexanes:IPA, 90:10, 1.0 mL/min, λ 215 nm, t (major)=6.1 min, t (minor)=12.3 min] from a reaction catalyzed by Q-4a (10 mol %) at −20° C. for 72 hours. $[α]_D^{23}$=+7.6 (c 1.75, CHCl$_3$); $^1$HNMR (400 MHz, CDCl$_3$) δ 4.71 (dd, J=5.6 Hz, 13.2 Hz, 1H), 4.53 (dd, J=6.8 Hz, 13.6 Hz, 1H), 3.77 (s, 3H), 3.76 (s, 3H), 3.68 (d, J=5.6 Hz, 1H), 2.92-2.87 (m, 1H), 1.48-1.42 (m, 2H), 1.39-1.26 (m, 6H), 0.88 (t, J=6.4 Hz, 3H); $^{13}$CNMR (100 Hz, CDCl$_3$) δ168.4, 168.2, 76.5, 52.8, 52.7, 52.3, 36.9, 31.3, 29.9, 26.2, 22.3, 13.9; IR(CHCl$_3$) ν 2957, 2929, 1735, 1558, 1436, 1160 cm$^{-1}$; HRMS (CD) m/z calcd. for (C$_{12}$H$_{21}$NO$_6$+H$^+$): 276.1447, found 276.1446.

(−)-Methyl 2-carbomethoxy-3-nitromethyloctanoate (−)-6p

This product was obtained as a colorless oil in 82% yield and 91% ee from a reaction catalyzed by QD-4a (10 mol %) at −20° C. for 72 hours.

Example 22

(+)-Methyl 2-carbomethoxy-5-methyl-3-nitromethylhexanoate (+)-6q

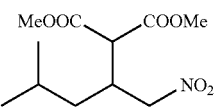

6q

This product was obtained as a colorless oil in 86% yield and 94% ee as determined by HPLC analysis [Daicel chiralpak OD, Hexanes:IPA, 90:10, 1.0 mL/min, λ 215 nm, t(major)=5.6 min, t(minor)=11.2 min] from a reaction catalyzed by Q-4a (10 mol %) at −20° C. for 72 hours. $[α]_D^{23}$=+9.0 (c 2.05, CHCl$_3$); $^1$HNMR (400 MHz, CDCl$_3$) δ 4.68 (dd, J=4.8 Hz, 13.6 Hz, 1H), 4.49 (dd, J=6.4 Hz, 13.6 Hz, 1H), 3.740 (s, 3H), 3.736 (s, 3H), 3.63 (d, J=5.6 Hz, 1H), 2.96-2.91 (m, 1H), 1.65-1.58 (m, 1H), 1.32-1.22 (m, 2H), 0.90-0.88 (m, 6H); $^{13}$CNMR (100 Hz, CDCl$_3$) δ168.4, 168.2, 76.7, 52.8, 52.7, 52.3, 38.9, 34.9, 25.1, 22.3, 22.1; IR(CHCl$_3$) ν 2959, 2878, 1732, 1557, 1436, 1161, 1027 cm$^{-1}$; HRMS (CI) m/z calcd. for (C$_{11}$H$_{19}$NO$_6$+H$^+$): 262.1291, found 262.1297.

(−)-Methyl 2-carbomethoxy-5-methyl-3-nitromethylhexanoate (−)-6q

This product was obtained as a colorless oil in 84% yield and 92% ee from a reaction catalyzed by QD-4a (10 mol %) at −20° C. for 72 hours.

Example 23

(+)-Methyl 2-carbomethoxy-4-nitro-3-cyclohexylbutyrate (+)-6r

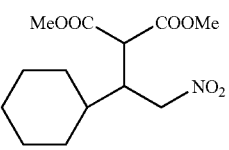

6r

This product was obtained as a colorless oil in 71% yield and 94% ee as determined by HPLC analysis [Daicel chiralpak OD, Hexanes: IPA, 90:10, 1.0 mL/min, λ 215 nm, t(major)=6.0 min, t(minor)=14.8 min] from a reaction catalyzed by Q-4a (20 mol %) at −20° C. for 108 hours.

$[\alpha]_D^{23}$=+12.0 (c 0.95, CHCl$_3$); $^1$HNMR (400 MHz, CDCl$_3$) δ 4.73 (dd, J=4.4 Hz, 14.8 Hz, 1H), 4.62 (dd, J=6.8 Hz, 14.8 Hz, 1H), 3.77-3.75(m, 7H), 2.92-2.88 (m, 1H), 1.78-1.59 (m, 5H), 1.49-1.42 (m, 1H), 1.26-1.10 (m, 3H), 1.07-0.95 (m, 2H); $^{13}$CNMR (100 Hz, CDCl$_3$) δ168.9, 168.6, 75.4, 52.9, 52.7, 50.9, 42.1, 39.6, 30.1, 29.8, 26.22, 26.17, 25.9; IR(CHCl$_3$) ν 2931, 2855, 1735, 1557, 1436, 1160, 1024 cm$^{-1}$; HRMS (CD) m/z calcd. for (C$_{13}$H$_{21}$NO$_6$+H$^+$): 288.1447, found 288.1443.

(−)-Methyl 2-carbomethoxy-4-nitro-3-cyclohexylbutyrate (−)-6r

This product was obtained as a colorless oil in 80% yield and 91% ee from a reaction catalyzed by QD-4a (20 mol %) at −20° C. for 108 hours.

Example 24

General Procedure for Asymmetric Michael Addition of 3a-H to Nitroalkenes 2a-f

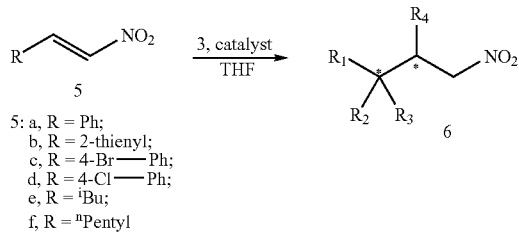

5: a, R = Ph;
b, R = 2-thienyl;
c, R = 4-Br—Ph;
d, R = 4-Cl—Ph;
e, R = $^i$Bu;
f, R = $^n$Pentyl

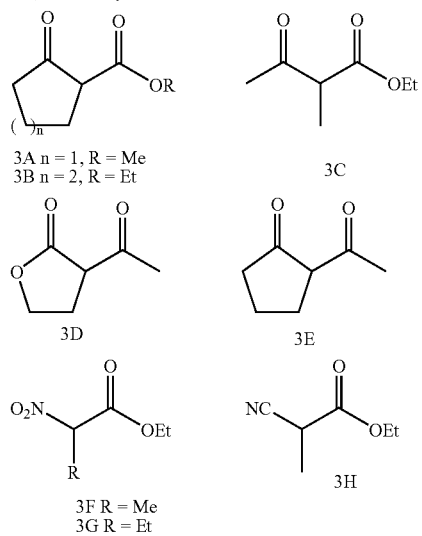

3A n = 1, R = Me
3B n = 2, R = Et

3C

3D

3E

3F R = Me
3G R = Et

3H

Catalysts

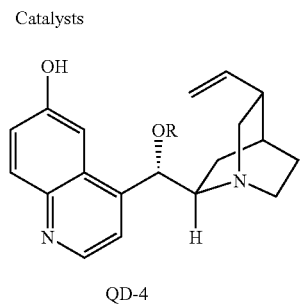

QD-4

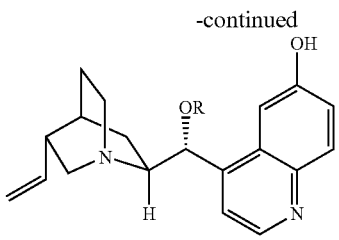

Q-4

Ra: R = H
4b: R = Bn
4c: R =

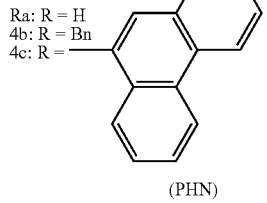

(PHN)

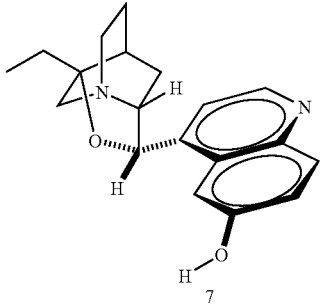

7

For asymmetric conjugate additions generating 6Aa, 6Ba, 6Bb, 6Bc, 6Ea, 0.4 mmol of 3A, 3B and 3E (2.0 equiv.) and 0.2 mmol of 5a-c were used; for reactions generating 6Ca, 0.8 mmol of 3C (4 equiv.) and 0.2 mmol of 5a were used; for other reactions, 0.2 mmol of 3 and 0.4 mmol of 5 were used. Yields were calculated based on the limiting reagent. The choice of using either a donor or acceptor as the limiting reagent is based on how readily the product (6) can be separated from the excessive starting materials (3 or 5). Changing the ratio of 3 and 2 has no impact on both the diastereoselectivity and enantioselectivity of the asymmetric conjugate addition.

When catalyst Q-4b was used, it is first suspended in THF. The resulting suspension was subjected to ultrasound for 10-15 min. and became a milky mixture. To this solution, the starting materials were added according to the procedure described below.

Procedure: At the temperature specified in Tables 3 and 4 to a solution of the limiting reagent (3 or 5, 0.2 mmol) and the chiral catalyst (Q-4, QD-4 or 7, 10-20 mol %.) in THF (0.2 mL) was added the other reagent (5 or 3, 2 or 4 eq.). The resulting mixture was kept at the temperature until the limiting reagent is consumed. The reaction mixture was then passed through a plug of silica gel for the removal of the catalyst. The plug of silica gel was eluted with ether or ethyl acetate (2-3 mL). The combined filtrate was concentrated in vacuo and the residue was subjected to purification by flash chromatography on silica gel.

Example 25

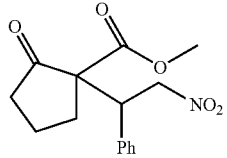
6Aa

Q-4b (10 mol %) catalyzed reaction was run in THF at −60° C. for 48 h to furnish the crude product [dr=95:5, determined by integration of one set of $^1$H NMR signal ($\delta_{major}$ 5.16-5.12 ppm, $\delta_{minor}$ 5.27-5.21 ppm)]. The crude product was purified by flash chromatography (hexane:ethyl acetate=12:1) to give adduct 6Aa as a colorless oil in 94% yield (dr=95:5) and 99% ee (major diastereomer) [determined by HPLC, Chiralcel OD, hexane:isopropanol=80:20, 1.00 mL/min, λ=220 nm, t (major)=11.0 min, t (minor)=17.0 min]. $[\alpha]_D^{25}$=+36.5 (c, 0.84 CHCl$_3$); $^1$H NMR (400 MHz, CDCl$_3$) δ 7.30-7.21 (m, 5H), 5.14 (dd, J=4.0 Hz, 13.6 Hz, 1H), 4.99 (dd, J=11.2 Hz, 2.4 Hz, 1H), 4.05 (dd, J=3.6 Hz, 14.4 Hz, 1H), 3.73 (s, 3H), 2.38-2.28 (m, 2H), 2.04-1.85 (m, 3H), 1.82-1.77 (m, 1H); $^{13}$C NMR (100 MHz, CDCl$_3$) δ 212.2, 169.8, 135.2, 129.2, 128.8, 128.3, 76.4, 62.4, 53.0, 46.1, 37.9, 31.0, 19.3; IR (neat) ν 2957, 1718, 1543, 1496, 1229 cm$^{-1}$; HRMS (CI) m/z calcd for (C$_{15}$H$_{17}$NO$_5$+H$^+$): 292.1185, found: 292.1193.

QD-4c (10 mol %) catalyzed reaction was run at −60° C. for 48 h to furnish the crude product (dr=94:6) and was purified by flash chromatography to give adduct 6Aa in 97% yield (dr=94:6) and 99% ee (major diastereomer).

7 (10 mol %) catalyzed reaction was run at −60° C. for 36 h to furnish the crude product (dr=97:3) and was purified by flash chromatography to give adduct 6Aa in 97% yield (dr=97:3) and 98% ee (major diastereomer).

Example 26

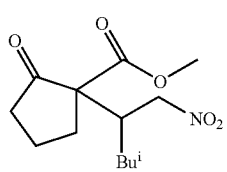
6Ae

Q-4b (10 mol %) catalyzed reaction was run in THF at −60° C. for 96 h to furnish the crude product [dr>98:2, determined by integration of one set of $^1$H NMR signal ($\delta_{major}$ 4.87-4.82 ppm, $\delta_{minor}$ 4.55-4.51 ppm, the minor peak cannot be detected by $^1$H NMR)]. Crude product was purified by flash chromatography (hexane:ethyl acetate=15:1) to give adduct 6 Age as a colorless oil in 87% yield (dr>98:2) and 99% ee (major diastereomer) [determined by HPLC, Chiralcel OD, hexane:isopropanol=95:5, 0.8 mL/min, λ=215 nm, t (major)=11.0 min, t (minor)=16.6 min]. [O]D$^{25}$=+82.5 (c, 0.84 CHCl$_3$); $^1$H NMR (400 MHz, CDCl$_3$) δ 4.86 (dd, J=6.0 Hz, 14.4 Hz, 1H), 4.29 (dd, J=4.4 Hz, 14.4 Hz, 1H), 3.67 (s, 3H), 2.92-2.86 (m, 1H), 2.61-2.55 (m, 1H), 2.46-2.37 (m, 1H), 2.33-2.24 (m, 1H), 2.04-1.88 (m, 3H), 1.56-1.50 (m, 1H), 1.42 (ddd, J=3.6 Hz, 10.4 Hz, 14.0 Hz, 1H), 0.97 (ddd, J=2.4 Hz, 10.4 Hz, 12.8 Hz, 1H), 0.88 (d, J=6.8 Hz, 6H); $^{13}$C NMR (100 MHz, CDCl$_3$) δ 213.2, 169.9, 76.6, 62.9, 52.7, 39.4, 38.4, 38.3, 31.0, 25.6, 23.7, 21.1, 19.4; IR (neat) ν 2959, 1750, 1722, 1557, 1435, 1380, 1230, 1164, 1230 cm$^{-1}$; HRMS (CI) m/z calcd for (C$_{13}$H$_{21}$NO$_5$+H$^+$): 272.1498, found: 272.1497.

Example 27

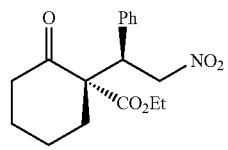
6Ba

Q-4a (10 mol %) catalyzed reaction was run in THF at −20° C. for 72 h to furnish the crude product [dr>98:2, determined by integration of one set of $^1$H NMR signal ($\delta_{major}$ 5.06-5.02 ppm, $\delta_{minor}$ 5.17-5.11 ppm, the minor peak cannot be detected by $^1$H NMR)]. Crude product was purified by flash chromatography (hexane:ethyl acetate=10:1) to give adduct 6Ba as a white solid in 93% yield (dr>98:2) and 99% ee (major diastereomer) [determined by HPLC, Chiralcel OD, hexane:isopropanol=95:5, 0.9 mL/min, λ=220 nm, t (major)=12.3 min, t (minor)=17.0 min]. $[\alpha]_D^{25}$=−91.5 (c, 1.02 CHCl$_3$); $^1$H NMR (400 MHz, CDCl$_3$) δ 7.25-7.12 (m, 5H), 5.04 (dd, J=3.2 Hz, 13.2 Hz, 1H), 4.77 (dd, J=13.2 Hz, 1.6 Hz, 1H), 4.18 (qd, J=1.6 Hz, 7.2 Hz, 2H), 3.97 (dd, J=3.2 Hz, 10.8 Hz, 1H), 2.52-2.39 (m, 2H), 2.08-1.97 (m, 2H), 1.71-1.55 (m, 3H), 1.48-1.40 (m, 1H), 1.23 (t, J=7.2 Hz, 3H); $^{13}$C NMR (100 MHz, CDCl$_3$) δ 207.0, 169.6, 135.3, 129.4, 128.4, 128.1, 77.5, 62.9, 61.9, 47.7, 41.4, 37.0, 27.9, 22.3, 13.9; IR (neat) ν 3032, 2943, 2869, 1712, 1553, 1453, 1378, 1308, 1235 cm$^{-1}$; HRMS (CI) m/z calcd for (C$_{17}$H$_{21}$NO$_5$+H$^+$): 320.1498, found: 320.1502. The relative configuration of 6Ba was determined by X-ray crystallography of (−)-6Ba.

Example 28

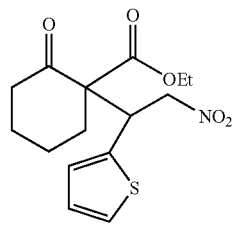
6Bb

Q-4a (10 mol %) catalyzed reaction was run in THF at −20° C. for 74 h to furnish the crude product [dr>98:2, determined by integration of one set of $^1$H NMR signal ($\delta_{major}$ 4.88-4.85 ppm, $\delta_{minor}$ 5.14-5.08 ppm, the minor peak cannot be detected by $^1$H NMR)]. Crude product was purified by flash chromatography (hexane:ethyl acetate=10:1) to give adduct 6Bb as a colorless oil in 91% yield (dr>98:2) and 99% ee (major diastereomer) [determined by HPLC, Chiralcel OD, hexane:isopropanol=95:5, 0.9 mL/min, λ=220 nm, t (major)=14.9 min, t (minor)=24.6 min]. $[\alpha]_D^{25}$=−69.0 (c, 1.06 CHCl$_3$); $^1$H NMR (400 MHz, CDCl₃) δ 7.20 (d, J=4.8 Hz, 1H), 6.89-6.85 (m, 2H), 4.86 (dd, J=3.2 Hz, 13.6 Hz, 1H), 4.77 (dd, J=10.4 Hz, 1H), 4.31 (dd, J=4.0 Hz, 10.4 Hz, 1H), 4.17 (q, J=7.2 Hz, 2H), 2.52 (m, 2H), 2.32-2.28 (m, 1H), 2.01-1.97 (m, 1H), 1.79-1.77 (m, 1H), 1.69-1.56 (m, 3H), 1.22 (t, J=7.2 Hz, 3H); $^{13}$C NMR (100 MHz, CDCl₃) δ 206.9, 169.6, 137.7, 128.4, 126.5, 126.1, 78.7, 63.7, 62.1, 43.3, 41.0, 36.1, 27.5, 22.1, 13.9; IR (neat) ν 2942, 1718, 1702, 1559, 1543, 1524, 1437, 1376, 1232 cm$^{-1}$; HRMS (CI) m/z calcd for (C₁₅H₁₉NO₅S+H⁺): 326.1055, found: 326.1058.

Example 29

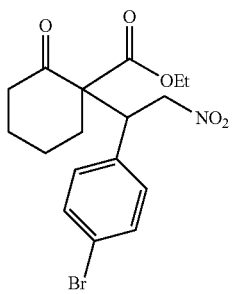

6Bc

Q-4a (10 mol %) catalyzed reaction was run in THF at −20° C. for 74 h to furnish the crude product [dr>98:2, determined by integration of one set of $^1$H NMR signal (δ$_{major}$ 5.01-4.97 ppm, δ$_{minor}$ 5.16-5.10 ppm, the minor peak cannot be detected by $^1$H NMR)]. Crude product was purified by flash chromatography (hexane:ethyl acetate=12:1) to give adduct 6Bc as a colorless oil in 95% yield (dr>98:2) and 99% ee (major diastereomer) [determined by HPLC, Chiralcel OD, hexane:isopropanol=90:10, 0.8 mL/min, λ=220 nm, t (major)=11.4 min, t (minor)=18.6 min]. [α]$_D^{25}$=−74.1 (c, 0.56 CHCl₃); $^1$H NMR (400 MHz, CDCl₃) δ 7.38 (d, J=8.4 Hz, 2H), 7.02 (d, J=8.4 Hz, 2H), 4.98 (dd, J=3.2 Hz, 14.0 Hz, 1H), 4.71 (dd, J=14.0 Hz, 2.4 Hz, 1H), 4.21-4.13 (m, 2H), 3.92 (dd, J=3.2 Hz, 11.6 Hz, 1H), 2.50-2.39 (m, 2H), 2.10-2.05 (m, 1H), 2.02-1.96 (m, 1H), 1.72-1.65 (m, 1H), 1.63-1.50 (m, 2H), 1.46-1.39 (m, 1H), 1.21 (t, J=7.2 Hz, 3H); $^{13}$C NMR (100 MHz, CDCl₃) δ 206.8, 169.5, 134.5, 131.5, 131.2, 122.3, 76.7, 62.7, 62.0, 47.2, 41.3, 37.0, 27.7, 22.3, 13.9; IR (neat) ν 2942, 1716, 1557, 1490, 1436, 1377, 1307, 1234, 1198, 1012 cm⁻; HRMS (CI) m/z calcd for (C₁₇H₂₀BrNO₅+H⁺): 398.0603, found: 398.0604.

QD-4a (10 mol %) catalyzed reaction was run at −20° C. for 72 h to furnish the crude product (dr>98:2) and was purified by flash chromatography to give adduct 6Bc in 96% yield (dr>98:2) and 99% ee (major diastereomer).

7 (10 mol %) catalyzed reaction was run at −20° C. for 60 h to furnish the crude product (dr>98:2) and was purified by flash chromatography to give adduct 6Bc in 97% yield (dr>98:2) and 98% ee (major diastereomer).

Example 30

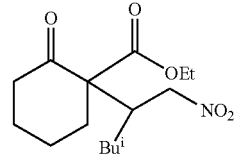

6Be

Q-4c (10 mol %) catalyzed reaction was run in THF at 23° C. for 96 h to furnish the crude product [dr>98:2, determined by integration of one set of $^1$H NMR signal (δ$_{major}$ 4.55-4.50 ppm, δ$_{minor}$ 4.62-4.57 ppm, the minor peak cannot be detected by $^1$H NMR)]. Crude product was purified by flash chromatography (hexane:ethyl acetate=20:1) to give to give adduct 6Be as a colorless oil in 83% yield (dr>98:2) and 99% ee (major diastereomer) [determined by HPLC, Chiralcel OD, hexane:isopropanol=90:10, 0.8 mL/min, λ=215 nm, t (major)=11.0 min, t (minor)=19.2 min]. [α]$_D^{25}$=−33.7 (c, 0.92 CHCl₃); $^1$H NMR (400 MHz, CDCl₃) δ 4.53 (dd, J=4.8 Hz, 14.0 Hz, 1H), 4.30 (dd, J=4.8 Hz, 14.8 Hz, 1H), 4.22 (ddd, J=2.4 Hz, 7.2 Hz, 14.0 Hz, 2H), 2.94 (m, 1H), 2.59 (m, 3H), 2.03 (m, 1H), 1.83 (m, 1H), 1.70-1.61(m, 3H), 1.58-1.51 (m, 1H), 1.43 (ddd, J=4.0 Hz, 10.4 Hz, 14.0 Hz, 1H), 1.30 (t, J=1.30 Hz, 3H), 1.16 (ddd, J=2.4 Hz, 9.6 Hz, 13.6 Hz, 1H), 0.91 (d, J=6.8 Hz, 3H), 0.89 (d, J=6.4 Hz, 3H); $^{13}$C NMR (100 MHz, CDCl₃) δ 207.3, 170.9, 77.9, 64.4, 61.8, 41.1, 39.9, 38.8, 33.9, 27.1, 25.9, 23.7, 22.2, 21.2, 14.0; IR (neat) ν 2957, 2896, 1713, 1554, 1465, 1439, 1379, 1235, 1208, 1137, 1020 cm$^{-1}$; HRMS (CI) m/z calcd for (C₁₅H₂₅NO₅+H⁺): 300.1811, found: 300.1811.

Example 31

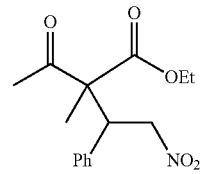

6Ca

Q-4c (15 mol %) catalyzed reaction was run in THF at −20° C. for 63 h to furnish the crude product [dr=91:9, determined by integration of one set of $^1$H NMR signal (δ$_{major}$ 2.17 ppm, δ$_{minor}$ 2.12 ppm)]. Crude product was purified by flash chromatography (hexane:ethyl acetate=13:1) to give to give adduct 6Ca as a colorless oil in 73% yield (pure diastereomer) and 99% ee (major diastereomer) [determined by HPLC, Chiralcel OD, hexane:isopropanol=90:10, 0.9 mL/min, λ=220 nm, t (major)=10.3 min, t (minor)=26.6 min]. [α]$_D^{25}$=−69.9 (c, 0.93 CHCl₃); $^1$H NMR (400 MHz, CDCl₃) δ 7.33-7.27 (m, 3H0, 7.14-7.12 (m, 2H), 4.97 (dd, J=10.4 Hz, 13.2 Hz, 1H), 4.89 (dd, J=3.6 Hz, 13.2 Hz, 1H), 4.28 (q, J=7.2 Hz, 2H), 4.14 (dd, J=4.0 Hz, 10.4 Hz, 1H), 2.17 (s, 3H), 1.31 (t, J=7.2 Hz, 3H), 1.23 (s, 3H); $^{13}$C NMR (100 MHz, CDCl₃) δ 204.2, 171.2, 135.3, 128.9, 128.7, 128.3, 77.5, 62.4, 62.1, 47.7, 26.4, 20.0, 13.9; IR (neat) ν 2986, 1717, 1557, 1457, 1378, 1236 cm$^{-1}$; HRMS (CI) m/z calcd for (C₁₅H₁₉NO₅+H⁺): 294.1341, found: 294.1343.

QD-4c (10 mol %) catalyzed reaction was run at −20° C. for 60 h to furnish the crude product (dr=82:18) and was purified by flash chromatography to give adduct 6Ca in 70% yield (pure diastereomer) and 99% ee (major diastereomer).

7 (10 mol %) catalyzed reaction was run at −20° C. for 64 h to furnish the crude product (dr=89:11) and was purified by flash chromatography to give adduct 6Ca in 75% yield (pure diastereomer) and 96% ee (major diastereomer).

Example 32

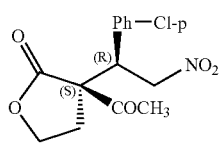

(−)-6Dd

Q-4b (10 mol %) catalyzed reaction was run in THF at −60° C. for 44 h to furnish the crude product [dr=98:2, determined by integration of one set of $^1$H NMR signal ($\delta_{major}$ 2.31 ppm, $\delta_{minor}$ 2.43 ppm)]. Crude product was purified by flash chromatography (hexane:ethyl acetate=6:1) to give to give adduct (−)-6Dd as a white solid in 87% yield (dr=98:2) and 99% ee (major diastereomer) [determined by HPLC, Chiralcel OD, hexane:isopropanol=60:40, 1.0 mL/min, λ=220 nm, t (major)=10.3 min, t (minor)=20.0 min]. $[\alpha]_D^{25}$=−23.5 (c, 1.18 CHCl$_3$); $^1$H NMR (400 MHz, CDCl$_3$) δ 7.32 (dt, J=8.4 Hz, 1.6 Hz, 2H), 7.20 (dt, J=8.8 Hz, 1.6 Hz, 2H), 5.00 (dd, J=11.6 Hz, 13.6 Hz, 1H), 4.70 (dd, J=3.2 Hz, 13.6 Hz, 1H), 4.29 (dd, J=3.2 Hz, 11.6 Hz, 1H), 4.10 (dt, J=6.0 Hz, 9.2 Hz, 1H), 3.47 (dt, J=6.0 Hz, 9.2 Hz, 1H), 2.55 (ddd, J=6.0 Hz, 8.8 Hz, 14.0 Hz, 1H), 2.31 (s, 3H), 2.20 (ddd, J=6.0 Hz, 8.8 Hz, 14.0 Hz, 1H); $^{13}$C NMR (100 MHz, CDCl$_3$) δ 200.9, 175.0, 135.2, 132.7, 130.0, 129.6, 76.2, 66.2, 62.8, 45.6, 29.8, 26.5; IR (neat) ν 2994, 2923, 1755, 1716, 1555, 1494, 1434, 1417, 1378, 1175 cm$^{-1}$; HRMS (CI) m/z calcd for (C$_{14}$H$_{14}$ClNO$_5$+H$^+$): 312.0639, found: 312.0630. The absolute configuration of (−)-5Dd was determined by X-ray crystallography of (−)-5Dd.

QD-4c (10 mol %) catalyzed reaction was run at −60° C. for 40 h to furnish the crude product (dr=97:3) and was purified by flash chromatography to give adduct (+)-6Dd in 92% yield (dr=97:3) and 98% ee (major diastereomer).

7 (10 mol %) catalyzed reaction was run at −60° C. for 36 h to furnish the crude product (dr=97:3) and was purified by flash chromatography to give adduct (+)-6Dd in 92% yield (dr 97:3) and 98% ee (major diastereomer).

Example 33

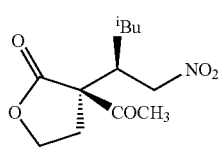

6De

Q-4c (10 mol %) catalyzed reaction was run in THF at −60° C. for 48 h to furnish the crude product [dr=421, determined by integration of one set of $^1$H NMR signal ($\delta_{major}$ 2.37 ppm, $\delta_{minor}$ 2.40 ppm)]. Crude product was purified by flash chromatography (hexane:ethyl acetate=10:1) to give adduct 6De as a white solid in 82% yield (dr=98:2) and 99% ee (major diastereomer) [determined by HPLC, Chiralcel OD, hexane:isopropanol=90:10, 0.8 mL/min, λ=215 nm, t (major)=20.4 min, t (minor)=51.0 min]. $[\alpha]_D^{25}$=+80.9 (c, 0.92 CHCl$_3$); $^1$H NMR (400 MHz, CDCl$_3$) δ 4.44 (dd, J=4.4 Hz, 13.6 Hz, 1H), 4.38 (dd, J=6.4 Hz, 1H), 4.33 (dt, J=2.0 Hz, 9.2 Hz, 1H), 4.12 (dt, J=7.6 Hz, 9.6 Hz, 1H), 3.29-3.22 (m, 1H), 2.78 (ddd, J=2.4 Hz, 7.2 Hz, 13.2 Hz, 1H), 2.35 (s, 3H), 1.99 (td, J=9.6 Hz, 12.8 Hz, 1H), 1.56-1.50 (m, 1H), 1.26 (ddd, J=4.4 Hz, 11.2 Hz, 14.8 Hz, 1H), 0.96 (ddd, J=2.8 Hz, 10.8 Hz, 14.0 Hz, 1H), 0.89 (d, J=6.0 Hz, 3H), 0.87 (d, J=6.0 Hz, 3H); $^{13}$C NMR (100 MHz, CDCl$_3$) δ 200.8, 173.8, 76.7, 66.4, 65.1, 39.0, 37.2, 26.2, 25.4, 25.1, 23.6, 21.1; IR (neat) ν 2958, 2930, 1758, 1715, 1560, 1448, 1380, 1223, 1159, 1022 cm$^{-1}$; HRMS (CI) m/z calcd for (C$_{12}$H$_{19}$NO$_5$+H$^+$): 258.1341, found: 258.1341. The relative configuration of 6De was determined by X-ray crystallography of (+)-6De.

Example 34

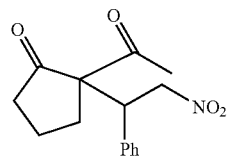

6Ea

Q-4b (10 mol %) catalyzed reaction was run in THF at −60° C. for 48 h to furnish the crude product [dr=86:14, determined by integration of one set of $^1$H NMR signal ($\delta_{major}$ 4.39-4.35 ppm, $\delta_{minor}$ 4.28-4.24 ppm)]. Crude product was purified by flash chromatography (hexane:ethyl acetate=12:1) to give adduct 6Ea as a white solid (pure diastereomer) in 76% yield (pure diastereomer) and 99% ee (major diastereomer) [determined by HPLC, Chiralcel OD, hexane:isopropanol=80:20, 1.0 mL/min, λ=220 nm, t (major)=12.6 min, t (minor)=53.3 min]. $[\alpha]_D^{25}$=−43.3 (c, 1.11 CHCl$_3$); $^1$H NMR (400 MHz, CDCl$_3$) δ 7.31-7.22 (m, 5H), 4.84 (dd, J=11.6 Hz, 13.2 Hz, 1H), 4.48 (dd, J=4.4 Hz, 14.0 Hz, 1H), 4.36 (dd, J=3.6 Hz, 11.6 Hz, 1H), 2.57-2.51 (m, 1H), 2.30 (s, 3H), 2.21-2.12 (m, 1H), 1.99-1.91 (m, 1H), 1.76-1.64 (m, 3H); $^{13}$C NMR (100 MHz, CDCl$_3$) δ 213.1, 202.7, 134.2, 129.4, 128.8, 128.4, 75.5, 71.1, 46.3, 38.6, 27.2, 26.6, 19.4; IR (neat) ν3033, 2971, 1740, 1702, 1554, 1378, 1140 cm$^{-1}$; HRMS (CI) m/z calcd for (C$_{15}$H$_{17}$NO$_4$+H$^+$): 276.12136, found: 276.1238.

QD-4c (10 mol %) catalyzed reaction was run at −60° C. for 48 h to furnish the crude product (dr=88:12) and was purified by flash chromatography to give adduct 6Ea in 70% yield (pure diastereomer) and 98% ee (major diastereomer).

7 (10 mol %) catalyzed reaction was run at −60° C. for 48 h to furnish the crude product (dr=90:10) and was purified by flash chromatography to give adduct 6Ea in 79% yield (pure diastereomer) and 96% ee (major diastereomer).

Example 35

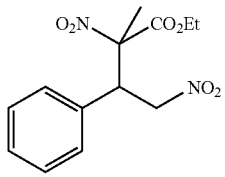

6Fa

Q-4a (10 mol %) catalyzed reaction was run in THF at −20° C. for 2.5 days to furnish the crude product [dr=92:8, determined by $^1$H NMR peaks at 5.04-5.17 ppm and 4.96-5.00 ppm]. Pure major diastereomer (−)-6Fa was obtained by flash chromatography (hexane:ethyl acetate=15:1-10:1) as white solid in 78% yield and 92% ee [determined by HPLC, Chiralcel OD, hexane:isopropanol=80:20, 1.00 mL/min, λ=220 nm, t (major)=7.9 min, t (minor)=18.8 min]. $[\alpha]_D^{25}$=−50.2 (c 0.93, CHCl$_3$); $^1$H NMR (400 MHz, CDCl$_3$) δ 1.31 (t, J=7.6 Hz, 3H), 1.65 (s, 3H), 4.33 (q, J=6.8 Hz, 2H), 4.41 (dd, J=3.6, 10.4 Hz, 1H), 5.07 (dd, J=10.4, 14.0 Hz, 1H), 5.14 (dd, J=3.6, 14.0 Hz, 1H), 7.12-7.15 (m, 2H), 7.35-7.37 (m, 3H); $^{13}$C NMR (101 MHz, CDCl$_3$) δ 13.74, 21.88, 48.65, 63.80, 77.00, 93.78, 128.88, 128.29, 129.34, 132.39, 166.57; IR (neat) ν 1753, 1561, 1549 cm$^{-1}$; HRMS (CI/MH+) Calcd for C$_{13}$H$_{17}$N$_2$O$_6$: 297.1084, found 297.1087.

QD-4a (10 mol %) catalyzed reaction was run in THF at −20° C. for 2.5 days to furnish the crude product (dr=89:11). Major diastereomer (+)-6Fa was obtained by flash chromatography as a white solid in 74% yield and 89% ee.

7 (10 mol %) catalyzed reaction was run in THF at −20° C. for 2.5 days to furnish the crude product (dr=95:5). Major diastereomer (+)-6Fa was obtained by flash chromatography as a white solid in 74% yield and 88% ee.

Example 36

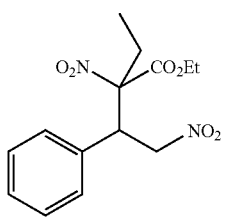

6Ga

Q-4a (20 mol %) catalyzed reaction was run in THF at −50° C. for 6 days to furnish crude product [dr=95:5, determined by $^1$H NMR peaks at 4.58-4.62 ppm (minor) and 5.17-5.21 ppm (major)]. Pure product was obtained by flash chromatography (hexane:ethyl acetate=20:1-15:1) as a white solid mixture of two diastereomers (dr=95:5) in 77% yield and 96% ee (major isomer) [determined by HPLC, Chiralcel OD, hexane:isopropanol=80:20, 1.00 ml/min, λ=220 nm, t (major)=27.3 min, t (minor)=31.5 min]. After recrystalization in Et$_2$O, pure diastereomer (−)-6Ga was obtained in 50% yield and more than 99% ee. $[\alpha]_D^{25}$=−68.1 (c 0.88, CHCl$_3$); $^1$H NMR (400 MHz, CDCl$_3$) δ 0.98 (t, J=8.0 Hz, 3H), 1.34 (t, J=7.2 Hz, 3H), 1.76-1.85 (m, 1H), 2.04-2.13 (m, 1H), 4.33-4.40 (m, 2H), 4.43 (dd, J=3.2, 10.8 Hz, 1H), 4.97 (dd, J=10.4, 13.2 Hz, 1H), 7.08-7.10 (m, 2H), 7.31-7.35 (m, 3H); $^{13}$C NMR (101 MHz, CDCl$_3$) δ 8.45, 13.89, 27.79, 46.74, 63.57, 77.72, 97.46, 128.52, 129.30, 129.33, 132.51, 165.65; IR (neat) ν 1753, 1560,1552 cm$^{-1}$; HRMS (CI/MH+) Calcd for C$_{14}$H$_{19}$N$_2$O$_6$: 311.1246, found 311.1243.

Example 37

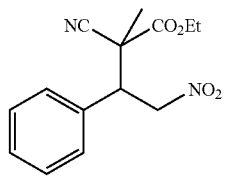

6Ha

Q-4b (20 mol %) catalyzed reaction was run in THF at −50° C. for 6 days to furnish the crude product [dr>98:2, determined by $^1$H NMR peaks at 4.82-4.86 ppm and 4.98-5.04 ppm]. Pure major diastereomer (−)-6Ha was obtained by flash chromatography (hexane:ethyl acetate=10:1-8:1) as colorless oil in 78% yield and 99% ee [determined by HPLC, Chiralcel OD, hexane:isopropanol=80:20, 1.00 mL/min, λ=220 nm, t (major)=32.5 min, t (minor)=21.5 min]. $[\alpha]_D^{25}$=−38.0 (c 2.10, CHCl$_3$); $^1$H NMR (400 MHz, CDCl$_3$) δ 1.34 (t, J=7.2 Hz, 3H), 1.38 (s, 3H), 4.02 (dd, J=5.2, 10.4 Hz, 1H), 4.27-4.35 (m, 2H), 4.79 (dd, J=4.8, 13.2 Hz, 1H), 4.98 (dd, J=10.0, 13.6 Hz, 1H), 7.37 (brs, 5H); $^{13}$C NMR (101 MHz, CDCl$_3$) δ 13.86, 22.84, 46.58, 48.34, 63.84, 76.44, 117.81, 128.69, 129.21, 129.31, 133.04, 168.14; IR (neat) ν 1739, 1556 cm$^{-1}$; HRMS (CI/MH$^+$) Calcd for C$_{14}$H$_{17}$N$_2$O$_4$: 277.1197, found 277.1188.

QD-4a (10 mol %) catalyzed reaction was run in THF at −20° C. for 2.5 days to furnish the crude product (dr=86:14). Major diastereomer (+)-6Ha was obtained by flash chromatography as colorless oil in 76% yield and 95% ee.

7 (10 mol %) catalyzed reaction was run in THF at −20° C. for 2.5 days to furnish the crude product (dr=86:14). Major diastereomer (+)-6Ha was obtained by flash chromatography as colorless oil in 74% yield and 88% ee.

Example 38

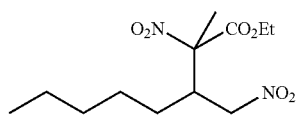

6Ff

Q-4a (10 mol %) catalyzed reaction was run in THF at −20° C. for 3.5 days to furnish crude product [dr=93:7, determined by $^1$H NMR peaks 3.40 ppm (minor), 3.20-3.25 ppm (major)]. Pure major diastereomer (+)-6Ff was obtained by flash chromatography (hexane:ethyl acetate=50:1-20:1) as a colorless oil in 78% yield and 92% ee [determined by HPLC, Chiralcel OD, hexane:isopropanol=99:1, 1.00 mL/min, λ=220 nm, t (major)=31.6 min, t (minor)=53.2 min]. $[\alpha]_D^{25}$=+19.3 (c 2.15, CHCl$_3$); $^1$H NMR (400 MHz, CDCl$_3$) δ 0.88 (t, J=6.8 Hz, 3H), 1.24-1.42 (m, 10H), 1.55-1.61 (m, 1H), 1.86 (s, 3H), 3.20-3.25 (m, 1H), 4.30 (q, J=7.2 Hz, 2H), 4.46 (dd, J=6.4, 14.8 Hz, 1H), 4.77 (dd, J=3.6, 14.4 Hz, 1H); $^{13}$C NMR (101 MHz, CDCl$_3$) δ 13.68, 13.82, 21.02, 22.23, 26.63, 29.34, 31.49, 42.47, 63.57, 77.00, 94.69, 166.47; IR (neat) ν 1751, 1560 cm$^{-1}$; HRMS (CI/MH$^+$) Calcd for C$_{12}$H$_{23}$N$_2$O$_6$: 291.1561, found 291.1556.

Q-4a (10 mol %) catalyzed reaction was run in THF at −20° C. for 3.5 days to furnish crude product [dr=93:7, determined by $^1$H NMR peaks at 2.93-2.96 ppm (minor) and 2.82-2.88 ppm (major)].

xample 39

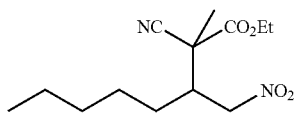

6Hf

Pure product 6Hf was obtained by flash chromatography (hexane:ethyl acetate=50:1-30:1) as a colorless oil mixture of two diastereomers (dr=93:7) in 76% yield and 98% ee (major isomer) [determined by HPLC, Chiralcel OD, hexane:isopropanol=99:1, 0.50 m/min, λ=220 nm, t (major) =45.8 min, t (minor)=66.2 min]. [α]$_D^{25}$=+17.3 (c 1.81, CHCl$_3$); $^1$H NMR of major diastereomer (400 MHz, CDCl$_3$) δ 0.90 (t, J=6.0 Hz, 3H), 1.26-1.50 (m, 10H), 1.67 (s, 3H), 1.70-1.76 (m, 1H), 2.82-2.88 (m, 1H), 4.28 (q, J=6.8 Hz, 2H), 4.43 (dd, J=6.4, 14.0 Hz, 1H), 4.64 (dd, J=4.8, 14.0 Hz, 1H); $^{13}$C NMR of major diastereomer (101 MHz, CDCl$_3$) δ 13.84, 21.64, 22.27, 26.49, 29.33, 31.48, 42.97, 46.87, 63.47, 76.04, 76.68, 118.34, 168.03; IR (neat) ν 1743, 1560 cm$^{-1}$; HRMS (CI/MH+) Calcd for C$_{13}$H$_{23}$N$_2$O$_4$: 271.1652, found 271.1658.

Example 40

Kinetic Data

The kinetic parameters of reactions involving tertiary nucleophiles and nitroalkenes were determined by in situ monitoring of the consumption of nitroalkenes (at peak 1522 cm$^{-1}$) by the use of a ReactIR 1000 instrument. ReactIR 1000 fitted with a 5/8" Dicomp Probe, running software version 2.1a. A mixture of nitroalkene (5a) (1.0 mmol) and Q-4c (2.5-12.5 mol %) in anhydrous THF (1.0 mL) was stirred at −30° C. for 5 minutes, and then pre-cooled methyl 2-oxocyclopentane carboxylate (3A, 0.65 ml, 5 esq.) was introduced in one portion via a syringe. The resulting reaction mixture was monitored every 2 seconds for 25 minutes.

Figure 13:
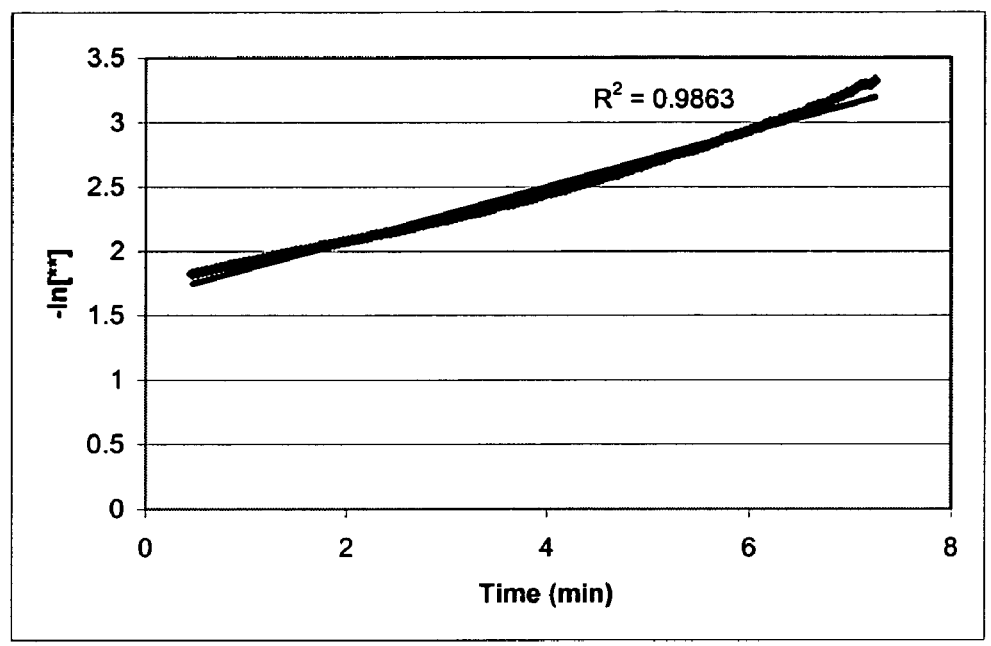

Order in nitroalkene (5a) was established by using a large excess of methyl 2-oxocyclopentane carboxylate (3A, 5 equiv) and 10 mol % Q-4c. Plotting in ln[5a] versus time gave a straight line (R$^2$=0.9863, FIG. 13), thus establishing a first-order dependence on nitroalkene (5a).

Figure 14:
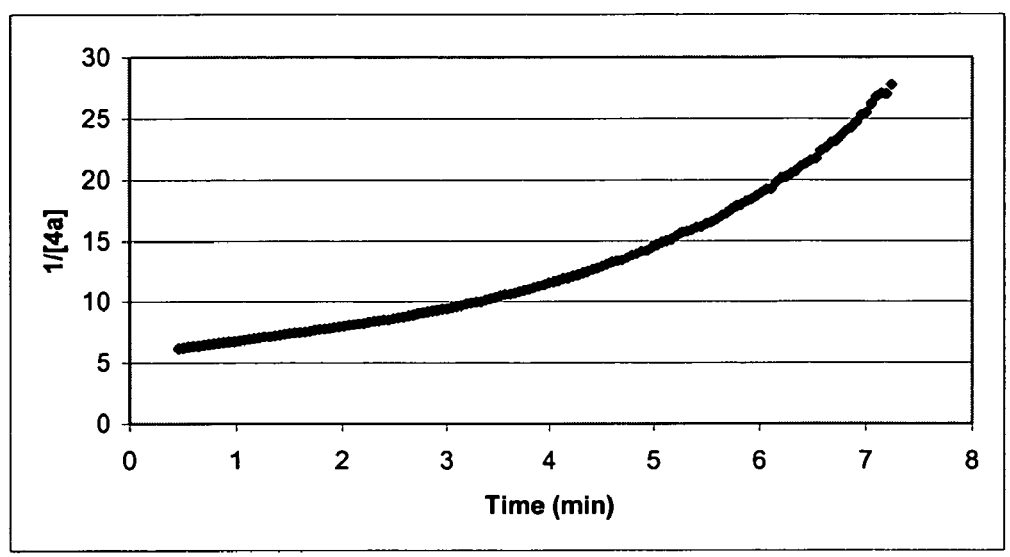

Order in methyl 2-oxocyclopentane carboxylate (3A) was established by using a large excess of nitroalkene (5a, 5 equiv) and 10 mol % Q-4c. Plotting in ln[3A] versus time gave a straight line (R$^2$=0.9952, FIG. 14), thus establishing a first-order dependence on 3A.

Figure 15:
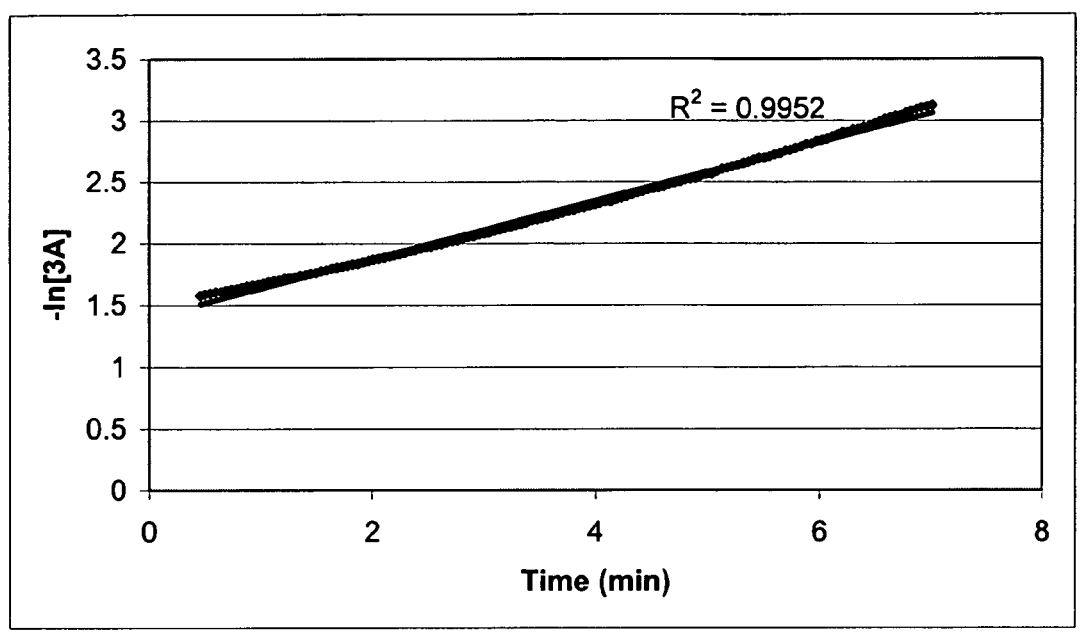
FIG. 15 depicts the kinetic determination of the order of methyl 2-oxocyclopentane carboxylate (3A). The graph shows a linear relationship between ln[3A] and time indicating the reaction is first order in 3A.
Figure 16:
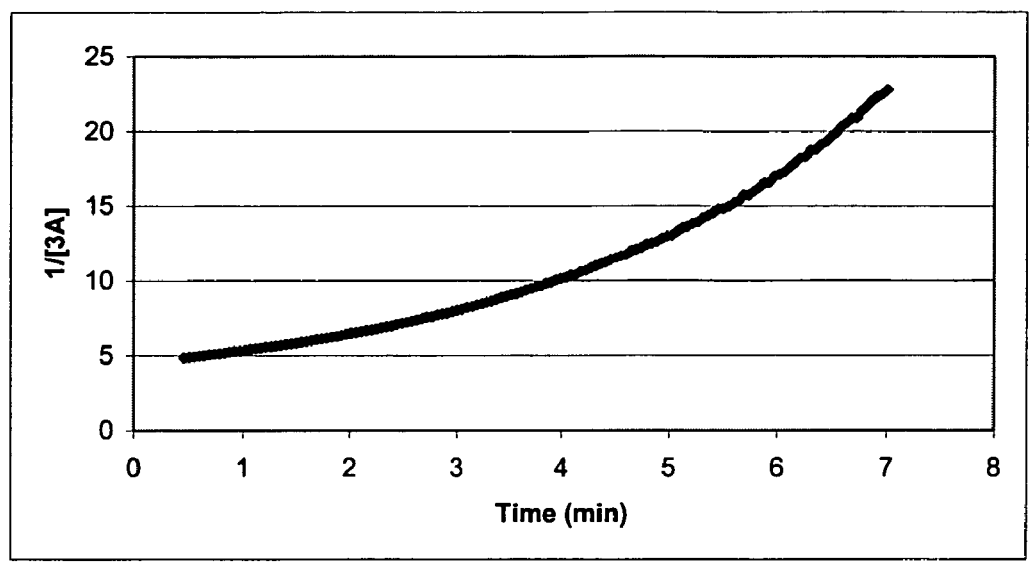
FIG. 16 depicts the kinetic determination of the order of methyl 2-oxocyclopentane carboxylate (3A). The graph shows a nonlinear relationship between 1/[3A] and time indicating the reaction is not second order in 3A.
Figure 17:
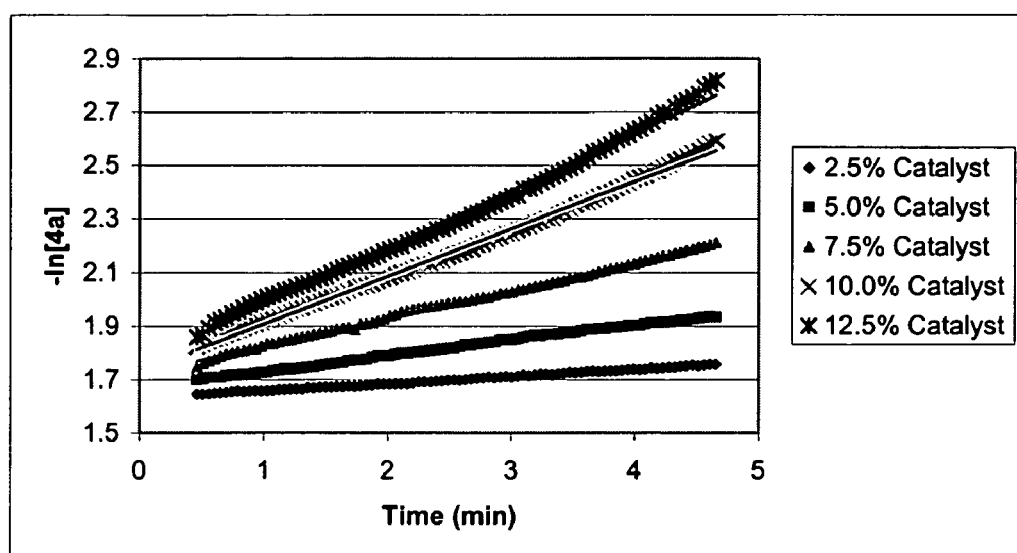
FIG. 17 depicts kinetic profiles for the catalyst Q-4c. Catalyst 2.5 mol %, $k_{obs}=0.0268$, $R^2=0.9974$; Catalyst 5.0 mol %, $k_{obs}=0.0661$, $R^2=0.9976$; Catalyst 7.5 mol %, $k_{obs}=0.1035$, $R^2=0.9978$; Catalyst 10.0 mol %, $k_{obs}=0.1775$, $R^2=0.9965$; Catalyst 12.5 mol %, $k_{obs}=0.2152$, $R^2=0.9936$.
Figure 18:
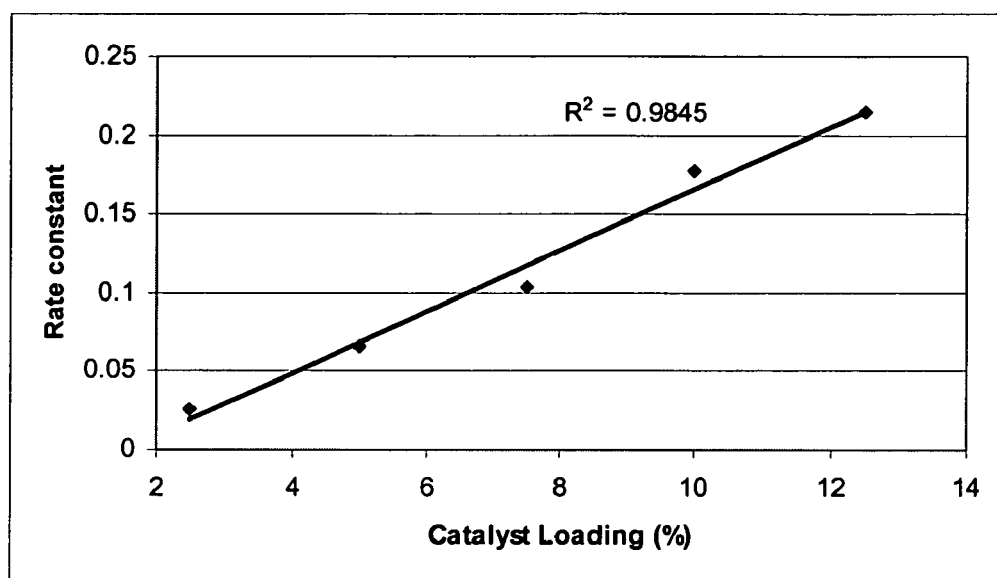
FIG. 18 depicts the kinetic rate constant ($k_{obs}$) at different concentrations of Q-4c. The graph shows the linear relationship between the kinetic rate constant ($k_{obs}$) and the concentration of the catalyst, indicating the reaction is first order in catalyst Q-4c.

The reaction order in catalyst was established by determining the kinetic rate constants at various catalyst concentrations. A plot of the rate constants k$_{obs}$ vs. the catalyst concentration gave a straight line for Q-4c (R$^2$=0.99, FIG. 15). The reaction displays first-order dependence on catalysts Q-4c.

Example 41

General Procedure for Enantioselective Reaction of Ethyl α-Aryl-α-Cynoacetate and Dialkyl Azodicarboxylate Reaction Catalyzed by QD-4b: To a stirred solution of ethyl α-Aryl-α-Cynoacetate (0.22 mmol, 1.1 eq.) and QD-4b (4 mg or 8 mg, 5 mol % or 10 mol %) in Toluene (2 mL) at −78° C., a solution of di-tert-butyl azodicarboxylate or dibenzyl azodicarboxylate in toluene (0.4 mL, 0.5 M, 0.2 mmol, 1.0 eq.) was added dropwise within 10 min. The solution was stirred until the color of the solution turned from yellow to colorless (1-10 h). The solution was allowed to warm to room temperature and purified by a flash chromatography to afford pure product.

Reaction catalyzed by Q-4b: A suspension of Q-4b (4 mg or 8 mg, 5 mol % or 10 mol %) in Toluene (2 mL) was ultrasonically treated until no chunky solid existed (c.a. 15 min), and heated to 120° C. until a clear solution was formed (10-15 min). When it was still hot, the solution was allowed to pass a cotton plug to remove any trace insoluble residue and cooled to room temperature. Then ethyl α-Aryl-α-Cynoacetate (0.22 mmol, 1.1 eq.) was added. This mixture was stirred and cooled to −78° C. A solution of di-tert-butyl azodicarboxylate or dibenzyl azodicarboxylate in toluene (0.4 mL, 0.5 M, 0.2 mmol, 1.0 eq) was added dropwise within 10 min and stirring was continued until the color of the solution turned from yellow to colorless (2-12 h). The solution was allowed to warm to room temperature and purified by a flash chromatography to afford pure product.

Example 42

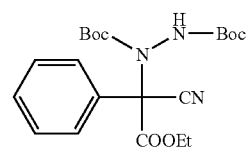

Figure 19:
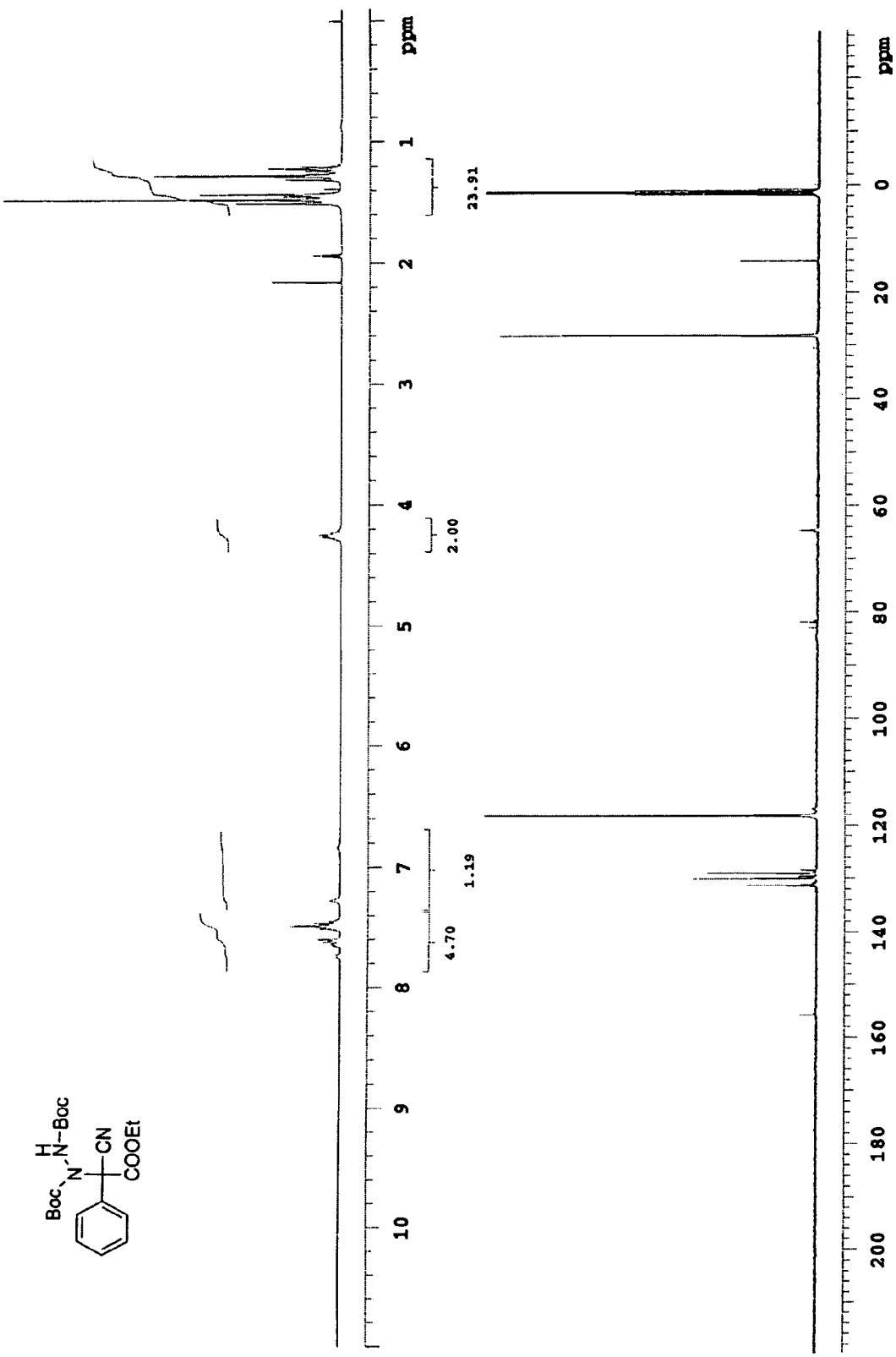
FIG. 19 depicts the $^1$H NMR and $^{13}$C NMR spectra for azodicarboxylate addition product 6s.

6s (+)-. This reaction was catalyzed by Q-4b and obtained as a white foam in 92% yield and 97% ee as determined by HPLC analysis [Chiralpak AD, Hexanes:IPA, 85:15, 1.0 mL/min, λ 220 nm, t (minor)=10.7 min, t (major)=32.3 min]. [α]$_D^{23}$=+64.0 (c 0.175, CHCl$_3$); $^1$H NMR (400 MHz, CD$_3$CN) see FIG. 19; $^{13}$C NMR (100 MHz, CD$_3$CN) see FIG. 19; IR (CHCl$_3$) ν 3347, 2980, 1744, 1718, 1453, 1368, 1242, 1154, 1052 cm$^{-1}$; HRMS (CI) m/z calcd. for (+H$^+$): found.

(−)-. This reaction was catalyzed by QD-4b and obtained as a white foam in 92% yield and 95% ee.

Example 43

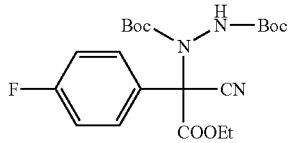

Figure 20:
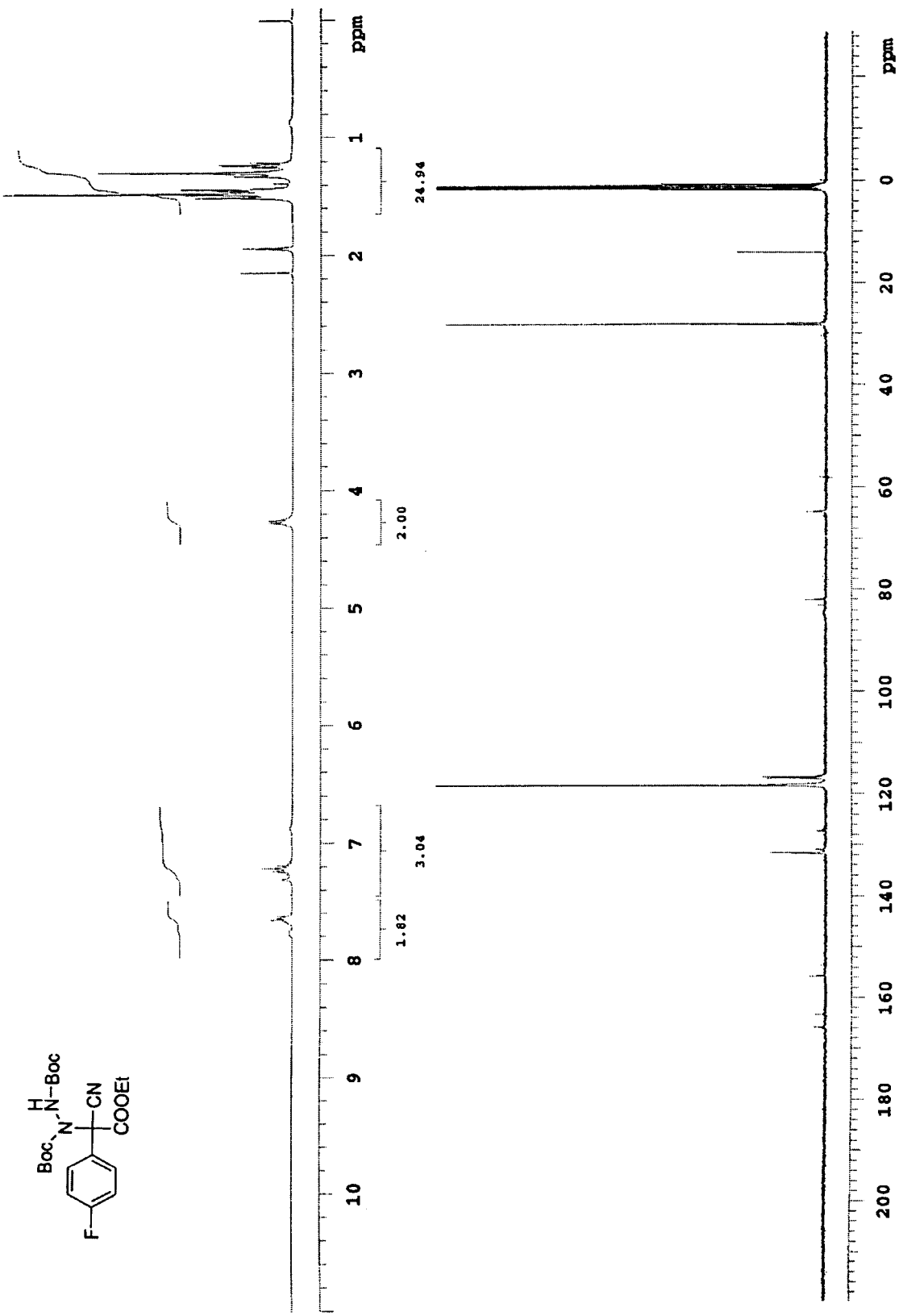
FIG. 20 depicts the $^1$H NMR and $^{13}$C NMR spectra for azodicarboxylate addition product 6t.

(+)-. This reaction was catalyzed by Q-4b and obtained as a white foam in 95% yield and 96% ee as determined by HPLC analysis [Chiralpak AD, Hexanes:IPA, 85:15, 1.0 mL/min, λ 220 nm, t (minor)=10.9 min, t (major)=34.4 min]. $[\alpha]_D^{23}$=+59.7 (c 1.14, CHCl$_3$); $^1$H NMR (400 MHz, CD$_3$CN) see FIG. 20; $^{13}$C NMR (100 MHz, CD$_3$CN) see FIG. 20; IR (CHCl$_3$) ν 3348, 2980, 2929, 1745, 1719, 1607, 1510, 1476, 1369, 1241, 1157, 1054, 1016 cm$^{-1}$; HRMS (CI) m/z calcd. for (+H$^+$): , found.

(−)-. This reaction was catalyzed by QD-4b and obtained as a white foam in 97% yield and 94% ee.

Example 44

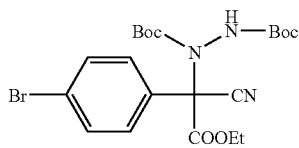

Figure 21:
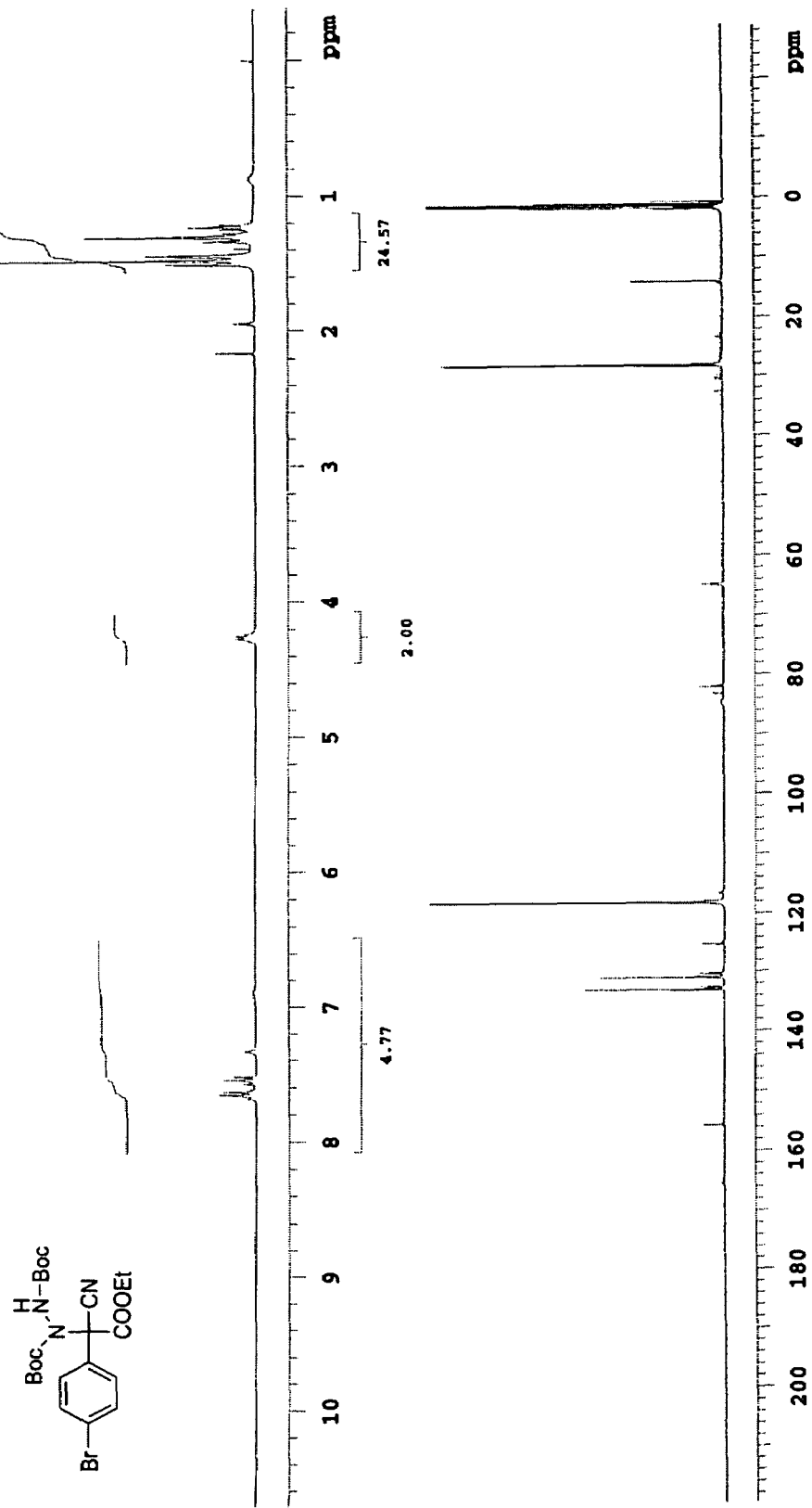
FIG. 21 depicts the $^1$H NMR and $^{13}$C NMR spectra for azodicarboxylate addition product 6u.

(+)-. This reaction was catalyzed by Q-4b and obtained as a white foam in 97% yield and 96% ee as determined by HPLC analysis [Chiralpak AD, Hexanes:IPA, 85:15, 1.0 mL/min, λ 220 nm, t (minor)=12.4 min, t (major)=35.3 min]. $[\alpha]_D^{23}$=+54.4 (c 0.54, CHCl$_3$); $^1$H NMR (400 MHz, CD$_3$CN) see FIG. 21; $^{13}$C NMR (100 MHz, CD$_3$CN) see FIG. 21; IR (CHCl$_3$) ν 3422, 2980, 2932, 1745, 1718, 1644, 1488, 1369, 1243, 1154, 1012 cm$^{-1}$; HRMS (CI) m/z calcd. for (+H$^+$): found.

(−)-. This reaction was catalyzed by QD-4b and obtained as a white foam in 99% yield and 93% ee.

Example 45

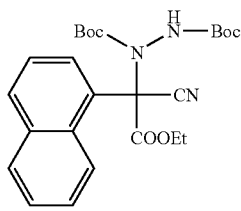

Figure 22:
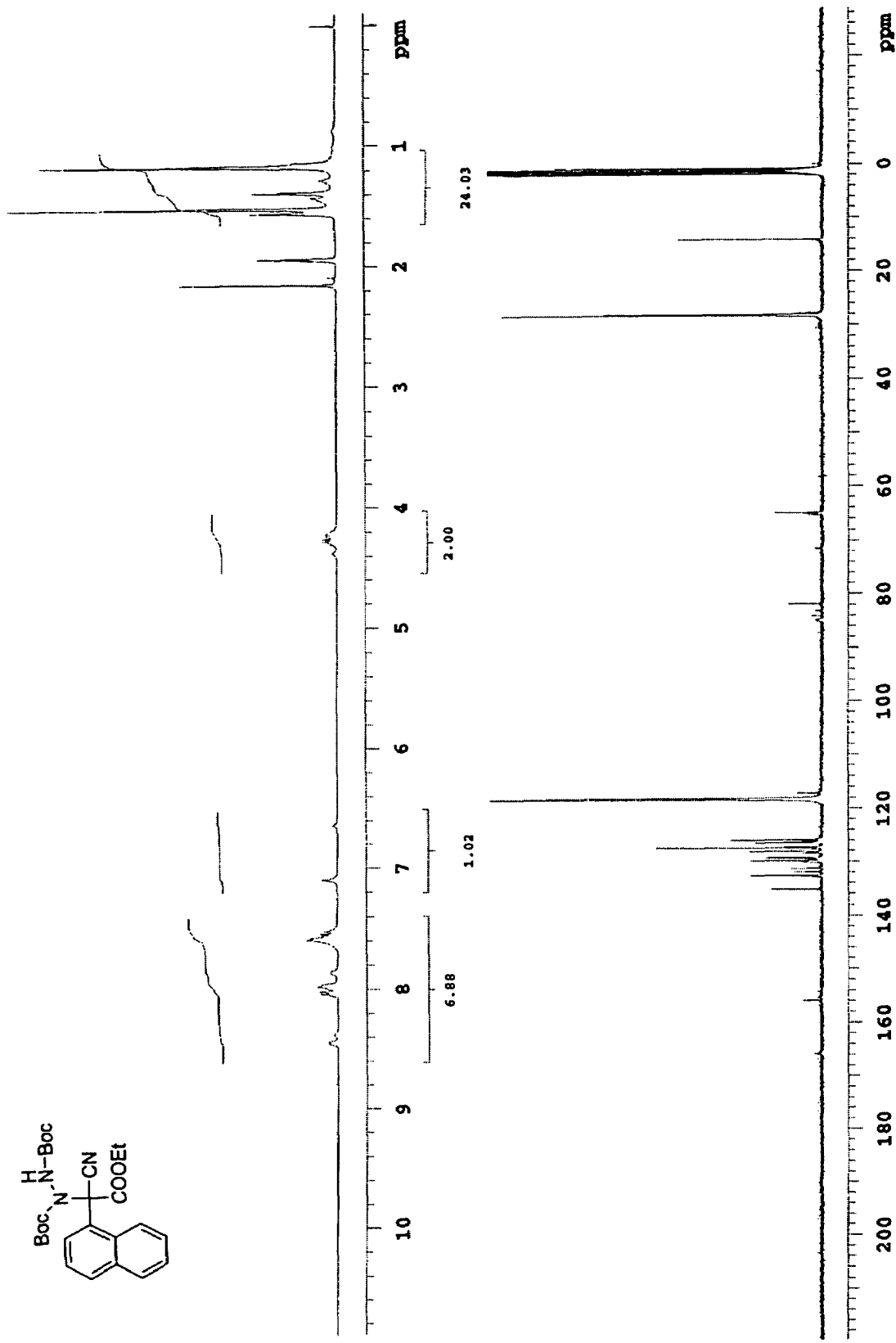
FIG. 22 depicts the $^1$H NMR and $^{13}$C NMR spectra for azodicarboxylate addition product 6v.

(+)-. This reaction was catalyzed by Q-4b and obtained as a white foam in 98% yield and 99% ee as determined by HPLC analysis [Chiralpak AD, Hexanes:IPA, 60:40, 1.0 mL/min, λ 220 nm, t (minor)=9.6 min, t (major)=39.6 min]. $[\alpha]_D^{23}$=+63.9 (c 0.49, CHCl$_3$); $^1$H NMR (400 MHz, CD$_3$CN) see FIG. 22; $^{13}$C NMR (100 MHz, CD$_3$CN) see FIG. 22; IR (CHCl$_3$) ν 3440, 2981, 1721, 1645, 1476, 1369, 1244, 1152, 1015 cm$^{-1}$; HRMS (CI) m/z calcd. for (+H$^+$): found.

(−)-. (This reaction was catalyzed by QD-4b and obtained as a white foam in 99% yield and 96% ee.

Example 46

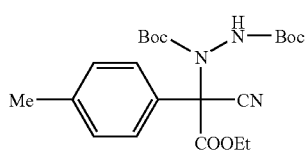

Figure 23:
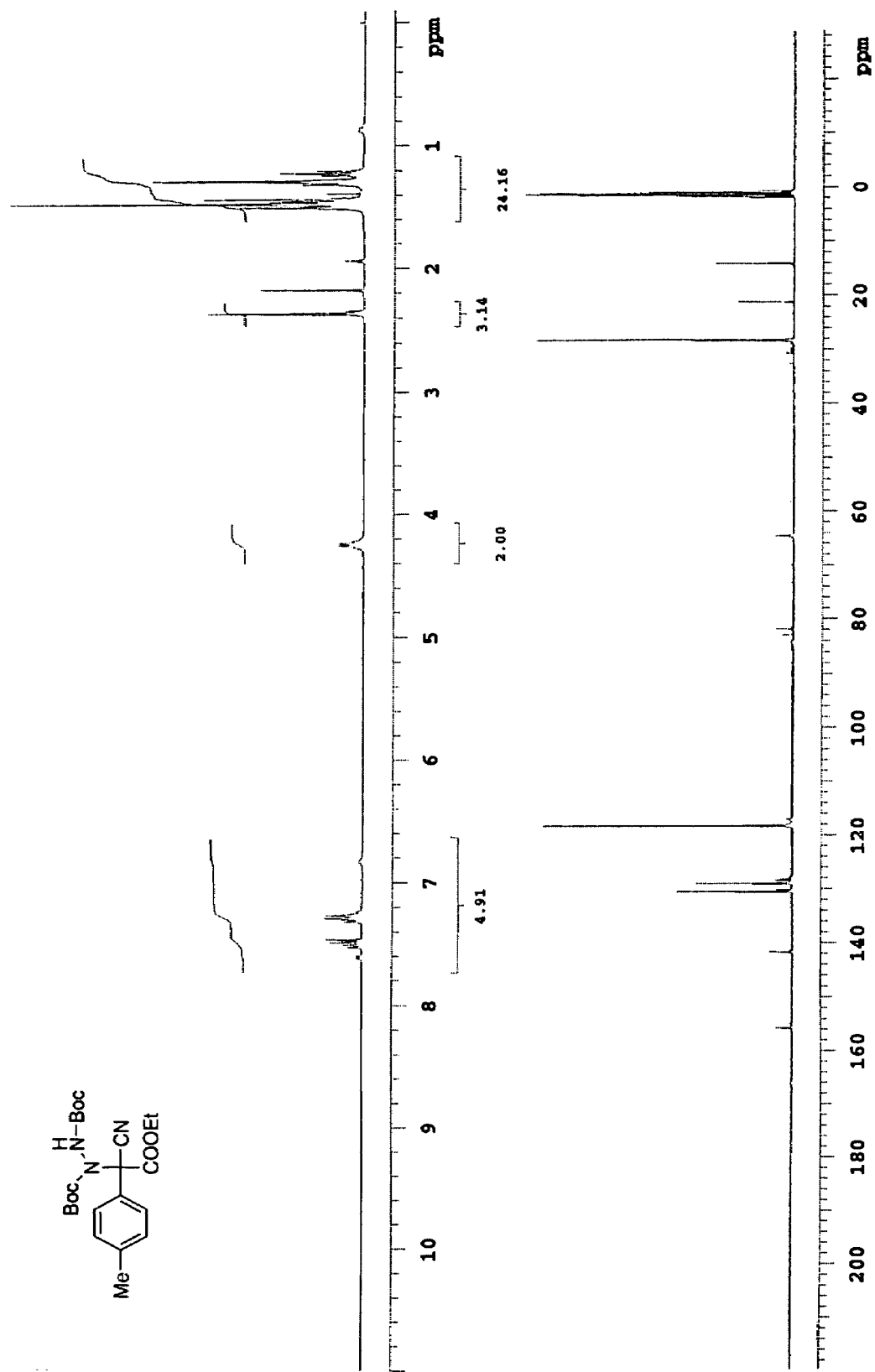
FIG. 23 depicts the $^1$H NMR and $^{13}$C NMR spectra for azodicarboxylate addition product 6w.

(+)-. This reaction was catalyzed by Q-4b and obtained as a white foam in 96% yield and 96% ee as determined by HPLC analysis [Chiralpak AD, Hexanes:IPA, 85:15, 1.0 mL/min, λ 220 nm, t (minor)=11.5 min, t (major)=31.6 min]. $[\alpha]_D^{23}$=+70.8 (c 0.665, CHCl$_3$); $^1$H NMR (400 MHz, CD$_3$CN) see FIG. 23; $^{13}$C NMR (100 MHz, CD$_3$CN) see FIG. 23; IR (CHCl$_3$) ν 3428, 2980, 2933, 1745, 1719, 1649, 1511, 1476, 1458, 1369, 1242, 1155, 1055, 1018 cm$^{-1}$; HRMS (CI) m/z calcd. for (+H$^+$): found.

(−)-. This reaction was catalyzed by QD-4b and obtained as a white foam in 96% yield and 94% ee.

Example 47

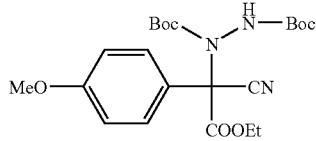

Figure 24:
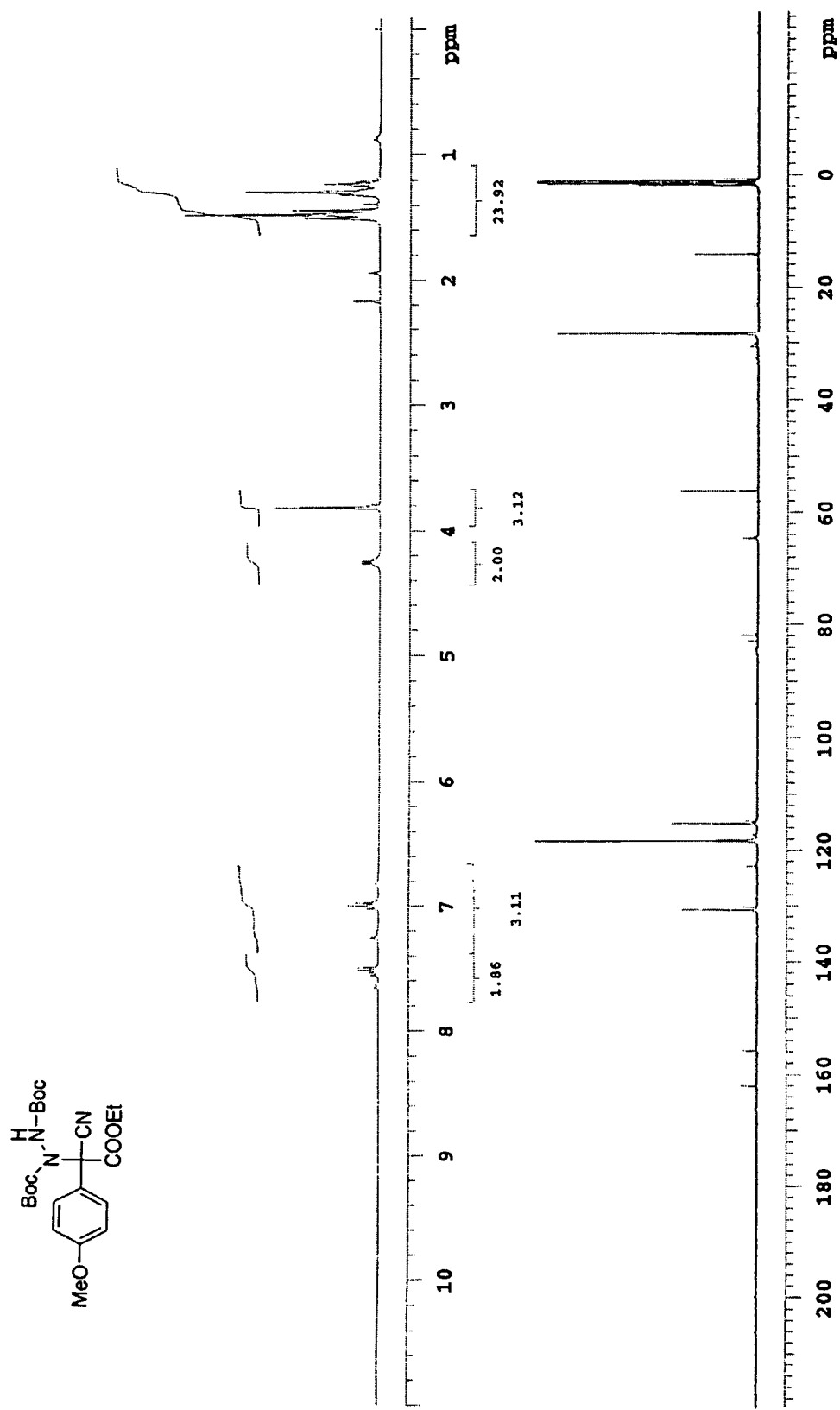
FIG. 24 depicts the $^1$H NMR and $^{13}$C NMR spectra for azodicarboxylate addition product 6x.

(+)-. This reaction was catalyzed by Q-4b and obtained as a white foam in 96% yield and 97% ee as determined by HPLC analysis [Chiralpak OD, Hexanes:IPA, 97:3, 1.0 mL/min, λ 220 nm, t (minor)=10.3 min, t (major)=12.7 min]. $[\alpha]_D^{23}$=+70.0 (c 0.67, CHCl$_3$); $^1$H NMR (400 MHz, CD$_3$CN) see FIG. 24; $^{13}$C NMR (100 MHz, CD$_3$CN) see FIG. 24; IR (CHCl$_3$) ν 3355, 2980, 2935, 1744, 1718, 1610, 1512, 1460, 1369, 1245, 1155, 1055, 1031 cm$^{-1}$; HRMS (CI) m/z calcd. for (+H$^+$): found.

(−)-. This reaction was catalyzed by QD-4b and obtained as a white foam in 96% yield and 94% ee.

Example 48

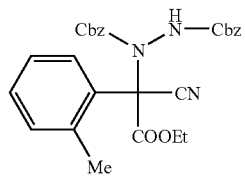

Figure 25:
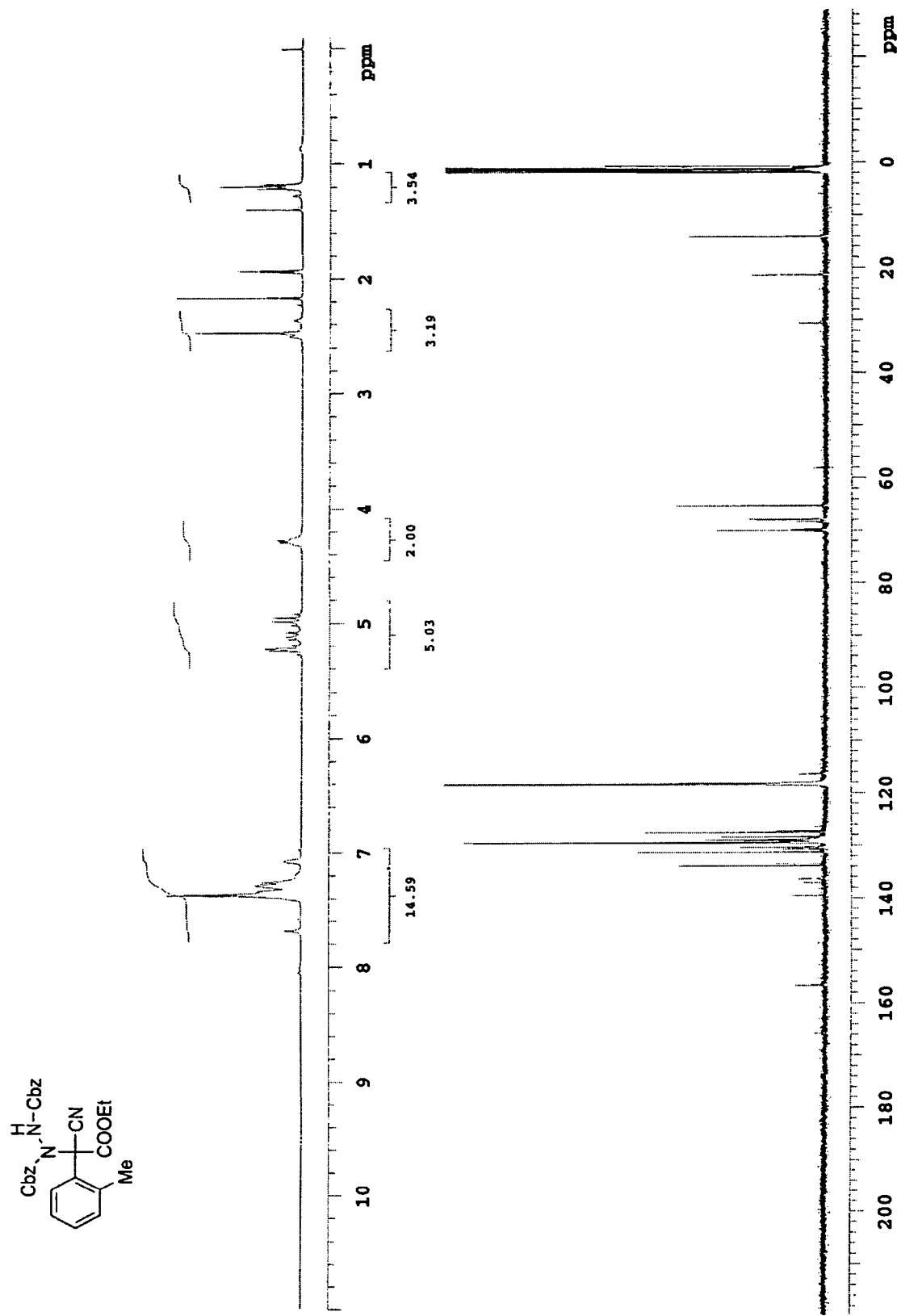
FIG. 25 depicts the $^1$H NMR and $^{13}$C NMR spectra for azodicarboxylate addition product 6y.

(+)-. This reaction was catalyzed by Q-4b and obtained as a white foam in 72% yield and 87% ee as determined by HPLC analysis [Chiralpak OD, Hexanes:IPA, 90:10, 1.0 mL/min, λ 220 nm, t (minor)=10.7 min, t (major)=32.3 min]. $[\alpha]_D^{23}$=+18.9 (c 2.73, CHCl$_3$); $^1$H NMR (400 MHz, CD$_3$CN) see FIG. 25; $^{13}$C NMR (100 MHz, CD$_3$CN) see FIG. 25; IR (CHCl$_3$) ν 3318, 2924, 1732, 1495, 1455, 1391, 1333, 1227, 1092, 1023 cm$^{-1}$; HRMS (CI) m/z calcd. for (+H$^+$): found.

(−)-. This reaction was catalyzed by QD-4b and obtained as a white foam in 71% yield and 82% ee.

Example 49

General Procedure for Enantioselective Michael Addition of Ethyl 2-cyano-2-aryl or 2-alkyl Acetate 12 to Alkenyl Sulfones 13

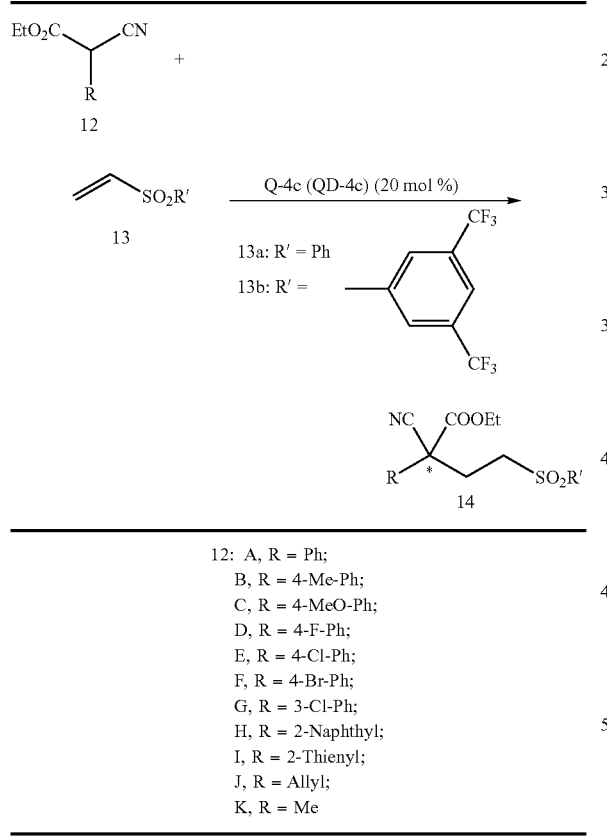

12: A, R = Ph;
B, R = 4-Me-Ph;
C, R = 4-MeO-Ph;
D, R = 4-F-Ph;
E, R = 4-Cl-Ph;
F, R = 4-Br-Ph;
G, R = 3-Cl-Ph;
H, R = 2-Naphthyl;
I, R = 2-Thienyl;
J, R = Allyl;
K, R = Me At −25° C. or 0° C., to a solution of ethyl 2-cyano-2-aryl or 2-alkylacetate 12 (for 12A, 12B, 12C, using 0.6 mmol, for 12D-12I, using 0.5 mmol, for 12J, 12K, using 0.2 mmol) in toluene (0.4 mL) was added the chiral catalyst (20 mol %.) and vinyl phenyl sulfone 3 (0.2 mmol). The resulting mixture was kept at the indicated temperature until sulfone is completely consumed. The reaction mixture was directly subjected to silica gel flash chromatography using the eluent specified below to afford the 1,4-adduct in the yields and enantiomeric excess summarized above. Finally, the column was washed with MeOH and the catalyst was recovered in greater than 95% yield. The recovered catalyst was shown to be identical to that before the reaction by NMR analysis.

Example 50

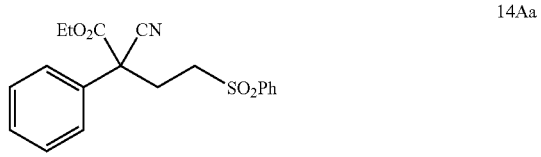

14Aa (+)-14Aa This product was obtained as a colorless oil in 89% yield after flash chromatography (elution gradient:ethyl acetate/hexane=1/8 to 6/1) and 95% ee as determined by HPLC analysis [Daicel chiralcel OD, hexanes:IPA, 90:10, 1.0 ml/min, λ 220 nm, t (major)=16.48 min, t (minor)=14.93 min] from a reaction catalyzed by Q-4c (20 mol %) at −25° C. for 72 hours. $[\alpha]_D^{25}$=+31.6 (c 1.0, CHCl$_3$); $^1$H NMR (400 MHz, CDCl$_3$) δ 7.89 (d, J=8.0 Hz, 2H), 7.69 (t, J=7.2 Hz, 1H), 7.59 (t, J=8.0 Hz, 2H), 7.45-7.39 (m, 5H), 4.28-4.15 (m, 2H), 3.27 (dt, J=4.4 Hz, 12.8 Hz, 1H), 3.04 (dt, J=4.4 Hz, 12.8 Hz, 1H), 2.75-2.59 (m, 2H), 1.21 (t, J=7.2 Hz, 3H); $^{13}$C NMR (100 MHz, CDCl$_3$) δ 166.2, 138.3, 134.1, 132.6, 129.54, 129.48, 128.0, 125.8, 117.0, 63.7, 52.3, 52.1, 30.8, 13.7; HRMS (CI) m/z calcd. for (C$_{19}$H$_{19}$NO$_4$S+H$^+$): 358.1113, found: 358.1108; IR (CHCl$_3$) ν 3064, 2984, 2939, 1745, 1448, 1321, 1237, 1087 cm$^{-1}$.

(−)-14Ab This product was obtained as a colorless oil in 80% yield and 91% ee from a reaction catalyzed by QD-4c (20 mol %) at −25° C. for 72 hours.

Example 51

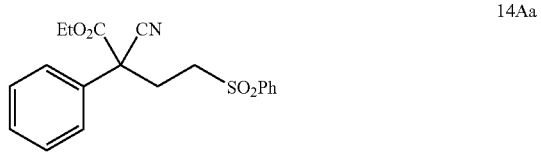

14Aa (+)-14Ba This product was obtained as a colorless oil in 96% yield after flash chromatography (ethyl acetate/hexane=1/7) and 93% ee as determined by HPLC analysis [Daicel Chiralpak AD, hexanes:IPA, 85:15, 1.0 ml/min, λ 220 nm, t(major)=13.33 min, t(minor)=22.06 min] from a reaction catalyzed by Q-4c (20 mol %) at 0° C. for 48 hours. $[\alpha]_D^{25}$=+31.4 (c 1.02, CHCl$_3$); $^1$H NMR (400 MHz, CDCl$_3$) δ 7.89 (d, J=8.0 Hz, 2H), 7.69 (t, J=7.2 Hz, 1H), 7.58 (t, J=8.0 Hz, 2H), 7.30 (d, J=8.4 Hz, 2H), 7.20 (d, J=8.4 Hz, 2H), 4.27-4.11 (m, 2H), 3.25 (dt, J=5.6 Hz, 12.8 Hz, 1H), 3.03 (dt, J=4.4 Hz, 12.8 Hz, 1H), 2.72-2.58 (m, 2H), 2.35 (s, 3H), 1.21 (t, J=7.2 Hz, 3H); $^{13}$C NMR (100 MHz, CDCl$_3$) δ166.3, 139.5, 138.3, 134.0, 130.1, 129.5, 129.4, 127.9, 125.6, 117.2, 63.6, 52.06, 51.98, 30.7, 20.9, 13.6; HRMS (CI) m/z calcd. for (C$_{20}$H$_{21}$NO$_4$S+H$^+$): 372.1270, found: 372.1276; IR (CHCl$_3$) ν 2983, 1744, 1447, 1321, 1235, 1148, 1087 cm$^-$.

Example 52

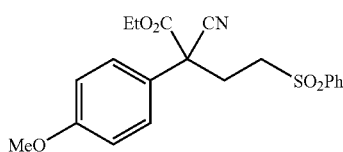

14Ca (+)-14Ca This product was obtained as a colorless oil in 92% yield after flash chromatography (ethyl acetate/hexane=1/6) and 93% ee as determined by HPLC analysis [Daicel Chiralpak AD, hexanes:IPA, 85:15, 0.9 ml/min, λ 220 nm, t(major)=28.93 min, t(minor)=33.20 min] from a reaction catalyzed by Q-4c (20 mol %) at 0° C. for 70 hours. $[\alpha]_D^{25}$=+31.0 (c 1.10, CHCl$_3$); $^1$H NMR (400 MHz, CDCl$_3$) δ 7.89 (d, J=7.2 Hz, 2H), 7.69 (t, J=7.2 Hz, 1H), 7.58 (t, 7.2 Hz, 2H), 7.34 (td, J=2.4 Hz, 9.2 Hz, 2H), 6.90 (td, J=2.4 Hz, 9.2 Hz, 2H), 4.27-4.14 (m, 2H), 3.81 (s, 3H), 3.25 (dt, J=5.2 Hz, 12.0 Hz, 1H), 3.04 (dt, J=4.0 Hz, 12.0 Hz, 1H), 2.72-2.57 (m, 2H), 1.21 (t, J=6.8 Hz, 3H); $^{13}$C NMR (100 MHz, CDCl$_3$) δ166.4, 160.2, 138.3, 134.1, 129.4, 128.0, 127.1, 124.2, 117.2, 114.8, 63.6, 55.3, 52.1, 51.6, 30.7, 13.7; HRMS (CD) m/z calcd. for (C$_{20}$H$_{21}$NO$_5$S+H$^+$): 388.1219, found: 388.1210; IR (CHCl$_3$) ν 2982, 1743, 1512, 1307, 1257, 1236, 1147 cm$^{-1}$.

Example 53

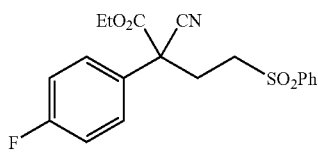

14Da (+)-14Da This product was obtained as a colorless oil in 90% yield after flash chromatography (ethyl acetate/hexane=1/5) and 94% ee as determined by HPLC analysis [Daicel chiralcel OD, hexane:IPA, 90:10, 1.0 mL/min, λ 220 nm, t(major)=21.42 min, t(minor)=17.98 min] from a reaction catalyzed by Q-4c (20 mol %) at -25° C. for 72 hours. $[\alpha]_D^{25}$=+27.2 (c 1.13, CHCl$_3$); $^1$H NMR (400 MHz, CDCl$_3$) δ 7.90-7.88 (m, 2H), 7.70 (tt, J=1.2 Hz, 7.6 Hz, 11H), 7.59 (t, J=7.2 Hz, 2H), 7.45-7.41 (m, 2H), 7.11 (tt, J=1.6 Hz, 8.0 Hz, 2H), 4.29-4.16 (m, 2H), 3.26 (dt, J=4.8 Hz, 13.6 Hz, 1H), 3.03 (dt, J=3.6 Hz, 12.8 Hz, 1H), 2.72 (dt, J=4.4 Hz, 14.0 Hz, 1H), 2.61 (dt, J=4.4 Hz, 14.0 Hz, 1H), 1.22 (t, J=7.2 Hz, 3H); $^{13}$C NMR (100 MHz, CDCl$_3$) δ 166.0, 163.0 (d, $^1J_{C,F}$=249.0 Hz), 138.3, 134.1, 129.5, 128.4 (d, $^4J_{C,F}$=3.0 Hz), 128.0, 127.8 (d, $^3J_{C,F}$=8.3 Hz), 116.9, 116.6(d, 2J CF=22.1 Hz), 63.9, 52.0, 51.7, 30.8, 13.6; HRMS (CI) m/z calcd for (C$_{19}$H$_{18}$FNO$_4$S+H$^+$): 376.1019, found: 376.1015; IR (CHCl$_3$) ν 3070, 2985, 2940, 1745, 1604, 1510, 1447, 1307, 1237, 1087 cm$^{-1}$.

Example 54

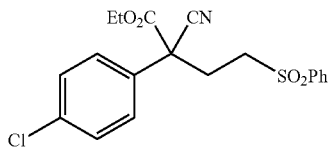

14Ea (+)-14Ea This product was obtained as a colorless oil in 95% yield after flash chromatograph (ethyl acetate/hexane=1/6) and 94% ee as determined by HPLC analysis [Daicel chiralcel OD, Hexane:IPA, 85:15, 1.0 mL/min, λ 220 nm, t(major)=16.75 min, t(minor)=13.57 min] from a reaction catalyzed by Q-4c (20 mol %) at -25° C. for 69 hours. $[\alpha]_D^{25}$=+31.9 (c 1.10, CHCl$_3$); $^1$H NMR (400 MHz, CDCl$_3$) δ 7.85 (d, J=8.8 Hz, 2H), 7.65 (t, J=7.2 Hz, 1H), 7.55 (t, J=6.4 Hz, 2H), 7.34 (s, 4H), 4.22-4.14 (m, 2H), 3.23 (dt, J=4.4 Hz, 12.8 Hz, 1H), 2.99 (dt, J=4.4 Hz, 12.8 Hz, 1H), 2.69 (dt, J=4.4 Hz, 12.8 Hz, 1H), 2.56 (dt, J=4.4 Hz, 12.8 Hz, 1H), 1.17 (t, J=7.2 Hz, 3H); $^{13}$C NMR (100 MHz, CDCl$_3$) δ 165.8, 138.2, 135.6, 134.1, 131.1, 129.6, 129.4, 127.9, 127.2, 116.6, 63.9, 51.9, 51.8, 30.6, 13.6; HRMS (CI) m/z calcd for (C$_{19}$H$_{18}$ClNO$_4$S+H$^+$): 392.0723, found: 392.0728; IR (CHCl$_3$) ν 3066, 2984, 1745, 1493, 1447, 1322, 1236, 1148 cm$^{-1}$.

(-)-14Ea This product was obtained as a colorless oil in 94% yield and 89% ee from a reaction catalyzed by QD-4c (20 mol %) at -25° C. for 72 hours.

Example 55

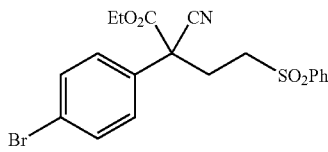

14Fa (+)-14Fa This product was obtained as a colorless oil in 95% yield after flash chromatography (ethyl acetate/hexane=1/6) and 94% ee as determined by HPLC analysis [Daicel chiralpak AD, Hexane:IPA, 85:15, 1.0 mL/min, λ 220 nm, t(major)=22.51 min, t(minor)=26.82 min] from a reaction catalyzed by Q-4c (20 mol %) at -25° C. for 66 hours. $[\alpha]_D^{25}$=+28.8 (c 1.10, CHCl$_3$); $^1$H NMR (400 MHz, CDCl$_3$) δ 7.89 (d, J=8.0 Hz, 2H), 7.70 (t, J=8.0 Hz, 1H), 7.60 (t, J=8.0 Hz, 2H), 7.54 (d, J=8.8 Hz, 2H), 7.32 (d, J=8.8 Hz, 2H), 4.29-4.16 (m, 2H), 3.25 (dt, J=4.4 Hz, 13.2 Hz, 1H), 3.01 (dt, J=4.0 Hz, 13.2 Hz, 1H), 2.71 (dt, J=4.4 Hz, 13.2 Hz, 1H), 2.60 (dt, J=4.0 Hz, 13.2 Hz, 1H), 1.23 (t, J=7.2 Hz, 3H); $^{13}$C NMR (100 MHz, CDCl$_3$) δ165.8, 138.2, 134.2, 132.7, 131.6, 129.5, 128.0, 127.5, 123.9, 116.6, 64.0, 52.01, 51.96, 30.7, 13.7; HRMS (CI) m/z calcd for (C$_{19}$H$_{18}$BrNO$_4$S+H$^+$): 436.0218, found: 436.0208; IR (CHCl$_3$) ν 2983, 1745, 1489, 1447, 1322, 1236, 1148 cm$^{-1}$.

(-)-14Fa This product was obtained as a colorless oil in 95% yield and 88% ee from a reaction catalyzed by QD-4c (20 mol %) at -250C for 72 hours.

Example 55

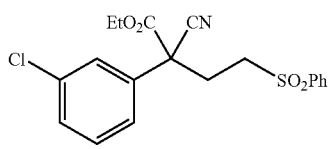

14Ga (+)-14Ga This product was obtained as a colorless oil in 96% yield after flash chromatography (ethyl acetate/hexane=1/7) and 93% ee as determined by HPLC analysis [Daicel chiralpak AD, Hexane:IPA, 85:15, 1.0 mL/min, λ 220 nm, t (major)=15.00 min, t (minor)=12.58 min] from a reaction catalyzed by Q-4c (20 mol %) at −25° C. for 60 hours. $[\alpha]_D^{25}$=+29.5 (c 1.00, CHCl$_3$); $^1$H NMR (400 MHz, CDCl$_3$) δ 7.91-7.88 (m, 2H), 7.73-7.68 (m, 1H), 7.60 (t, J=7.2 Hz, 2H), 7.42-7.33 (m, 4H), 4.31-4.17 (m, 2H), 3.27 (dt, J=4.4 Hz, 13.6 Hz, 1H), 3.04 (dt, J=3.6 Hz, 12.8 Hz, 1H), 2.73 (dt, J=4.8 Hz, 12.8 Hz, 1H), 2.58 (dt, J=4.4 Hz, 12.8 Hz, 1H), 1.23 (t, J=6.8 Hz, 3H); $^{13}$C NMR (100 MHz, CDCl$_3$) δ 165.7, 138.2, 135.6, 134.5, 134.2, 130.8, 129.8, 129.5, 128.0, 126.1, 124.0, 116.5, 64.1, 52.0, 30.9, 13.7; HRMS (CI) m/z calcd for ($C_{19}H_{18}ClNO_4S+H^+$): 392.0723, found: 392.0721; IR (CHCl$_3$) ν 2984, 1746, 1478, 1447, 1309, 1322, 1237, 1148 cm$^{-1}$.

Example 56

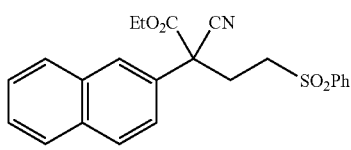

14Ha (+)-14Ha This product was obtained as a colorless oil in 96% yield after flash chromatography (elution gradient: Ethyl Acetate/Hexane=1/6) and 98% ee as determined by HPLC analysis [Daicel chiralcel OD, Hexane:IPA, 90:10, 1.0 mL/min, λ 220 nm, t(major)=23.90 min, t(minor)=27.21 min] from a reaction catalyzed by Q-4c (20 mol %) at −25° C. for 60 hours. $[\alpha]_D^{25}$=+46.7 (c 1.00, CHCl$_3$); $^1$H NM (400 MHz, CDCl$_3$) δ 7.97 (d, J=1.6 Hz, 1H), 7.88-7.84 (m, 5H), 7.68-7.64 (m, 1H), 7.57 (m, 4H), 7.44 (dd, J=2.4 Hz, 8.4 Hz, 1H), 4.29-4.15 (m, 2H), 3.32 (dt, J=4.8 Hz, 13.6 Hz, 1H), 3.04 (dt, J=4.4 Hz, 12.4 Hz, 1H), 2.87-2.71 (m, 2H), 1.20 (t, J=7.6 Hz, 3H); $^{13}$C NMR (100 MHz, CDCl$_3$) δ 166.2, 138.3, 134.0, 133.1, 132.9, 129.7, 129.6, 129.4, 128.2, 127.9, 127.6, 127.4, 127.2, 125.9, 122.0, 117.1, 63.8, 52.5, 52.1, 30.6, 13.6; HRMS (CI) m/z calcd for ($C_{23}H_{21}NO_4S+H^+$): 408.1270, found: 408.1266; IR (CHCl$_3$) ν 3061, 2983, 1744, 1321, 1234, 1151, 1087 cm$^{-1}$.

(−)-14Ha This product was obtained as a colorless oil in 95% yield and 90% ee from a reaction catalyzed by QD-4c (20 mol %) at −25° C. for 60 hours.

Example 57

14-Ia (+)-14Ia This product was obtained as a brown oil in 95% yield after flash chromatography (ethyl acetate/hexane=1/6) and 93% ee as determined by HPLC analysis [Daicel chiralcel OD, hexane:IPA, 90:10, 1.0 mL/min, λ 220 nm, t (major)=20.54 min, t (minor)=18.50 min] from a reaction catalyzed by Q-4c (20 mol %) at −25° C. for 48 hours. $[\alpha]_D^{25}$=+20.2 (c 1.00, CHCl$_3$); $^1$H NMR (400 MHz, CDCl$_3$) δ 7.91-7.88 (m, 2H), 7.72-7.68 (m, 1H), 7.59 (t, J=8.0 Hz, 2H), 7.36 (dd, J=1.2 Hz, 4.8 Hz, 2H), 7.20 (dd, J=1.2 Hz, 4.0 Hz, 1H), 6.99 (dd, J=3.6 Hz, 4.8 Hz, 1H), 4.29-4.23 (m, 2H), 3.27 (dt, J=4.8 Hz, 12.8 Hz, 1H), 3.14 (dt, J=4.4 Hz, 12.4 Hz, 1H), 2.78-2.61 (m, 2H), 1.27 (t, J=7.6 Hz, 3H); $^{13}$C NMR (100 MHz, CDCl$_3$) δ 165.5, 138.2, 134.9, 134.1, 129.4, 127.9, 127.5, 127.4, 127.1, 116.3, 64.0, 52.0, 49.3, 32.1, 13.6; HRMS (CI) m/z calcd for ($C_{17}H_{17}NO_4S_2+H^+$): 364.0677, found: 364.0669; IR (CHCl$_3$) ν cm$^{-1}$;

(−)-14Ia This product was obtained as a brown oil in 91% yield and 88% ee from a reaction catalyzed by QD-4c (20 mol %) at −25° C. for 48 hours.

Example 58

(+)-14Jb (+)-14Jb This product was obtained as a white solid in 76% yield after flash chromatography (ethyl acetate:hexane=1:10) and in 93% ee as determined by HPLC analysis [Daicel Chiralcel OD, hexane:IPA, 90:10, 1.0 ml/min, λ=220 nm, t(major)=9.78 min, t(minor)=13.73 min] from the reaction catalyzed by Q-4c (20 mol %) at 0° C. for 96 hours. $[\alpha]_D^{25}$=+1.6 (c 1.5, CHCl$_3$); $^1$H NMR (400 MHz, CDCl3) δ 8.36 (s, 2H), 8.18 (s, 1H), 5.66-5.78 (m, 2H) 5.20-5.30 (m, 1H), 4.18-4.32 (m, 2H), 3.36 (dt, J=12.8 Hz, J=4.4 Hz, 1H), 3.32 (dt, J=12.8 Hz, J=4.4 Hz, 1H), 2.68 (dd, J=13.6 Hz, J=6.8 Hz, 1H), 2.65 (dd, J=13.6 Hz, J=6.8 Hz, 1H), 2.40 (dt, J=12.4 Hz, J=4.4 Hz, 1H), 2.24 (dt, J=12.4 Hz, J=4.4 Hz, 1H), 1.29 (t, J=6.8 Hz, 3H); $^{13}$C NMR (100 MHz, CDCl3) δ 166.8, 141.4, 133.5 (q, J=34 Hz) 129.2, 128.5, 127.9, 122.3 (q, J=273.0 Hz), 122.2, 117.2, 63.6, 52.3, 47.4, 41.3, 28.0, 13.9; IR (CHCl3) ν 3088, 2987, 1739, 1360, 1279, 1185, 1147 cm$^{-1}$; HRMS (CI) m/z calcd for ($C_{18}H_{17}F_6NO_4S+H^+$): 458.0861, found 458.0862.

Example 59

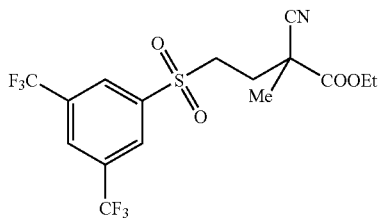

(-)-14Kb (−)-14Kb This product was obtained as a white solid in 85% yield after flash chromatography (ethyl ether:hexane=1:5) and in 92% ee as determined by HPLC analysis [Daicel Chiralcel OD, hexane: IPA, 90:10, 1.0 ml/min, λ=220 nm, t(major)=10.88 min, t(minor)=17.64 min] from the reaction catalyzed by Q-4c (20 mol %) at 0° C. for 96 hours. $[\alpha]_D^{25}=-1.0$ (c 2.0, CHCl$_3$); $^1$H NMR (400 MHz, CDCl3) δ 8.40 (s, 2H), 8.21 (s, 1H), 4.28 (dq, J=1.6 Hz, J=7.2 Hz, 2H), 3.38 (dt, J=13.6 Hz, J=4.4 Hz, 1H), 3.31(dt, J=12.8 Hz, J=4.4 Hz, 1H), 2.45 (dt, J=12.8 Hz, J=4.4 Hz, 1H), 2.27 (dt, J=12.8 Hz, J=4.4 Hz, 1H), 1.67 (s, 3H), 1.32 (t, J=6.8 Hz, 3H); $^{13}$C NMR (100 MHz, CDCl3) δ 167.6, 141.4, 133.5 (q, J=30 Hz) 128.5, 128.0, 127.9, 122.1 (q, J=272.4 Hz), 118.2, 63.1, 52.4, 42.4, 29.8, 23.7, 13.9; IR (CHCl$_3$) ν 3088, 2990, 1745, 1281, 1186, 1147 cm−1; HRMS (CI) m/z calcd for (C$_{16}$H$_{15}$F$_6$NO$_4$S+H$^+$): 432.0708, found 432.0712.

(+)-14 Kb This product was obtained as a white solid in 83% yield and 88% ee from a reaction catalyzed by QD-4c (20 mol %) at 0° C. for 96 hours.

Example 60

Synthesis of optically active α, α-disubstituted amino acid 16:

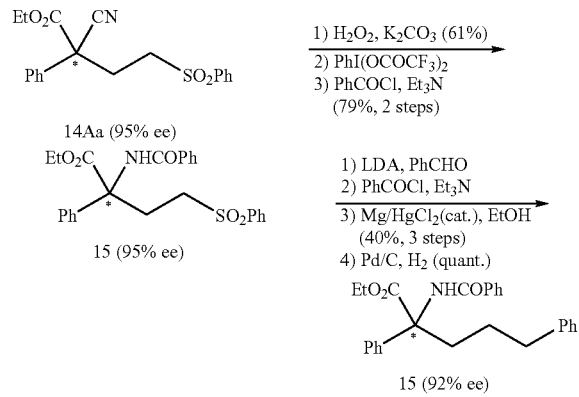

Preparation of amide 17 from adduct 14Aa:

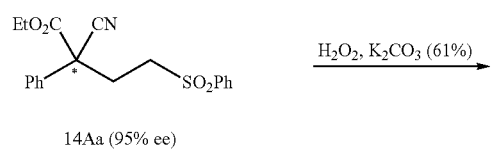

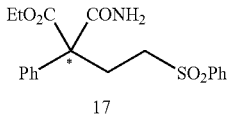

At room temperature, to a solution of 14Aa (357 mg, 1.0 mmol) in DMSO (3.0 ml) was added K$_2$CO$_3$.1.5H$_2$O (70 mg, 0.5 eq.), after which H$_2$O$_2$ (0.15 mL, 30%, 4 eq.) was added. After 1 h another portion of H$_2$O$_2$ was added, then another 3 portions was added Portion/2 h. The mixture was then stirred for another 1 h, after which the reaction mixture was diluted with brine (20 mL), the resulting mixture was subjected to extraction with ethyl acetate (2×30 mL). The combined organic phase was washed with brine (2×20 mL), dried over Na$_2$SO$_4$, concentrated in vacuo, and the residue was subjected to flash chromatography (eluent:hexanes/ EtOAc=4/1 to 1/1) to give amide 17 (240 mg, 62% yield). $^1$H NMR (400 MHz, CDCl$_3$) δ 7.86 (d, J=7.2 Hz, 2H), 7.64(t, J=7.2 Hz, 1H), 7.54 (t, J=7.2 Hz, 2H), 7.34-7.30 (m, 3H), 7.19-7.17 (m, 2H), 6.83 (br, 1H), 6.14 (br, 1H), 4.23 (q, J=7.2 Hz, 2H), 3.28-3.21 (m, 1H), 3.10-3.03 (m, 1H), 2.64-2.56 (m, 2H), 1.24 (t, J=7.2 Hz, 3H); $^{13}$C NMR (100 MHz, CDCl$_3$) δ171.4, 170.8, 138.7, 137.8, 133.6, 129.2, 129.0, 128.2, 128.0, 126.7, 62.5, 62.0, 52.7, 29.2, 13.8; IR (CHCl$_3$) ν 3456 (br), 3342 (br), 3063, 2982, 2934, 1729, 1684, 1585, 1447, 1300, 1237, 1143, 1087, 725 cm$^{-1}$. Katritzky, A. R.; Pilarski, B.; Urogdi, L. Synthesis 1989, 949.

Preparation of Amino-acid 15 from Amide 17

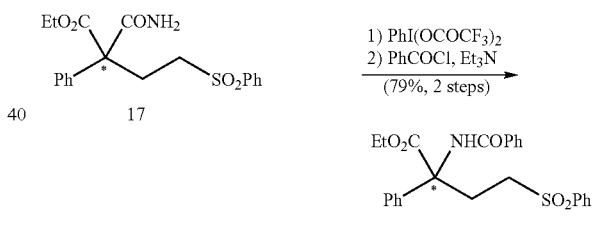

To a solution of 17 (124 mg, 0.33 mmol) in CH$_3$CN (1.6 if L) and H$_2$O (0.8 mL) was added PhI(OCOCF$_3$)$_2$ (214 mg, 1.5 eq.). The resulting mixture was stirred overnight and then was diluted with ether (20 mL) and washed with HCl (2.0 N, 3×4.0 mL), the combined aqueous phase was basified with Na$_2$CO$_3$ (5%, aq.) until the pH=12-13. Then the mixture was extracted with ethyl acetate (2×30 mL), and the combined organic phase was washed with brine (2×20 mL), dried over Na$_2$SO$_4$, concentrated in vacuo. The residue was dissolved in anhydrous CH$_2$Cl$_2$ (2 mL). To the resulting solution was added Et$_3$N (0.14 mL, 3 eq.) and PhCOCl (0.046 mL, 1.2 eq.). The solution was stirred at room temperature overnight. The reaction mixture was diluted with ethyl acetate (60 mL), and washed with Na$_2$CO$_3$ (5% aq., 10 mL), brine (2×20 mL), dried over anhydrous Na$_2$SO$_4$, concentrated in vacuo and the residue was subjected to flash chromatography (eluent:ethyl acetate/hexane=½) to give amino acid 15 (120 mg, 79% yield) in 95% ee as determined by HPLC analysis [Daicel chiralpak AD, Hexane:IPA, 80:20, 1.0 mL/min, λ 220 nm, t (major)=29.3 min, t (minor)=21.2 min]. $\alpha]_D^{25}$=+8.3 (c 1.1, CHCl$_3$); $^1$H NMR (400 MHz, CDCl₃) δ7.87 (d, J=7.2 Hz, 2H), 7.75 (d, J=7.2 Hz, 2H), 7.62 (t, J=7.2 Hz, 1H), 7.57 (br, 1H), 7.53-7.50 (M, 3H), 7.45-7.39 (m, 4H), 7.35-7.26 (m, 3H), 4.21-4.08 (m, 2H), 3.35-3.20 (m, 2H), 3.08-2.93 (m, 2H), 1.15 (t, J=7.2 Hz, 3H); ¹³C NMR (100 MHz, CDCl₃) δ171.6, 165.7, 138.4, 138.0, 133.7, 133.6, 131.9, 129.3, 128.8, 128.6, 128.3, 127.9, 127.0, 125.5, 64.5, 62.8, 52.1, 27.2, 13.7; IR (CHCl₃) ν 3403 (br), 3063, 3027, 2983, 1732, 1667, 1581, 1513, 1480, 1447, 1307, 1245, 1204, 1149, 1086, 752 cm⁻¹. Radhakrishna, A. S.; Parham, M. E.; Riggs, R. M.; Loudon, G. M. *J. Org. Chem.* 1979, 44, 1746.

Preparation of Amino Acid 18 from 15

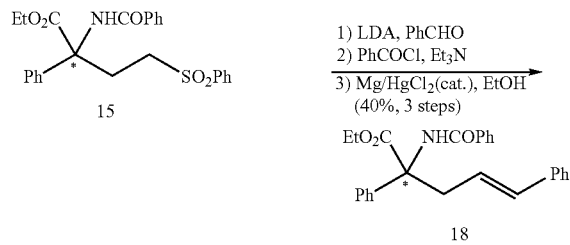

Under argon at −65° C. to a solution of 15 (90 mg, 0.2 mmol) in anhydrous THF (1.5 mL) was added LDA (2.0 M in heptane/tetrahydrofuran/ethylbezene, 0.3 ml, 3 eq.). The resulting mixture was gradually warmed to −40° C. over 30 min, after which PhCHO (0.024 ml, 1.2 eq.) was added in one portion. Then the reaction mixture was gradually warmed to room temperature over 1 h. The reaction was then quenched with NH₄Cl (sat. aq.) and diluted with ethyl acetate (30 mL). The organic phase was washed with brine (2×10 mL), dried over anhydrous Na₂SO₄, and concentrated in vacuo. The residue was dissolved in anhydrous CH₂Cl₂ (1.5 mL). To the resulting solution, Et₃N (0.084 ml, 3 eq.) and PhCOCl (0.028 mL, 1.2 eq.) were added sequentially. The mixture was stirred at room temperature for 3 hours and was then diluted with ethyl acetate (40 mL), washed with Na₂CO₃ (5% aq. 10 mL), brine (2×10 mL), dried over anhydrous Na₂SO₄ and concentrated in vacuo. The residue was dissolved in anhydrous EtOH (2.0 mL). To the resulting solution HgCl₂ (11 mg, 0.2 eq.) and Mg (15 mg, 3 eq.-50 mesh) was added sequentially. The resulting reaction mixture was stirred for 2 hours, then was poured into NH₄Cl (sat. aq. 5 mL). The mixture was subjected to extraction with ethyl acetate (50 mL). The organic phase was washed with brine (2×20 ml), dried over anhydrous Na₂SO₄, and concentrated in vacuo. The residue was subjected to flash chromatography (eluent:ethyl acetate/hexane=1/9) to give olefin 18 (32 mg, 40% yield, E/Z=3/1) Data for E isomer: ¹H NMR (400 MHz, CDCl₃) δ 7.81 (d, J=7.2 Hz, 2H), 7.76 (br, 1H), 7.53 (d, J=7.2 Hz, 2H), 7.50-7.47 (m, 1H), 7.43 (d, J=8.0 Hz, 2H), 7.40 (d, J=6.8 Hz, 1H), 7.36 (d, J=7.6 Hz, 2H), 7.34-7.28 (m, 1H), 7.26-7.24 (m, 3H), 7.23-7.17 (M, 1H), 6.53 (d, J=16.0 Hz, 1H), 6.08 (dt, J=16.0 Hz, 8.0 Hz, 1H), 4.32-4.24 (m, 1H), 4.21-4.10 (m, 1H), 3.97 (dd, J=8.0 Hz, 13.6 Hz, 1H), 3.46 (dd, J=8.0 Hz, 13.6 Hz, 1H), 1.22 (t, J=7.2 Hz, 3H); ¹³C NMR (100 MHz, CDCl₃) δ 172.6, 165.8, 139.2, 137.1, 134.7, 134.6, 131.6, 128.61, 128.57, 128.46, 127.9, 127.4, 1267.0, 126.2, 125.9, 123.7, 66.0, 62.6, 36.3, 14.0; IR (CHCl₃) ν 3413 (br), 3060, 3027, 2981, 2933, 1728, 1673, 1506, 1480, 1447, 1307, 1216 cm⁻¹. (a) Evans, D. A.; Carter, P. H.; Carreira, E. M.; Prunet, J. A.; Charette, A. B.; Lautens, M. *Angew. Chem. Int. Ed.* 1998, 37, 2354; (b) Lee, G. H.; Lee, H. K.; Choi, E. B.; Kim, B. T.; Pak, C. S. *Tetrahedron Lett.* 1995, 36, 5607.

Preparation of Amino Acid 16 from 18

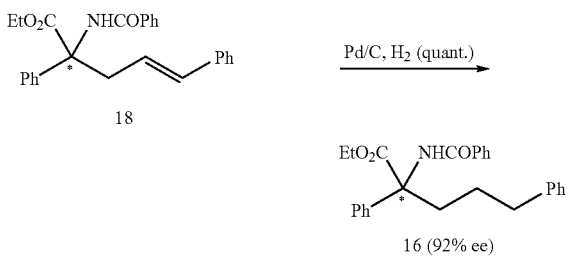

The suspension formed by the addition of Pd/C (10%, 4 mg) to the solution of 18 (13 mg) in ethyl acetate (1.0 mL) was stirred under H₂ (1 atmosphere) for 2 hours. The reaction mixture was passed through a short pad of silica gel to remove Pd/C (using ethyl acetate as eluent), and concentrated in vacuo to give 16 (13 mg, 99% yield) in 92% ee as determined by HPLC analysis [Daicel chiralpak AD, Hexane:IPA, 90:10, 1.0 mL/min, λ 220 nm, t (major)=14.6 min, t (minor)=20.7 min]. α]$_D^{25}$=−3.7 (c 0.3, CHCl₃); ¹H NMR (400 MHz, CDCl₃) δ 7.84-7.82 (m, 3H), 7.53-7.42 (m, 5H), 7.34-7.24 (m, 5H), 7.19-7.14 (m, 3H), 4.23-4.14 (m, 1H), 4.13-4.03 (m, 1H), 3.12 (dt, J=4.8 Hz, 12.8 Hz, 1H), 2.80-2.72 (m, 1H), 2.67-2.57 (m, 2H), 1.85-1.73 (m, 1H), 1.47-1.36 (m, 1H), 1.12 (t, J=6.8 Hz, 3H); ¹³C NMR (100 MHz, CDCl₃) δ 173.2, 165.3, 141.2, 139,8, 134.5, 131.6, 128.6, 128.5, 128.33, 128.32, 127.7, 127.0, 125.8, 65.9, 62.4, 35.7, 32.1, 26.5, 13.8; IR (CHCl₃) ν 3414, 3061, 3026, 2979, 2943, 1724, 1672, 1510, 1480, 1292, 1243, 1094 cm⁻¹.

Example 61

General Procedure for Preparation of β-ketone Esters

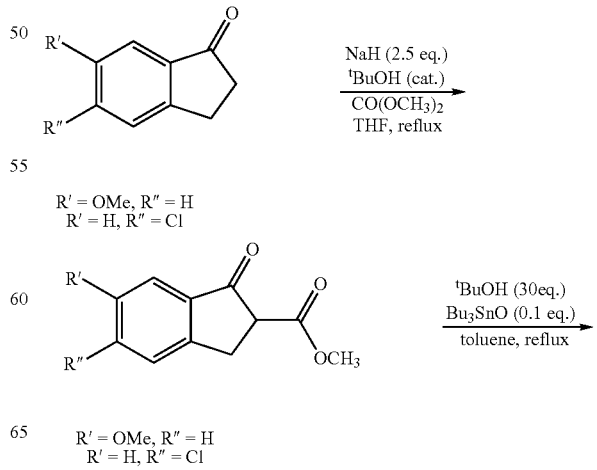

-continued

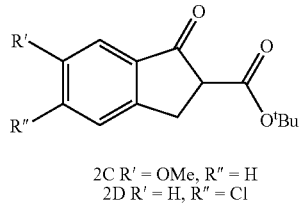

2C R' = OMe, R" = H
2D R' = H, R" = Cl

An oven-dried three-necked flask was charged with NaH assay (2.5 mmol) and dry THF (5 mL) under $N_2$. The suspension was stirred at room temperature for 5 min and stood for 5 min. The upper layer was removed by a syringe and the residue was dried under vacuum. The fine white powder was suspended in THF (5 mL) and to this suspension dimethyl carbonate (10 mmol) was added via a syringe. The mixture was refluxed while a solution of 6-methoxy-1-indanone (1.0 mmol) in THF (5 mL) was introduced dropwise through a dropping funnel over 30 min. The resulting brown mixture was refluxed for an additional 15 min. The resultant green mixture was cooled down to 0° C. and slowly added acetic acid (2 mL) via a syringe. The corresponding mixture was further acidified by addition of an aqueous solution of HCl (1N, 2 mL). The mixture was extracted with EtOAc (3×10 mL). The combined extracts were washed with water, 5% $NaHCO_3$, brine, dried over $Na_2SO_4$ and concentrated. The residue was subjected to purification on silica gel (hexanes/EtOAc 20/1) to give β-keto methyl ester (90-95% yield) as a white solid. For Methyl-5-chloro-1-oxo-2-indanecarboxylate: $^1$H NMR ($CDCl_3$, 400 MHz) (67% of keto form): δ ppm 7.71 (d, J=8.0 Hz, 1H), 7.51 (s, 1H), 7.38 (d, J=8.0 Hz, 1H), 3.81 (s, 3H), 3.76 (dd, J=8.4, 4.0 Hz, 1H), 3.56 (dd, J=17.6, 4.0 Hz, 1H), 3.36 (dd, J=17.6, 8.4 Hz, 1H). $^1$H NMR ($CDCl_3$, 400 MHz) (33% of enol form): δ ppm 10.35 (br s, 1H), 7.56 (d, J=8.0 Hz, 1H), 7.46 (s, 1H), 7.37 (d, J=8.0 Hz, 1H), 3.86 (s, 3H), 3.51 (s, 2H). For Methyl-6-methoxy-1-oxo-2-indanecarboxylate: $^1$H NMR ($CDCl_3$, 400 MHz) (90% of keto form): δ ppm 7.39 (d, J=8.4 Hz, 1H), 7.23 (dd, J=8.4, 2.8 Hz, 1H), 7.19 (d, J=2.8 Hz, 1H), 3.84 (s, 3H), 3.80 (s, 3H), 3.77 (dd, J=8.4, 4.0 Hz, 1H), 3.48 (dd, J=16.8, 4.0 Hz, 1H), 3.31 (dd, J=16.8, 4.0 Hz, 1H). $^1$H NMR ($CDCl_3$, 400 MHz) (10% of enol form): δ ppm 10.40 (br s, 1H), 7.35 (d, J=8.4 Hz, 1H), 7.16 (d, J=2.0 Hz, 1H), 7.00 (d, J=8.4, 2.0 Hz, 1H), 3.862 (s, 3H), 3.859 (s, 3H), 3.45 (s, 2H).

An oven-dried flask was charged with β-keto methyl ester (1.0 mmol), $Bu_2SnO$ (26 mg, 0.1 mmol, 0.1 eq.), $^t$BuOH (5 mL) and toluene (15 mL). The flask was connected a Dean-Star trap which continuingly removed methanol while refluxing. $^t$BuOH (2 mL) was added when the mixture of alcohols and toluene was released through Dean-Star trap. The mixture was refluxed for 4 hours. The resultant yellow solution was concentrated on a water evaporator. The residue was directly loaded on silica gel column for purification (hexanes/EtOAc 20/1) to give β-keto $^t$Butylester (80-84% yield) as a white solid (6-methoxyindanone) and a purple solid (5-chloroindanone), respectively. For 5-chloroindanone ester (84%) 22D: $^1$H NMR ($CDCl_3$, 400 MHz) (85% keto ester form): δ ppm 7.68 (d, J=8.0 Hz, 1H), 7.49 (s, 1H), 7.36 (d, J=8.0 Hz, 1H), 3.63 (dd, J=8.0, 4.0 Hz, 1H), 3.48 (dd, J=17.2, 4.0 Hz, 1H), 3.31 (dd, J=17.2, 4.0 Hz, 1H), 1.49 (s, 9H). (15% enol form): δ ppm 10.25 (br s, 1H), 7.53 (d, J=7.6 Hz, 1H), 7.42 (s, 1H), 7.35 (d, J=7.6 Hz, 1H), 3.46 (s, 2H), 1.57 (s, 9H). $^3$C NMR ($CDCl_3$, 100 MHz) (keto and enol forms): δ ppm 198.46, 167.85, 155.07, 141.77, 133.88, 128.50, 127.18, 126.70, 125.59, 125.01, 121.38, 82.28, 54.39, 32.71, 29.99, 28.42, 27.96. FT-IR (ν, $cm^{-1}$): 2980 (m), 2933 w), 1716 (s, with a shoulder at 1745), 1649 (m), 1601 (m), 1369 (m), 1260 (m), 1154 (s). For 6-methoxyindanone ester (80%) 22C: $^1$H NMR ($CDCl_3$, 400 MHz) (90% keto ester form): δ ppm 7.38 (d, J=8.0 Hz, 1H), 7.20 (m, 2H), 3.83 (s, 3H), 3.64 (dd, J=8.0, 3.6 Hz, 1H), 3.40 (dd, J=16.8, 3.6 Hz, 1H), 3.26 (dd, J=16.8, 8.0 Hz, 1H), 1.49 (s, 9H). (10% enol form): δ ppm 10.52 (br s, 1H), 7.32 (d, J=8.4 Hz, 1H), 7.13 (d, J=2.0 Hz, 1H), 6.96 (dd, J=8.4, 2.0 Hz, 1H), 3.85 (s, 3H), 3.40 (s, 2H), 1.57 (s, 9H). $^{13}$C NMR ($CDCl_3$, 100 MHz) (keto and enol forms): δ ppm 199.94, 168.32, 159.53, 146.53, 136.56, 127.11, 124.64, 105.48, 81.92, 55.53, 55.04, 29.62, 28.41, 27.94. FT-IR (ν, $cm^{-1}$): 2980 (m), 1709 (s, with a shoulder at 1740), 1645 (m), 1494 (m), 1277 (m), 1149 (s), 1028 (m).

Example 61b

Preparation of β-ketone Esters 22F, 22G

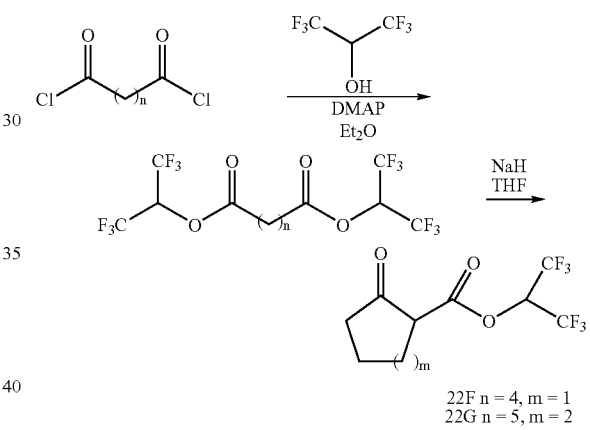

22F n = 4, m = 1
22G n = 5, m = 2

Di-hexafluoro isopropyl Adipate (3.9 g) in 100 mL THF was added to a suspension of NaH (60% in mineral oil, 750 mg) in THF (10 mL). The reaction mixture was heated up to 50° C. (oil bath temperature) for 18 hr. After cooled down to 0° C., HCl (2N aq.) was added dropwise until pH=1. Then the mixture was extracted with ethyl acetate (100 mL), the organic layer was washed with brine and dried with $Na_2SO_4$. After concentration and column purification (silica gel, hexanes:EA=50:1), 22F was obtained as a colorless oil with 65% yield and 14% of it was enol form and 86% was ketone form. $^1$H NMR (400 MHz, $CDCl_3$) δ 9.80 (s, 0.14H, enol-H), 5.90-5.84(m, 0.14H), 5.83-5.74 (m, 0.86H), 3.39-3.34 (m, 0.86H), 2.63-1.89 (m, 6H); $^{13}$C NMR (100 MHz, $CDCl_3$) δ 209.3, 166.4, 120.2(q, $^1J_{C,F}$=277.1 Hz), 98.2, 66.9(hept, $^2J_{C,F}$=34.2 Hz), 65.6(hept, $^2J_{C,F}$=34.9 Hz), 53.8, 37.7, 33.0, 27.2, 26.3, 20.8, 19.1. The same procedure was applied in the synthesis of 22G (17% conversion, 15% yield, 80% enol form and 20% ketone form). $^1$H NMR (400 MHz, $CDCl_3$) δ 11.41 (s, 0.8H, enol-H), 5.91-5.79 (m, 1H), 3.62-3.59 (m, 0.2H), 2.57-1.63 (m, 8H); $^{13}$C NMR (100 MHz, $CDCl_3$) δ 176.8, 168.5, 148.9, 140.0, 120.5(q, $^1J_{C,F}$= 283.9 Hz), 96.0, 65.9(hept, $^2J_{C,F}$=34.9 Hz), 61.7, 56.7, 41.5, 29.5, 27.0, 22.0, 21.8, 21.5.

Example 62

Preparation of Alkenylaryl Ketones 23c and 23d

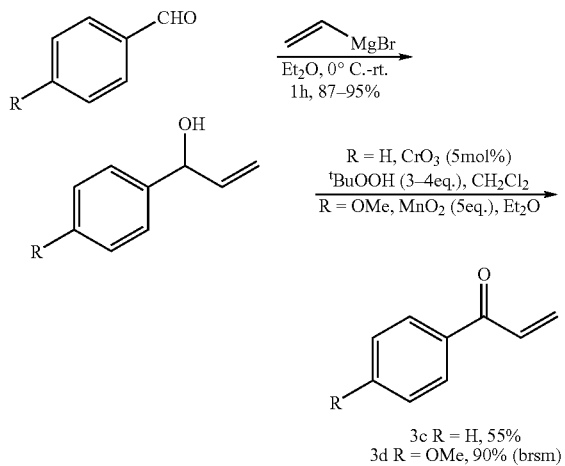

3c R = H, 55%
3d R = OMe, 90% (brsm)

An oven-dried three-necked flask with a dropping funnel was charged with benzaldehyde (3.13 g, 30 mmol) and anhydrous ether (100 mL) at 0° C. under $N_2$. Vinylmagnesium bromide (1.0M in THF, 45 mL, 45 mmol, 1.5 eq.) was added into the aldehyde solution through a dropping funnel over 30 min. The corresponding white suspension was stirred at 0° C. for 1 hour and an additional 30 min at room temperature. The reaction was quenched with slow addition of an aqueous solution of HCl at 0° C. The organic layer was collected and the aqueous layer was extracted with ether. The combined extracts were washed with water, brine, dried over $Na_2SO_4$ and concentrated. The residue was subjected to purification on silica gel (hexanes/EtOAc 10/1) to give the desired allylic alcohol (3.5 g, 87% yield) as a light yellow oil. For phenyl allylic alcohol: $^1$H NMR (CDCl$_3$, 400 MHz): δ ppm 7.30-7.40 (m, 5H), 6.04 (ddd, J=17.2, 10.4, 6.8 Hz, 1H), 5.34 (dd, J=17.2, 1.6 Hz, 1H), 5.18 (d, J=9.6 Hz, 1H), 5.18 (brs, 1H), 4.66 (s, 1H). For p-methoxyphenyl allylic alcohol (95% yield): $^1$H NMR (CDCl$_3$, 400 MHz): δ ppm 7.30 (d, J=8.8 Hz, 2H), 6.89 (d, J=8.8 Hz, 2H), 6.05 (ddd, J=17.2, 10.4, 6.0 Hz, 1H), 5.34 (dt, J=17.2, 1.2 Hz, 1H), 5.19 (dt, J=10.4, 1.2 Hz, 1H), 5.17 (brs, 1H), 3.81 (s, 3H).

Example 62a

Phenyl Vinyl Ketone 23c

To a solution of phenyl allylic alcohol (3.0 g, 22.4 mmol) in CH$_2$Cl$_2$ was added CrO$_3$ (112 mg, 1.12 mmol, 5 mol %). $^t$BuOOH (70%, 7.2 M in H$_2$O, 10 mL, mmol, 3.2 eq.) was added via a syringe at 0° C. over 1 h. The resulting brown mixture was stirred at room temperature overnight. The corresponding yellow suspension was added solid Na$_2$S$_2$O$_3$ (20 g) at 0° C. The mixture was vigorously stirred at room temperature for 30 min. The resultant brown mixture was concentrated and extracted with ether (30 mL×3). The combined extracts were washed with water, brine and over Na$_2$SO$_4$ and concentrated. The residue was subjected to purification on silica gel (hexanes/EtOAc 20/1) to give a vinyl ketone (1.6 g, 55% yield) as a light yellow oil. $^1$H NMR (CDCl$_3$, 400 MHz): δ ppm 7.93 (dd, J=8.0, 1.0 Hz, 2H), 7.42-7.46 (m, 3H), 7.14 (dd, J=17.2, 10.4 Hz, 1H), 6.43 (dd, J=17.2, 1.0 Hz, 1H), 5.92 (dd, J=10.4, 1.0 Hz, 1H).

Example 62b p-Methoxyphenyl Vinyl Ketone 23d

To a solution of p-methoxyphenyl allylic alcohol (1.0 g, 6.1 mmol) in Et$_2$O (20 mL) was added MnO$_2$ (activated, 3.5 g, 40.2 mmol, 6.6 eq.) in portions at room temperature over 1 h. The reaction mixture was vigorously stirred at room temperature for 30 min. The black suspension was concentrated to ca. 5 mL of liquid left and directly loaded on silica gel column for purification (pure hexanes and subsequent hexanes/EtOAc 10/1) to give p-methoxyphenyl vinyl ketone (0.40 g, 41% yield) as a colorless oil and a recycled allylic alcohol (0.57 g, 57% yield). $^1$H NMR (CDCl$_3$, 400 MHz): δ ppm 7.97 (d, J=9.2 Hz, 2H), 7.18 (dd, J=17.2, 10.4 Hz, 1H), 6.96 (d, J=9.2 Hz, 2H), 6.43 (dd, J=17.2, 2.0 Hz, 1H), 5.88 (dd, J=10.4, 2.0 Hz, 1H), 3.88 (s, 3H).

Example 63

General Procedure for the Preparation of Racemic Adducts

At room temperature to a solution of a β-ketone ester 22 (0.1 mmol) in CH$_2$Cl$_2$ (1.0 M) was added DABCO or Et$_3$N. Then 23 (2.5 eq.) was added dropwise. After the reaction went to completion, the reaction mixture was purified by flash chromatography (silica gel, Hexanes:EA=10:1) or preparative TLC.

Example 64

General Procedures for Enantioselective Michael Addition of β-ketone Esters to α,β-unsaturated Ketone

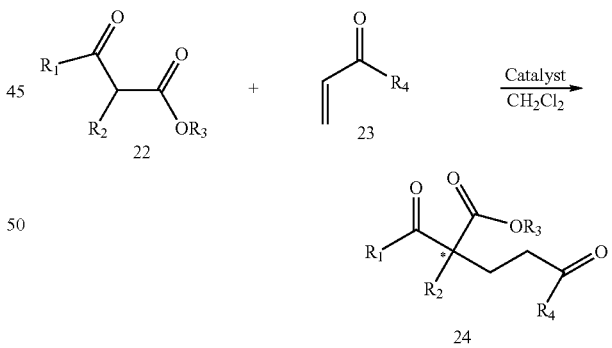

Example 64a

Enantioselective Michael Addition of β-ketone Esters to α,β-unsaturated Ketone with 10 mol % Catalyst Modified cinchona alkaloid catalyst (10 mol %) was added to the solution of β-ketone ester 22 (0.3 mmol) in 0.6 mL of dichloromethane, α,β-unsaturated ketone 23 (2.5 eq. to 22) was added dropwise to this solution at the temperature indicated in table 11. The reaction was monitored by TLC or ¹HNMR. After 22 was almost consumed, the reaction mixture was purified with flash chromatography (silica gel, Hexanes:ethyl acetate=10:1) directly without any work-up. The catalyst was recycled by being washed down from column using methanol with a recycling yield above 95% (in NMR pure).

Example 64b

Enantioselective Michael Addition of β-ketone Esters to a p-unsaturated Ketone with 1 mol % Catalyst A vial was charged with β-keto ester 22 (0.2 mmol) and a solution of Q-4c or QD-4c (5 mom in $CH_2Cl_2$, 0.4 mL, 1.0 mol %) in dichloromethane. The mixture was shacked at room temperature for 1 min, and then added alkenyl ketone 23 via a syringe (2.5 eq to 2). The resultant mixture was occasionally shaken at room temperature until reaction went to completion. The reaction mixture was directly loaded on silica gel for purification (hexanes/EtOAc 10:1~7:1) to give the desired product.

Example 64c

General Procedure for Enantioselective Michael Addition of (3-ketone Esters to α,β-unsaturated Ketone Via Slow Addition Modified cinchona alkaloid catalyst (10 mol %) was added to the solution of β-ketone ester 22 (0.2 mmol) in 0.4 mL of dichloromethane, α,β-unsaturated ketone 23 (2.5 eq. to 22) in 0.4 mL of dichloromethane was added at a speed of 0.07 mL/h via a syringe (which was controlled by a syringe pump) to this solution at the temperature indicated in table 11. After adding, the reaction was monitored by TLC or ¹HNMR. After 22 was almost consumed, the reaction mixture was purified with flash chromatography (silica gel, Hexanes:ethyl acetate=10:1) directly without any work-up. The reaction time shown in table 11 included the time of adding. The catalyst was recycled by being washed down from column using methanol with a recycling yield above 95% (in NMR pure).

Example 65

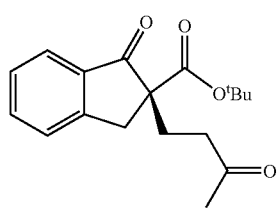

24Ba (R)-(+)-tert-Butyl 1-oxo-2-(3-oxobutyl) 2-indancarboxylate 24Ba

This product was obtained as a colorless oil in 96% yield after flash chromatography and 96% ee as determined by HPLC analysis [Daicel chiralcel OJ, Hexanes:IPA, 90:10, 1.00 ml/min, λ 220 nm, t (major)=17.4 min, t (minor)=9.2 min] from a reaction catalyzed by Q-4c (1 mol %) at r.t. for 3 hour. $[\alpha]_D^{25}$=+30.9 (c 1.50, $CHCl_3$); ¹H NMR (400 MHz, $CDCl_3$) δ 7.76 (d, J=8.0 Hz, 1H), 7.62 (td, J=7.2 Hz, J=1.2 Hz, 1H), 7.47 (d, J=8.0 Hz, 1H), 7.40 (t, J=7.2 Hz, 1H), 3.61(d, J=17.2 Hz, 1H), 3.01(d, J=17.2 Hz, 1H), 2.68-2.47 (m, 2H), 2.21-2.16(m, 2H), 2.13(s, 3H), 1.39(s, 9H); ¹³C NMR (100 MHz, $CDCl_3$) δ 207.6, 202.7, 170.1, 152.6, 135.2, 127.7, 126.3, 124.6, 81.9, 59.8, 38.8, 37.9, 29.8, 28.3, 27.2; IR ($CHCl_3$) ν 2978, 2932, 1733, 1715, 1607, 1368, 1153 $cm^{-1}$. The absolute configuration of (+)-24Ba was determined to be R isomer by comparing the specific optical rotation with literature value Nakajima, M.; Yamamoto, S.; Yamaguchi, Y.; Nakamura, S.; Hashimoto, S. *Tetrahedron*, 2003, 59, 7307-7313; [1]. $[\alpha]_D^{25}$=+43.2 (c 2.50, Benzene) for 96% ee.

(S)-(-)-tert-Butyl 1-oxo-2-(3-oxobutyl) 2-indancarboxylate 24Ba

This product was obtained as a colorless oil in 93% yield after flash chromatography and 95% ee from a reaction catalyzed by QD-4c (1 mol %) at r.t. for 3 h. $[\alpha]_D^{25}$=−34.4 (c 1.53, $CHCl_3$).

Example 66

(+)-tert-Butyl 1-oxo-2-(3-oxopentyl) 2-indancarboxylate 24Bb

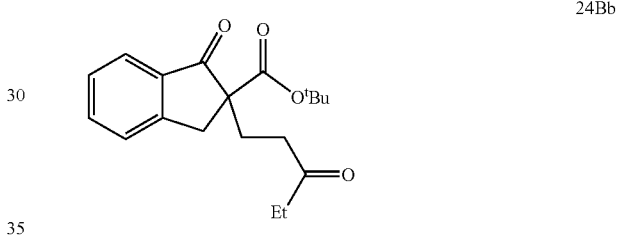

24Bb

This product was obtained as a colorless oil in 94% yield after flash chromatography and 94% ee as determined by HPLC analysis [Daicel chiralcel OJ, Hexanes:IPA, 90:10, 1.00 ml/min, λ 220 nm, t (major)=9.5 min, t (minor)=7.2 min] from a reaction catalyzed by Q-4c (1 mol %) at r.t. for 5 hours. $[\alpha]_D^{25}$=+35.7 (c 1.46, $CHCl_3$); ¹H NMR (400 MHz, $CDCl_3$) δ 7.76 (d, J=7.6 Hz, 1H), 7.62 (td, J=7.2 Hz, J=1.2 Hz, 1H), 7.47 (d, J=8.0 Hz, 1H), 7.40 (t, J=7.6 Hz, 1H), 3.61(d, J=17.6 Hz, 1H), 3.01(d, J=16.8 Hz, 1H), 2.63-2.56 (m, 1H), 2.51-2.38 (m, 2H), 2.26-2.13(m, 3H), 1.39(s, 9H), 1.03(t, J=7.6 Hz, 3H); ¹³C NMR (100 MHz, $CDCl_3$) δ 210.3, 202.7, 170.1, 152.6, 135.3, 135.2, 127.7, 126.3, 124.6, 81.9, 60.0, 37.8, 37.5, 35.8, 28.5, 27.8, 7.7; IR ($CHCl_3$) ν 2977, 2936, 1733, 1713, 1608, 1368, 1153 $cm^{-1}$; HRMS (CI) m/z calcd. for ($C_{19}H_{24}O_4$+H⁺): 317.1753, found 317.1756.

Example 67

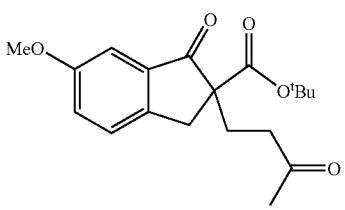

24Ca (+)-24Ca This product was obtained as a colorless oil in 98% yield after flash chromatography and 96% ee as determined by HPLC analysis [Daicel chiralcel OJ, Hexanes:IPA, 90:10, 1.00 ml/min, λ 220 nm, t (major)=31.3 min, t (minor)=10.3 min] from a reaction catalyzed by Q-4c (1 mol %) at r.t. for 5 hours. $[\alpha]_D$=+35.4° (c 0.63, CHCl$_3$); $^1$H NMR (CDCl$_3$, 400 MHz): δ ppm 7.35 (d, J=8.0 Hz, 1H), 7.21 (dd, J=8.0, 2.0 Hz, 7.18 (d, J=2.0 Hz, 1H), 3.84 (s, 3H), 3.51 (d, J=16.8 Hz, 1H), 2.92 (d, J=16.8 Hz, 1H), 2.44-2.66 (m, 2H), 2.18 (m, 2H), 2.13 (s, 3H), 1.40 (s, 9H); $^{13}$C NMR (CDCl$_3$, 100 MHz): δ ppm 207.67, 202.69, 170.20, 159.61, 145.45, 136.48, 126.97, 124.68, 105.62, 81.92, 60.60, 55.54, 38.82, 37.28, 29.87, 28.40, 27.78; FT-IR (ν, cm$^{-1}$): 2978 (m), 2935 (m), 1750 (s), 1712 (s), 1618 (m), 1494 (s), 1279 (s), 1155 (s), 1027 (m), 847 (m), 766 (m); HRMS (CD) m/z calcd. for (C$_{19}$H$_{24}$O$_5$+H$^+$): 333.1701, found 333.1694.

(−)-24Ca This product was obtained as a colorless oil in 99% yield after flash chromatography and 96% ee from a reaction catalyzed by QD-4c (1 mol %) at r.t. for 5 h. $[\alpha]_D$=−28.4° (c 0.57, CHCl$_3$).

Example 68

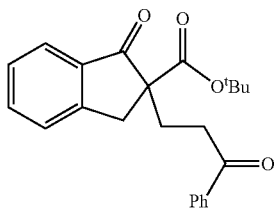

24Bc (+)-24Bc. This product was obtained as a white solid in 94% yield and 96% ee as determined by HPLC analysis [Daicel chiralpak AS, Hexanes:IPA, 90:10, 1.00 ml/min, λ 220 nm, t (major)=15.8 min, t (minor)=19.4 min] from a reaction catalyzed by Q-4c (10 mol %) at −24° C. for 30 min. $[\alpha]_D^{25}$=+4.2 (c 1.14, CHCl$_3$); $^1$H NMR (400 MHz, CDCl$_3$) δ 7.96-7.94 (m, 2H), 7.78 (d, J=7.2 Hz, 1H), 7.63 (td, J=7.6 Hz, J=1.2 Hz, 1H), 7.57-7.53 (m, 1H), 7.49-7.39 (m, 4H), 3.67(d, J=17.6 Hz, 1H), 3.01(d, J=17.6 Hz, 1H), 3.23-3.02(m, 2H), 2.43-2.27(m, 2H), 1.41 (s, 9H); $^3$C NMR (100 MHz, CDCl$_3$) δ 202.7, 199.3, 170.1, 152.7, 136.6, 135.3, 135.2, 133.0, 128.5, 128.1, 127.7, 126.3, 124.7, 82.0, 60.2, 37.9, 34.1, 29.2, 27.8; IR (CHCl$_3$) ν 2978, 2932, 1736, 1710, 1686, 1607, 1449, 1368, 1255, 1212, 1152 cm$^{-1}$; HRMS (CI) m/z calcd. for (C$_{23}$H$_{24}$O$_4$+H$^+$): 365.1752, found 365.1759.

(−)-24Bc. This product was obtained as a colorless oil in 94% yield after flash chromatography and 93% ee from a reaction catalyzed by QD-4c (10 mol %) at −24° C. for 30 min. $[\alpha]_D^{25}$=−5.6 (c 0.32, CHCl$_3$).

Example 69

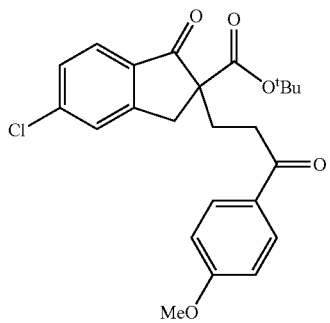

24Dd (−)-24Dd. This product was obtained as a white solid in 94% yield after flash chromatography and 96% ee as determined by HPLC analysis [Daicel chiralcel OD, Hexanes:IPA, 90:10, 1.00 ml/min, λ 220 nm, t (major)=12.2 min, t (minor)=19.2 min] from a reaction catalyzed by Q-4c (10 mol %) at −24° C. for 8 h with slow addition of 3d. $[CL]D^{25}$=−10.6 (c 0.70, CHCl$_3$); $^1$H NMR (400 MHz, CDCl$_3$) δ 7.93 (d, J=8.4 Hz, 2H), 7.71 (d, J=8.0 Hz, 1H), 7.46 (s, 1H), 7.39 (dd, J=8.0 Hz, J=1.2 Hz, 1H), 6.92 (d, J=9.2 Hz, 2H), 3.87(s, 3H), 3.64(d, J=18.0 Hz, 1H), 3.07(d, J=17.6 Hz, 1H), 3.14-2.93(m, 2H), 2.43-2.26(m, 2H), 1.41 (s, 9H); $^{13}$C NMR (100 MHz, CDCl$_3$) δ 201.2, 197.7, 169.7, 163.5, 154.2, 141.8, 133.8, 130.4, 129.7, 128.6, 126.6, 125.8, 113.7, 82.3, 60.6, 55.4, 37.5, 33.6, 29.3, 27.8; IR (CHCl$_3$) ν 2978, 1737, 1712, 1600, 1258, 1170, 1153 cm$^{-1}$; HRMS (CI) m/z calcd. for (C$_{24}$H$_{25}$ClO$_5$+H$^+$): 429.1468, found 429.1475.

(+)-24Dd. This product was obtained as a colorless oil in 93% yield after flash chromatography and 93% ee from a reaction catalyzed by QD-4c (10 mol %) with slow addition at −24° C. for 8 h with slow addition of 23d. $[\alpha]_D^{25}$=+12.1 (c 1.22, CHCl$_3$).

Example 70

(S)-(−)-tert-Butyl 2-oxo-1-(3-oxobutyl) cyclopentanecarboxyle

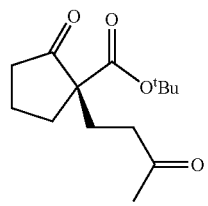

24Ea

24Ea. This product was obtained as a colorless oil in 95% yield after flash chromatography and 96% ee as determined by HPLC analysis [Daicel chiralpak AS, Hexanes:IPA, 99:1, 0.44 ml/min, λ 215 nm, t (major)=47.6 min, t (minor)=40.4 min] from a reaction catalyzed by Q-4c (10 mol %) at r.t. for 84 hr. $[\alpha]_D^{25}$=−5.9 (c 0.53, CHCl$_3$); $^1$H NMR (400 MHz, CDCl$_3$) δ 2.78-2.71 (m, 1H), 2.50-2.35 (m, 3H), 2.31-2.22 (m, 1H), 2.14 (s, 3H), 2.07-1.81 (m, 5H), 1.44 (s, 9H); $^{13}$C NMR (100 MHz, CDCl$_3$) δ 215.3, 208.1, 170.7, 82.0, 59.4, 38.9, 38.0, 34.6, 29.9, 27.9, 27.0, 19.6; IR (CHCl$_3$) ν 2975, 1747, 1716, 1368, 1146 cm$^{-1}$. The absolute configuration of (−)-24Ea was determined to be S isomer by comparing the specific optical rotation with literature value. Hamashima, Y.; Hotta, D.; Sodeoka, M. J. Am. Chem. Soc., 2002, 124, 11240-11241.

Example 71

(+) Hexafluoroisopropyl 2-oxo-1-(3-oxobutyl) cyclopentane carboxylate

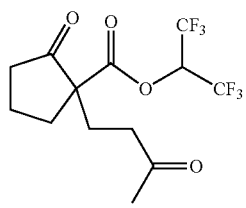

24Fa (+)24Fa. This product was obtained as a colorless oil in 93% yield after flash chromatography and 96% ee as determined by HPLC analysis [REGIS (R,R) Whelk-O1, Hexanes:IPA, 99:1, 1.00 ml/min, λ 215 nm, t (major)=11.5 min, t (minor)=13.6 min] from a reaction catalyzed by Q-4c (10 mol %) at r.t. for 30 min. $[\alpha]_D^{25}$=+0.24 (c 2.5, CHCl$_3$); $^1$H NMR (400 MHz, CDCl$_3$) δ 5.81-5.72 (m, 1H), 2.75-2.67 (m, 1H), 2.52-2.41 (m, 4H), 2.23-1.98 (m, 5H), 2.14 (s, 3H); $^{13}$C NMR (100 MHz, CDCl$_3$) δ 212.1, 207.1, 168.5, 120.1 (q, $^1J_{C,F}$=280.8 Hz), 66.7 (hept, $^2J_{C,F}$=34.2 Hz), 58.6, 38.2, 37.6, 34.1, 29.8, 26.6, 19.5; IR (CHCl$_3$) ν 2971, 1779, 1742, 1716, 1386, 1359, 1289, 1234, 1201, 1167, 906 cm$^{-1}$. HRMS (CI) m/z calcd. for (C$_{13}$H$_{14}$F$_6$O$_4$+H$^+$): 349.0875, found 349.0880. This product was obtained as a colorless oil in 92% yield after flash chromatography and 94% ee from a reaction catalyzed by Q-4c (1 mol %) at r.t. for 24 h. $[\alpha]_D^{25}$+0.10 (c 1.00, CHCl$_3$).

(−) Hexafluoroisopropyl 2-oxo-1-(3-oxobutyl) cyclopentane carboxylate (−)24Fa. This product was obtained as a colorless oil in 90% yield after flash chromatography and 95% ee from a reaction catalyzed by QD-4c (10 mol %) at r.t. for 30 min. $[\alpha]_D^{25}$=−0.83 (c 2.05, CHCl$_3$).

Example 72

(−) Hexafluoroisopropyl 2-oxo-1-(3-oxobutyl) cyclopentane carboxylate

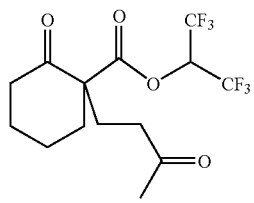

24Ga (−)24Ga. This product was obtained as a colorless oil in 89% yield after flash chromatography and 98% ee as determined by HPLC analysis [REGIS (R,R) Whelk-O1, Hexanes:IPA, 99:1, 0.90 ml/min, λ 215 nm, t (major)=15.6 min, t (minor)=14.3 min] from a reaction catalyzed by Q-4c (10 mol %) at r.t. for 24 h. $[\alpha]_D^{25}$=−46.1 (c 3.67, CHCl$_3$); $^1$H NMR (400 MHz, CDCl$_3$) δ 5.87-5.78 (m, 1H), 2.61-2.42 (m, 4H), 2.38-2.30 (m, 1H), 2.26-2.18 (m, 1H), 2.05-1.94 (m, 2H), 1.86-1.61 (m, 4H), 2.13 (s, 3H); $^{13}$C NMR (100 MHz, CDCl$_3$) δ 206.7, 250.7, 169.4, 120.2 (q, $^JC,F$=280.8 Hz), 66.7(hept, $^2J_{C,F}$=34.2 Hz), 60.2, 40.4, 38.2, 36.4, 29.8, 27.8, 27.2, 21.9; IR (CHCl$_3$) ν 2953, 2872, 1770, 1716, 1721, 1386, 1359, 1288, 1233, 1202, 1110, 906 cm$^{-1}$. HRMS (CI) m/z calcd. for (C$_{14}$H$_{16}$F$_6$O$_4$+H$^+$): 363.1031, found 363.1028.

(+) Hexafluoroisopropyl 2-oxo-1-(3-oxobutyl) cyclopentane carboxylate (+)24Ga. This product was obtained as a colorless oil in 86% yield after flash chromatography and 96% ee from a reaction catalyzed by QD-4c (10 mol %) at r.t. for 24 h. $[\alpha]_D^{25}$=+44.4 (c 3.45, CHCl$_3$).

Example 73

(+) Hexafluoroisopropyl 2-propionyl-2-Methyl-5-oxohexanoate

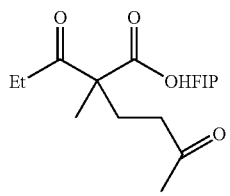

24Ha (+)24Ha. This product was obtained as a colorless oil in 82% yield after flash chromatography and 90% ee as determined by HPLC analysis [Daicel chiralcel OD, Hexanes: IPA, 99:1, 1.00 ml/min, λ 215 nm, t (major)=15.8 min, t (minor)=8.5 min] from a reaction catalyzed by Q-4c (10 mol %) at −24° C. for 20 hours. $[\alpha]_D^{25}$=+4.3 (c 0.67, CHCl$_3$); $^1$H NMR (400 MHz, CDCl$_3$) δ 5.84-5.75 (m, 1H), 2.52-2.40 (m, 4H), 2.26-2.10 (m, 2H), 2.15(s, 3H), 1.44(s, 3H), 1.07(t, J=6.4 Hz, 3H); $^3$C NMR (100 MHz, CDCl$_3$) δ 206.8, 206.4, 170.2, 120.4 (q, $^1J_{C,F}$=280.9 Hz), 67.0(hept, $^2J_{C,F}$=34.9 Hz), 58.9, 38.3, 31.8, 30.1, 28.5, 19.5, 8.0; IR (CHCl$_3$) ν 2974, 1771, 1717, 1386, 1288, 1233, 1110, 907 cm$^{-1}$. HRMS (CI) m/z calcd. for (C$_{13}$H$_{16}$F$_6$O$_4$+H): 351.1031, found 351.1036.

(−) Hexafluoroisopropyl 2-propionyl-2-Methyl-5-oxohexanoate (−)24Ha. This product was obtained as a colorless oil in 85% yield after flash chromatography and 90% ee from a reaction catalyzed by QD-4c (10 mol %) at −24° C. for 40 hours. $[\alpha]_D^{25}$=−4.3 (c 0.99, CHCl$_3$).

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula I:

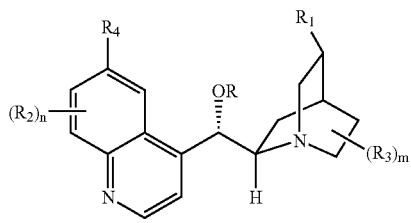

wherein, independently for each occurrence:
R represents a substituted or unsubstituted alkyl, alkenyl, alkynyl, aryl, aralkyl, heteroaryl, heteroaralkyl, heterocyclic, or heterocycloalkyl;
$R_1$ represents a substituted or unsubstituted alkyl or alkenyl;
$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;
n is an integer from 0 to 5 inclusive;
m is an integer from 0 to 8 inclusive; and
$R_4$ represents —OH, —OTf, —ONf, —SH, —$NH_2$, —$NHR_2$—$NH(C=O)NR_2R_3$, —$NH(SO_2)R_2$, —$NH(C=O)OR_2$, or —$NH(C=O)R_2$.

2. The compound of claim 1, wherein $R_4$ represents —OH.
3. The compound of claim 2, wherein R represents aryl or aralkyl.
4. The compound of claim 2, wherein R represents aryl.
5. The compound of claim 2, wherein R represents phenanthrene.
6. The compound of claim 2, wherein R represents aralkyl.
7. The compound of claim 2, wherein R represents benzyl.
8. The compound of claim 2, wherein $R_1$ is alkyl.
9. The compound of claim 2, wherein $R_1$ is ethyl.
10. The compound of claim 2, wherein $R_1$ is alkenyl.
11. The compound of claim 2, wherein $R_1$ is —CH=$CH_2$.
12. The compound of claim 2, wherein n is 0.
13. The compound of claim 2, wherein m is 0.
14. The compound of claim 2, wherein R is aryl and $R_1$ is alkyl.
15. The compound of claim 2, wherein R is phenanthrene and $R_1$ is alkyl.
16. The compound of claim 2, wherein R is phenanthrene and $R_1$ is ethyl.
17. The compound of claim 2, wherein R is aryl and $R_1$ is alkenyl.
18. The compound of claim 2, wherein R is phenanthrene and $R_1$ is alkenyl.
19. The compound of claim 2, wherein R is phenanthrene and $R_1$ is —CH=$CH_2$.
20. The compound of claim 2, wherein R is aralkyl and $R_1$ is alkyl.
21. The compound of claim 2, wherein R is benzyl and $R_1$ is alkyl.
22. The compound of claim 2, wherein R is benzyl and $R_1$ is ethyl.
23. The compound of claim 2, wherein R is aralkyl and $R_1$ is alkenyl.
24. The compound of claim 2, wherein R is benzyl and $R_1$ is alkenyl.
25. The compound of claim 2, wherein R is benzyl and $R_1$ is —CH=$CH_2$.
26. The compound of claim 2, wherein R is aryl, $R_1$ is alkyl, m is 0, and n is 0.
27. The compound of claim 2, wherein R is phenanthrene, $R_1$ is alkyl, m is 0, and n is 0.
28. The compound of claim 2, wherein R is phenanthrene, $R_1$ is ethyl, m is 0, and n is 0.
29. The compound of claim 2, wherein R is aryl, $R_1$ is alkenyl, m is 0, and n is 0.
30. The compound of claim 2, wherein R is phenanthrene, $R_1$ is alkenyl, m is 0, and n is 0.
31. The compound of claim 2, wherein R is phenanthrene, $R_1$ is —CH=$CH_2$, m is 0, and n is 0.
32. The compound of claim 2, wherein R is aralkyl, $R_1$ is alkyl, m is 0, and n is 0.
33. The compound of claim 2, wherein R is benzyl, $R_1$ is alkyl, m is 0, and n is 0.
34. The compound of claim 2, wherein R is benzyl, $R_1$ is ethyl, m is 0, and n is 0.
35. The compound of claim 2, wherein R is aralkyl, $R_1$ is alkenyl, m is 0, and n is 0.
36. The compound of claim 2, wherein R is benzyl, $R_1$ is alkenyl, m is 0, and n is 0.
37. The compound of claim 2, wherein R is benzyl, $R_1$ is —CH=$CH_2$, m is 0, and n is 0.

38. A compound represented by formula II:

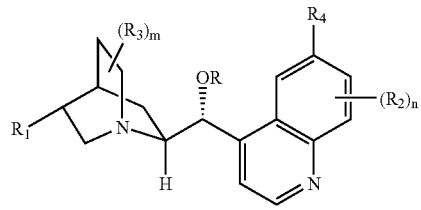

wherein, independently for each occurrence:
R represents a substituted or unsubstituted alkyl, alkenyl, alkynyl, aryl, aralkyl, heteroaryl, heteroaralkyl, heterocyclic, or heterocycloalkyl;
$R_1$ represents alkyl or alkenyl;
$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;
n is an integer from 0 to 5 inclusive;
m is an integer from 0 to 8 inclusive; and
$R_4$ represents —OH, —OTf, —ONf, —SH, —$NH_2$, —$NHR_2$—$NH(C=O)NR_2R_3$, —$NH(SO_2)R_2$, —$NH(C=O)OR_2$, or —$NH(C=O)R_2$.

39. The compound of claim 38, wherein $R_4$ represents —OH.
40. The compound of claim 39, wherein R represents aryl or aralkyl.
41. The compound of claim 39, wherein R represents aryl.

42. The compound of claim 39, wherein R represents phenanthrene.

43. The compound of claim 39, wherein R represents aralkyl.

44. The compound of claim 39, wherein R represents benzyl.

45. The compound of claim 39, wherein $R_1$ is alkyl.

46. The compound of claim 39, wherein $R_1$ is ethyl.

47. The compound of claim 39, wherein $R_1$ is alkenyl.

48. The compound of claim 39, wherein $R_1$ is —CH=CH$_2$.

49. The compound of claim 39, wherein n is 0.

50. The compound of claim 39, wherein m is 0.

51. The compound of claim 39, wherein R is aryl and $R_1$ is alkyl.

52. The compound of claim 39, wherein R is phenanthrene and $R_1$ is alkyl.

53. The compound of claim 39, wherein R is phenanthrene and $R_1$ is ethyl.

54. The compound of claim 39, wherein R is aryl and $R_1$ is alkenyl.

55. The compound of claim 39, wherein R is phenanthrene and $R_1$ is alkenyl.

56. The compound of claim 39, wherein R is phenanthrene and $R_1$ is —CH=CH$_2$.

57. The compound of claim 39, wherein R is aralkyl and $R_1$ is alkyl.

58. The compound of claim 39, wherein R is benzyl and $R_1$ is alkyl.

59. The compound of claim 39, wherein R is benzyl and $R_1$ is ethyl.

60. The compound of claim 39, wherein R is aralkyl and $R_1$ is alkenyl.

61. The compound of claim 39, wherein R is benzyl and $R_1$ is alkenyl.

62. The compound of claim 39, wherein R is benzyl and $R_1$ is —CH=CH$_2$.

63. The compound of claim 39, wherein R is aryl, $R_1$ is alkyl, m is 0, and n is 0.

64. The compound of claim 39, wherein R is phenanthrene, $R_1$ is alkyl, m is 0, and n is 0.

65. The compound of claim 39, wherein R is phenanthrene, $R_1$ is ethyl, m is 0, and n is 0.

66. The compound of claim 39, wherein R is aryl, $R_1$ is alkenyl, m is 0, and n is 0.

67. The compound of claim 39, wherein R is phenanthrene, $R_1$ is alkenyl, m is 0, and n is 0.

68. The compound of claim 39, wherein R is phenanthrene, $R_1$ is —CH=CH$_2$, m is 0, and n is 0.

69. The compound of claim 39, wherein R is aralkyl, $R_1$ is alkyl, m is 0, and n is 0.

70. The compound of claim 39, wherein R is benzyl, $R_1$ is alkyl, m is 0, and n is 0.

71. The compound of claim 39, wherein R is benzyl, $R_1$ is ethyl, m is 0, and n is 0.

72. The compound of claim 39, wherein R is aralkyl, $R_1$ is alkenyl, m is 0, and n is 0.

73. The compound of claim 39, wherein R is benzyl, $R_1$ is alkenyl, m is 0, and n is 0.

74. The compound of claim 39, wherein R is benzyl, $R_1$ is —CH=CH$_2$, m is 0, and n is 0.

\* \* \* \* \*